United States Patent
Yu et al.

(10) Patent No.: US 9,409,897 B2
(45) Date of Patent: Aug. 9, 2016

(54) BENZAMIDE DERIVATIVES AS MODULATORS OF THE FOLLICLE STIMULATING HORMONE

(71) Applicant: Merck Patent GmbH, Darmstadt, DE (US)

(72) Inventors: Henry Yu, Wellesley, MA (US); Thomas E. Richardson, Durham, NC (US); Pandi Bharathi, Cary, NC (US); Brian H. Heasley, Wake Forest, NC (US); Matthew G. Jenks, Durham, NC (US); Robert J. Foglesong, Durham, NC (US)

(73) Assignee: Merck Patent GmbH, Darmstadt (DE)

(*) Notice: Subject to any disclaimer, the term of this patent is extended or adjusted under 35 U.S.C. 154(b) by 144 days.

(21) Appl. No.: 14/364,193

(22) PCT Filed: Jan. 9, 2013

(86) PCT No.: PCT/US2013/020802
§ 371 (c)(1),
(2) Date: Jun. 10, 2014

(87) PCT Pub. No.: WO2013/106409
PCT Pub. Date: Jul. 18, 2013

(65) Prior Publication Data
US 2015/0011562 A1 Jan. 8, 2015

Related U.S. Application Data

(60) Provisional application No. 61/585,077, filed on Jan. 10, 2012.

(51) Int. Cl.
| | |
|---|---|
| *A61B 17/435* | (2006.01) |
| *A61K 31/496* | (2006.01) |
| *C07D 413/14* | (2006.01) |
| *C07D 405/14* | (2006.01) |
| *C07D 405/12* | (2006.01) |
| *C07D 413/12* | (2006.01) |
| *C07D 263/34* | (2006.01) |
| *C07D 307/68* | (2006.01) |
| *C07D 407/12* | (2006.01) |

(52) U.S. Cl.
CPC ............ *C07D 413/14* (2013.01); *A61B 17/435* (2013.01); *A61K 31/496* (2013.01); *C07D 263/34* (2013.01); *C07D 307/68* (2013.01); *C07D 405/12* (2013.01); *C07D 405/14* (2013.01); *C07D 407/12* (2013.01); *C07D 413/12* (2013.01)

(58) Field of Classification Search
CPC ............................ A61B 17/435; A61K 31/496
See application file for complete search history.

(56) References Cited

U.S. PATENT DOCUMENTS 6,653,338 B2   11/2003   El Tayer et al.

FOREIGN PATENT DOCUMENTS

| WO | 0008015 A2 | 2/2000 | |
| WO | WO 01/51456 * | 7/2001 | ............ C07C 259/18 |
| WO | 0209706 A1 | 2/2002 | |
| WO | 2008117175 A2 | 10/2008 | |
| WO | 2009105435 A1 | 8/2009 | |
| WO | 2010136438 A1 | 12/2010 | |
| WO | WO 2013/012848 * | 1/2013 | ............ C07D 401/14 |

OTHER PUBLICATIONS

Biscoe et al., JACS, 2008,130:6686-6687.
Bundgaard H, Design of Prodrugs, 1985, Elsevier.
Bundgaard H, A Textbook of Drug Design and Development, Harwood Academic Publishers, 1991, Chapter 5: 131-191.
Fors et al., JACS, 2008 130:13552-13554.
Houben-Weyl, Methoden der organischen Chemie [Methods of Organic Chemistry], Georg-Thieme-Verlag, Stuttgart.
Wermuth et al., The Practice of Medicinal Chemistry, Academic Press, 1996, Chapter 31:671-696.
Yoshida et al., Int. J. Pharm., 1995, 115:61-67.
International Search Report, dated Jul. 18, 2013.

* cited by examiner

*Primary Examiner* — Erich A Leeser
(74) *Attorney, Agent, or Firm* — Dwight D. Kim; EMD Serono Researcg and Development Institute

(57) ABSTRACT

Novel benzamide derivatives of formula (I)

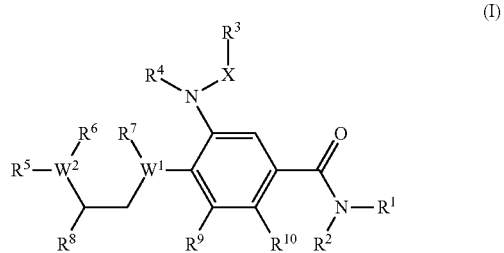

wherein $W^1$, $W^2$, $R^1$ to $R^{10}$ and X have the meaning according to the claims, are positive allosteric modulators of the FSH receptor, and can be employed, inter alia, for the treatment of fertility disorders.

17 Claims, No Drawings

BENZAMIDE DERIVATIVES AS MODULATORS OF THE FOLLICLE STIMULATING HORMONE

PRIORITY CLAIM

This application is a U.S. national stage application of PCT international application no. PCT/US2013/020802 filed on Jan. 9, 2013, which claims the benefit of U.S. Provisional application Ser. No. 61/585,077 filed on Jan. 10, 2012. The entire contents of the aforementioned applications are hereby incorporated by reference.

FIELD OF THE INVENTION

The present invention relates to compounds of formula (I)

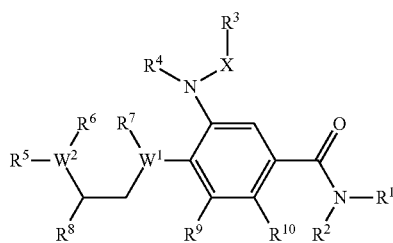

(I)

wherein $W^1$, $W^2$, $R^1$ to $R^{10}$ and X have the meaning according to the claims, and/or physiologically acceptable salts thereof. The compounds of formulas (I) can be used as positive allosteric modulators of the follicle stimulating hormone receptor (FSHR). Objects of the invention are also pharmaceutical compositions comprising the compounds of formula (I), and the use of the compounds of formula (I) for the treatment of fertility disorders.

BACKGROUND

Gonadotropins serve important functions in a variety of bodily functions including metabolism, temperature regulation and the reproductive process. Gonadotropins act on specific gonadal cell types to initiate ovarian and testicular differentiation and steroidogenesis. The gonadotropin FSH (follicle stimulating hormone) is released from the anterior pituitary under the influence of gonadotropin-releasing hormone and estrogens, and from the placenta during pregnancy. FSH is a heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. In the female, FSH plays a pivotal role in the stimulation of follicle development and maturation and in addition, it is the major hormone regulating secretion of estrogens, whereas LH induces ovulation. In the male, FSH is responsible for the integrity of the seminiferous tubules and acts on Sertoli cells to support gametogenesis.

The hormones are relatively large (28-38 kDa) and are composed of a common α-subunit non-covalently bound to a distinct β-subunit that confers receptor binding specificity. The cellular receptor for these hormones is expressed on testicular Sertoli cells and ovarian granulosa cells. The FSH receptor is known to be members of the G protein-coupled class of membrane-bound receptors, which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: a hydrophilic amino-terminal region, considered to be the amino-terminal extracellular domain; seven hydrophobic segments of membrane-spanning length, considered to be the transmembrane domain; and a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β-2-adrenergic, rhodopsin, and substance K receptors, by the large size of the hydrophilic amino-terminal domain, which is involved in hormone binding.

Annually in the U.S. there are 2.4 million couples experiencing infertility that are potential candidates for treatment. FSH, either extracted from urine or produced by recombinant DNA technology, is a parenterally-administered protein product used by specialists for ovulation induction and for controlled ovarial hyperstimulation. Whereas ovulation induction is directed at achieving a single follicle to ovulate, controlled ovarial hyperstimulation is directed at harvesting multiple oocytes for use in various in-vitro assisted reproductive technologies, e.g. in-vitro fertilization (IVF). FSH is also used clinically to treat male hypogonadism and male infertility, e.g. some types of failure of spermatogenesis.

FSHR is a highly specific target in the ovarian follicle growth process and is exclusively expressed in the ovary. However, the use of FSH is limited by its high cost, lack of oral dosing, and need of extensive monitoring by specialist physicians. Hence, identification of a non-peptidic small molecule substitute for FSH that could potentially be developed for oral administration is desirable. Low molecular weight FSH mimetics with agonistic properties are disclosed in the international applications WO 2002/09706 and WO 2010/136438 as well as the U.S. Pat. No. 6,653,338. Furthermore, WO 2009/105435 is directed to 3-(amido or sulphamido)-4-(4-substituted-azinyl)-benzamides which are useful as an inhibitor of the chemokine receptor CXCR3, and for preventing or treating a CXCR3-mediated disease, e.g. inflammation. There is still a need for low molecular weight hormone mimetics that selectively activate FSHR.

SUMMARY OF THE INVENTION

The invention had the object of finding novel compounds having valuable properties, in particular those which can be used for the preparation of medicaments.

It has been surprisingly found that the compounds according to the invention and salts thereof have very valuable pharmacological properties while being well tolerated. In particular, they act as FSHR agonists. The invention relates to compounds of formula (I)

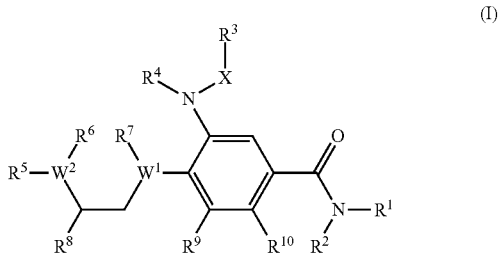

(I)

wherein
$W^1$, $W^2$ denote independently from one another N or CH, with the proviso that at least one of $W^1$ or $W^2$ denotes N;
$R^1$ denotes —(CY$_2$)$_n$-E-Het$^3$, —(CY$_2$)$_n$-Cyc-Het$^3$, —(CY$_2$)$_n$-Het$^1$, —(CY$_2$)$_n$—CONH-Het$^1$, —(CY$_2$)$_n$—

NHCO-Het¹, —(CY₂)ₙ—Ar, —(CY₂)ₙ-Cyc, —(CY₂)ₙ-Cyc-COOY, —(CY₂)ₙ—CONH-Cyc, —(CY₂)ₙ—NHCO-Cyc, A, —(CYR⁸)ₙ—OY, —(CY₂)ₙ—COOY, —(CY₂)ₙ—SO₂Y, —(CYR⁸)ₙ—CONY₂, —(CYR⁸)ₙ—NY₂, —(CYR⁸)ₙ—NYCOY, —(CY₂)ₙ—NYCOOY, —(CY₂)ₙ—NYCONY₂ or —(CY₂)ₙ—NHCO—CH═CH₂;

R¹, R² together also denote —(CY₂)ₚ—NH—(CY₂)ₚ—, —(CY₂)ₚ—NHCO—(CY₂)ₚ—, —(CY₂)ₚ—CONH—(CY₂)ₚ—, —(CY₂)ₚ—N(COA)-(CY₂)ₚ—, —(CY₂)ₚ—N(COOA)-(CY₂)ₚ—,

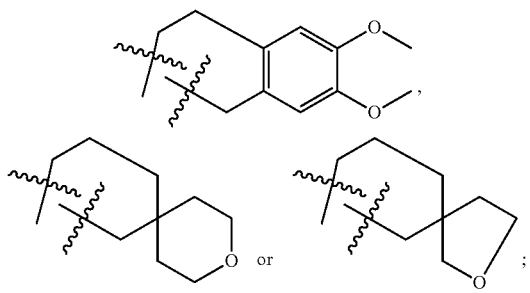

R³ denotes —(CY₂)ₙ-Het¹, —(CY₂)ₙ-Het³, —(CY₂)ₙ—Ar, H, A or —(CY₂)ₙ-Cyc;
R⁴, R⁹ denote independently from one another Y;
R⁵ denotes E-Ar, H, A, COOY, SO₂Y, Het¹ or Het³;
R², R⁶, R⁷ denote independently from one another H;
R⁶, R⁷ together also denote —(CY₂)ₚ—;
R⁸ denotes Y or Ar;
R¹⁰ denotes Hal, Y, OY, —O(CY₂)ₙ—OY, NY₂, Cyc, COOY, CONH₂, NHCOY or CN;
  with the proviso that it is excluded to simultaneously denote R⁹, R¹⁰ be H;
R², R¹⁰ together also denote —(CY₂)ₚ— or —(CY)₂—;
X, E denote independently from one another —(CY₂)ₘ—, O, CO, —COO— or SO₂;
Y denotes H or A;
A denotes unbranched or branched alkyl having 1-10 C atoms,
  in which 1-7 H atoms can be replaced independently from one another by Hal and/or ═O;
Cyc denotes cycloalkyl having 3-7 C atoms,
  in which 1-4 H atoms can be replaced independently from one another by Hal, OH or COOY;
Ar denotes an unsaturated or aromatic mono- or bicyclic carbocycle having 3-10 C atoms,
  which can be substituted by at least one substituent selected from the group of A, Hal, OY, COOY, CONH₂, NHCOY, —(CY₂)ₙ—NY₂, NO₂, SO₂Y, CN and Het², or which can be fused to Cyc;
Het¹ denotes an unsaturated or aromatic mono- or bicyclic heterocycle having 1-10 C atoms and 1-4 N, O and/or S atoms,
  which can be substituted by at least one substituent selected from the group of Hal, A, Cyc, OY, COOY, CONH₂, NHCOY, NY₂, SO₂Y, SO₂NY₂, NHSO₂Y, CN and Ar;
Het² denotes an unsaturated monocyclic 5-membered heterocycle having 1-3 C atoms and 2-4 N and/or S atoms,
  which can be substituted by A;
Het³ denotes a saturated mono- or bicyclic heterocycle having 3-7 C atoms and 1-4 N, O and/or S atoms,
  which can be substituted by at least one substituent selected from the group of ═O, A, Hal, —(CY₂)ₙ-Cyc, —(CY₂)ₙ—OY, COY, COOY, CONY₂, NHCOY, NY₂, CN, SO₂Y and —(CY₂)ₙ—Ar;
Hal denotes F, Cl, Br or I;
m, n denote independently from one another 0, 1, 2, 3, 4, 5 or 6; and
p denotes 1, 2 or 3;
and/or physiologically acceptable salts thereof.

For the sake of clarity, the fusion of Cyc to the carbocycle in the Ar definition refers to a condensed ring system, wherein another ring system is constructed on the mono- or bicyclic carbocycle with the result of a bi- or tricyclic carbocycle. Moreover, the disclaimer is valid for any embodiment of the invention described herein if appropriate.

It shall also be understood that R¹; R²; R¹⁰; R¹, R² together and R², R¹⁰ together have the indicated meaning with the proviso that (i) R¹, R² together and R², R¹⁰ together are absent if R¹; R² and R¹⁰ have the indicated meaning, (ii) R¹; R² and R², R¹⁰ together are absent if R¹, R² together and R¹⁰ have the indicated meaning, and (iii) R¹, R² together; R² and R¹⁰ are absent if R¹ and R², R¹⁰ together have the indicated meaning. The same shall apply mutatis mutandis for R⁶, R⁷ and R⁶, R⁷ together.

Either R⁹ or R¹⁰ can denote H, if any, but R⁹, R¹⁰ cannot denote H at the same time.

DETAILED DESCRIPTION OF THE INVENTION

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Y_2$ or YY) the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another. In case of a multiple substitution, the radical could be alternatively designated with R', R'', R''', R'''' etc.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, A denotes unbranched or branched alkyl having 1-10 C atoms, in which 1-7 H atoms may be replaced independently from one another by Hal and/or =O. A more preferred A denotes unbranched or branched alkyl having 1-6 C atoms, in which 1-4 atoms may be replaced independently from one another by Hal and/or =O. In a most preferred embodiment of the invention, A denotes unbranched or branched alkyl having 1-6 C atoms, in which 1-4 H atoms can be replaced independently from one another by Hal. It is highly preferred that A denotes unbranched or branched alkyl having 1-5 C atoms, in which 1-3 H atoms can be replaced independently from one another by F and/or Cl. Particularly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, Cyc denotes cycloalkyl having 3-7 C atoms, in which 1-4 H atoms may be replaced independently of one another by Hal, OH or COOY. More preferred is $C_3$-$C_6$-cycloalkyl, in which 1-3 H atoms may be replaced independently of one another by OH or COOY. Most preferred is $C_3$-$C_6$-cycloalkyl, in which 1-3 H atoms may be replaced independently of one another by OH or COOH. Highly preferred is $C_3$-$C_6$-cycloalkyl, in which 1-3 H atoms may be replaced independently of one another by OH. Particularly highly preferred is $C_3$-$C_6$-cycloalkyl, i.e. cyclopropyl, cyclobutyl, cyclopentyl or cyclohexyl. Moreover, the definition of A shall also comprise cycloalkyls and it is to be applied mutatis mutandis to Cyc. It shall be understood that the respective denotation of Cyc is independently of one another in any radical of the invention.

The term "aryl" or "carboaryl" for the purposes of this invention refers to a mono- or polycyclic aromatic hydrocarbon systems having 3 to 14, preferably 5 to 10, more preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suitable aryl radicals are phenyl, biphenyl, naphthyl, 1-naphthyl, 2-naphthyl and anthracenyl, but likewise in-danyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

In another embodiment of the invention, a carbocycle, including, but not limited to, carboaryl, is defined as "Ar". Examples of suitable Ar radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes an unsaturated or aromatic mono- or bicyclic carbocycle having 3-10 C atoms, which can be substituted by at least one substituent selected from the group of A, Hal, OY, COOY, $CONH_2$, NHCOY, $—(CY_2)_n—NY_2$, $NO_2$, $SO_2Y$, CN and $Het^2$, or which can be fused to Cyc. In a more preferred embodiment of the invention, Ar denotes an unsaturated or aromatic mono- or bicyclic carbocycle having 5-10 C atoms, which can be substituted by at least one substituent selected from the group of A, Hal, OY, COOY, $CONH_2$, NHCOY, $—(CY_2)_n—NY_2$, $NO_2$, CN and $Het^2$. It is most preferred that Ar denotes an aromatic monocyclic carbocycle having 6-8 C atoms, which can be mono- or disubstituted by at least one substituent selected from the group of A, Hal, OA, $CONH_2$, $—(CY_2)_n—NY_2$, $NO_2$ and CN. In a highly preferred embodiment of the invention, Ar denotes phenyl, which can be mono- or disubstituted by A, Hal or $—(CY_2)_n—NA_2$. Particularly preferred Ar is phenyl, which is monosubstituted by A. It shall be understood that the respective denotation of Ar is independently of one another in any radical of the invention.

The term "heteroaryl" for the purposes of this invention refers to a 1-15, preferably 1-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. Preferably, the number of nitrogen atoms is 0, 1, 2, 3 or 4, and that of the oxygen and sulfur atoms is independently from one another 0 or 1. The term "heteroaryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the heteroaryl radical. The bonding to the compounds of the general formula (I) can be effected via any possible ring member of the heteroaryl radical. Examples of suitable heteroaryl are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that heteroaryl in the realms of "$Het^1$" represents an unsaturated or aromatic mono- or bicyclic heterocycle having 1-10 C atoms and 1-4 N, O and/or S atoms, which can be substituted by at least one substituent selected from the group of Hal, A, Cyc, OY, COOY, $CONH_2$, NHCOY, $NY_2$, $SO_2Y$, $SO_2NY_2$, $NHSO_2Y$, CN and Ar. In a more preferred embodiment of the invention, $Het^1$ denotes an unsaturated or aromatic mono- or bicyclic heterocycle having 1-9 C atoms and 1-4 N, O and/or S atoms, which can be mono- or disubstituted by at least one substituent selected from the group of Hal, A, Cyc, OY, $CONH_2$, NHCOY, $NY_2$, $SO_2NY_2$, $NHSO_2Y$, CN and Ar. In another more preferred embodiment of the invention, $Het^1$ denotes an unsaturated or aromatic monocyclic heterocycle having 1-6 C atoms and 1-4 N, O and/or S atoms, which can be mono- or disubstituted by at least one substituent selected from the group of Hal, A, Cyc, OA, $CONH_2$, NHCOA, NHA, $SO_2NH_2$ and CN, or an aromatic bicyclic heterocycle having 6-9 C atoms and 1-3 N and/or S atoms, which can be monosubstituted by A. It is most preferred that $Het^1$ denotes pyrrolyl, furyl, thiophenyl, imidazolyl, pyrazyl, oxazyl, isoxazyl, thiazyl, thiadiazyl, tetrazyl, pyridyl, pyrimidyl, indolyl, benzimidazolyl, benzothiazyl, quinolyl, isoquinolyl or quinoxalyl, which can be monosubstituted by Hal, A or Cyc. Highly preferred $Het^1$ is furyl, oxazyl or tetrazyl, which can be monosubstituted by A or Cyc. It shall be understood that the respective denotation of $Het^1$ is independently of one another in any radical of the invention.

It is preferred that heteroaryl in the realms of "$Het^2$" represents an unsaturated monocyclic 5-membered heterocycle having 1-3 C atoms and 2-4 N and/or S atoms, which can be substituted by A. In a more preferred embodiment of the invention, $Het^2$ denotes imidazolyl, pyrazyl, thiazyl or tetrazyl, which can be monosubstituted by methyl.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated. In the case of a cyclic system consisting of at least two rings the rings may be fused or spiro or otherwise connected. Such heterocyclyl radicals can be linked via any ring member. The term "heterocyclyl" also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocyclyl radical. The bonding to the compounds of the general formula (I) can be effected via any possible ring member of the heterocyclyl radical. Examples of suitable heterocyclyl radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In a preferred aspect of the invention, the term "$Het^3$" denotes a saturated mono- or bicyclic heterocycle having 3-7 C atoms and 1-4 N, O and/or S atoms, which can be substituted by at least one substituent selected from the group of =O, A, Hal, $—(CY_2)_n$-Cyc, $—(CY_2)_n—OY$, COY, COOY, $CONY_2$, NHCOY, $NY_2$, CN, $SO_2Y$ and $—(CY_2)_n—Ar$. In a more preferred embodiment of the invention, $Het^3$ denotes a saturated monocyclic heterocycle having 3-6 C atoms and 1-3 N, O and/or S atoms, which can be mono-, di- or trisubstituted by at least one substituent selected from the group of =O, A, Hal, $—(CY_2)_n$-Cyc, $—(CY_2)_n—OY$, COY, COOY, $CONY_2$, NHCOY, $NY_2$, CN, $SO_2Y$ and $—(CY_2)_n—Ar$. In a most preferred embodiment of the invention, $Het^3$ denotes a saturated monocyclic heterocycle having 3-6 C atoms and 1-3 N, O and/or S atoms, which can be mono- or disubstituted by at least one substituent selected from the group of =O, A, Cyc, OY, COA, COOA, CONHA and SO$_2$A. It is highly preferred that Het$^3$ denotes pyrrolidinyl, oxolanyl, oxazolidinyl, imidazolidinyl, thiazolidinyl, piperidinyl, piperazinyl, thiomorpholinyl, which can be monosubstituted by =O. Particularly preferred Het$^3$ is pyrrolidinyl or oxazolidinyl, which is monosubstituted by =O. It shall be understood that the respective denotation of Het$^3$ is independently of one another in any radical of the invention.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, when the halogens are substituted on an alkyl (haloalkyl) or alkoxy group (e.g. CF$_3$ and CF$_3$O). It shall be understood that the respective denotation of Hal is independently of one another in any radical of the invention.

It is a preferred embodiment of the present invention that both W$^1$ and W$^2$ denote N.

It is a preferred embodiment of the R$^1$ radical according to the present invention to be —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc, —(CY$_2$)$_n$-Cyc-COOY, —(CY$_2$)$_n$—CONH-Cyc, A, —(CYR$^8$)$_n$—OY, —(CY$_2$)$_n$—COOY, —(CYR$^8$)$_n$—NY$_2$, —(CYR$^8$)$_n$—NYCOY, —(CY$_2$)$_n$—NY-COOY or —(CY$_2$)$_n$—NHCO—CH=CH$_2$, more preferably —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc, —(CY$_2$)$_n$—CONH-Cyc, A, —(CYR$^8$)$_n$—OH, —(CY$_2$)$_n$—COOA, —(CYR$^8$)$_n$—NY$_2$, —(CYR$^8$)$_n$—NACOA, —(CY$_2$)$_n$—NHCOOA or —(CY$_2$)$_n$—NHCO—CH=CH$_2$, most preferably —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc or —(CY$_2$)$_n$—CONH-Cyc, highly preferably —(CY$_2$)$_n$-E-Het$^3$, —(CY$_2$)$_n$—Ar or —(CY$_2$)$_n$-Cyc, particularly preferably —(CY$_2$)$_n$-Het$^3$ or —(CY$_2$)$_n$-Cyc.

It is a preferred embodiment of the R$^3$ radical according to the present invention to be Het$^1$, Het$^3$, Ar, H, A or Cyc, more preferably Het$^1$, Het$^3$ or Ar, most preferably Het$^1$ or Het$^3$, highly preferably Het$^1$.

It is a preferred embodiment of the R$^5$ radical according to the present invention to be E-Ar, H, A, COOA or Het$^1$, more preferably E-Ar or Het$^1$, most preferably Ar or Het$^1$, highly preferably Ar.

It is another highly preferred embodiment of the R$^1$, R$^3$, R$^5$ radicals according to the present invention to be independently from one another —(CY$_2$)$_n$-Het$^3$, —(CY$_2$)$_n$-Het$^1$, —(CY$_2$)$_n$—Ar or —(CY$_2$)$_n$-Cyc.

It is a preferred embodiment of the R$^6$, R$^7$ radicals according to the present invention to be together —(CY$_2$)$_p$—.

It is a preferred embodiment of the R$^8$ radical according to the present invention to be Y, more preferably H. It shall be understood that the respective denotation of R$^8$ is independently of one another in any radical of the invention.

It is a preferred embodiment of the R$^9$ radical according to the present invention to be H or CF$_3$, more preferably H.

It is a preferred embodiment of the R$^{10}$ radical according to the present invention to be Hal, Y, OY, —O(CY$_2$)$_n$—OY, NY$_2$, Cyc, COOY, CONH$_2$, NHCOY or CN, more preferably Hal, Y, OY, —O(CY$_2$)$_n$—OY, NY$_2$ or Cyc, most preferably Hal, A, OY, —O(CY$_2$)$_n$—OY, NY$_2$ or Cyc, highly preferably Hal, A, OA, —O(CY$_2$)$_n$—OA, NA$_2$ or Cyc, particularly preferably Hal or OA.

It is a preferred embodiment of the R$^2$, R$^{10}$ radicals according to the present invention to be together —(CY$_2$)$_2$— or —(CY)$_2$—, more preferably —(CH$_2$)$_2$— or —(CH)$_2$—, most preferably —(CH$_2$)$_2$—.

It is a preferred embodiment of the R$^2$, R$^9$, R$^{10}$ radicals according to the present invention that R$^2$, R$^9$ denote independently from one another H, and R$^{10}$ denotes Hal, A, OY, —O(CY$_2$)$_n$—OY, NY$_2$ or Cyc, or R$^2$, R$^{10}$ together denote —(CY$_2$)$_2$— or —(CY)$_2$—.

It is another more preferred embodiment of the R$^4$, R$^8$, R$^9$ radicals according to the present invention to be independently of one another H, more preferably to be H.

It is a preferred embodiment of the X radical according to the present invention to be CO, SO$_2$ or a single bond, more preferably CO or SO$_2$, most preferably CO.

It is a preferred embodiment of the E radical according to the present invention to be —(CY$_2$)$_m$—, CO, —COO— or SO$_2$, more preferably —(CY$_2$)$_m$—, CO or SO$_2$, most preferably —(CY$_2$)$_m$—. It shall be understood that the respective denotation of E is independently of one another in any radical of the invention.

In an aspect of the invention, Y denotes H or A. It shall be understood that the respective denotation of Y is independently of one another in any radical of the invention.

It is a preferred embodiment of the m index according to the present invention to be 0, 1, 2 or 3, more preferably 0, 1 or 2, most preferably 0 or 1.

It is a preferred embodiment of the n index according to the present invention to be 0, 1, 2, 3, 4 or 5, more preferably 0, 1, 2, 3 or 4, most preferably 0, 1, 2 or 3. It shall be understood that the respective denotation of n is independently of one another in any radical of the invention.

It is a preferred embodiment of the p index according to the present invention to be 1, 2 or 3, more preferably 2 or 3, most preferably 2. It shall be understood that the respective denotation of p is independently of one another in any radical of the invention.

In another preferred embodiment of the present invention, both W$^1$ and W$^2$ denote N, and R$^6$, R$^7$ together denote —(CY$_2$)$_p$—, and p denotes 2.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another preferred embodiment of the present invention, benzamide derivatives of sub-formula (I-A) are provided

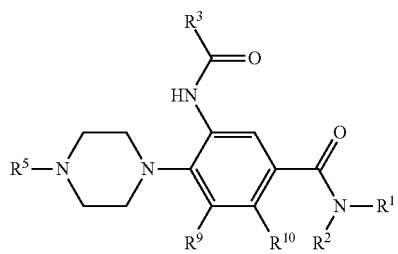

(I-A)

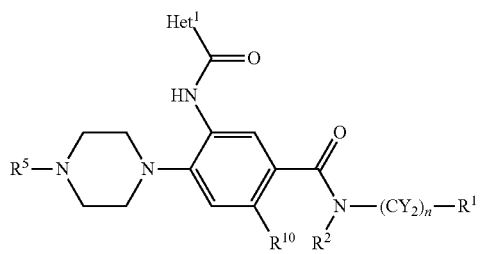

(I-B)

wherein

R¹ denotes —(CY$_2$)$_n$-E-Het³, —(CY$_2$)$_n$-Cyc-Het³, —(CY$_2$)$_n$-Het¹, —(CY$_2$)$_n$—NHCO-Het¹, —(CY$_2$)$_n$—Ar, —(CY$_2$)$_n$-Cyc, —(CY$_2$)$_n$—CONH-Cyc, A, —(CYR⁸)$_n$—OY, —(CY$_2$)$_n$—COOY, —(CYR⁸)$_n$—NY$_2$, —(CYR⁸)$_n$—NYCOY, —(CY$_2$)$_n$—NYCOOY or —(CY$_2$)$_n$—NHCO—CH═CH$_2$;

R² denotes H;

R³ denotes Het¹, Het³, Ar, H, A or Cyc;

R⁵ denotes E-Ar, H, A, COOA or Het¹;

R⁸, R⁹, Y denote independently from one another H or A;

R¹⁰ denotes Hal, Y, OY, —O(CY$_2$)$_n$—OY, NY$_2$ or Cyc;
  with the proviso that it is excluded to simultaneously denote R⁹, R¹⁰ be H;

R², R¹⁰ together also denote —(CY$_2$)$_p$— or —(CY)$_2$—;

E denotes —(CY$_2$)$_m$—, CO, —COO— or SO$_2$;

A denotes unbranched or branched alkyl having 1-10 C atoms, in which 1-7 H atoms can be replaced independently from one another by Hal and/or ═O;

Cyc denotes cycloalkyl having 3-7 C atoms, in which 1-4 H atoms can be replaced independently from one another by Hal, OH or COOY;

Ar denotes an unsaturated or aromatic mono- or bicyclic carbocycle having 5-10 C atoms, which can be substituted by at least one substituent selected from the group of A, Hal, OY, COOY, CONH$_2$, NHCOY, —(CY$_2$)$_n$—NY$_2$, NO$_2$, CN and Het²;

Het¹ denotes an unsaturated or aromatic mono- or bicyclic heterocycle having 1-9 C atoms and 1-4 N, O and/or S atoms, which can be mono- or disubstituted by at least one substituent selected from the group of Hal, A, Cyc, OY, CONH$_2$, NHCOY, NY$_2$, SO$_2$NY$_2$, NHSO$_2$Y, CN and Ar;

Het² denotes imidazolyl, pyrazyl, thiazyl or tetrazyl, which can be monosubstituted by methyl;

Het³ denotes a saturated monocyclic heterocycle having 3-6 C atoms and 1-3 N, O and/or S atoms, which can be mono-, di- or trisubstituted by at least one substituent selected from the group of ═O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar;

Hal denotes F, Cl, Br or I;

m, n denote independently from one another 0, 1, 2 or 3; and p denotes 2 or 3;

and/or physiologically acceptable salts thereof,

In another more preferred embodiment of the present invention, benzamide derivatives of sub-formula (I-B) are provided wherein R¹ denotes Het³, Het¹, Ar or Cyc;

R² denotes H;

R⁵ denotes Ar or Het¹;

R⁹ denotes H or CF$_3$;

R¹⁰ denotes Hal, Y, OY, —O(CY$_2$)$_n$—OY, NY$_2$ or Cyc;
  with the proviso that it is excluded to simultaneously denote R⁹, R¹⁰ be H;

R², R¹⁰ together also denote —(CY$_2$)$_2$— or —(CY)$_2$—;

Y denotes H or A;

A denotes unbranched or branched alkyl having 1-6 C atoms, in which 1-4 H atoms can be replaced independently from one another by Hal and/or ═O;

Cyc denotes cycloalkyl having 3-6 C atoms, in which 1-3 H atoms can be replaced independently from one another by OH or COOY;

Ar denotes an aromatic monocyclic carbocycle having 6-8 C atoms, which can be mono- or disubstituted by at least one substituent selected from the group of A, Hal, OA, CONH$_2$, —(CY$_2$)$_n$—NY$_2$, NO$_2$ and CN;

Het¹ denotes an unsaturated or aromatic monocyclic heterocycle having 1-6 C atoms and 1-4 N, O and/or S atoms, which can be mono- or disubstituted by at least one substituent selected from the group of Hal, A, Cyc, OA, CONH$_2$, NHCOA, NHA, SO$_2$NH$_2$ and CN, or an aromatic bicyclic heterocycle having 6-9 C atoms and 1-3 N and/or S atoms, which can be monosubstituted by A;

Het³ denotes a saturated monocyclic heterocycle having 3-6 C atoms and 1-3 N, O and/or S atoms, which can be mono- or disubstituted by at least one substituent selected from the group of ═O, A, Cyc, OY, COA, COOA, CONHA and SO$_2$A;

Hal denotes F, Cl, Br or I; and n denotes 0, 1, 2 or 3;

and/or physiologically acceptable salts thereof.

In another most preferred embodiment of the present invention, benzamide derivatives of sub-formula (I-C) are provided

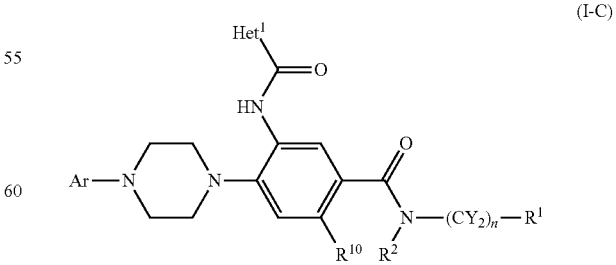

(I-C)

wherein

R¹ denotes Het³ or Cyc;

R² denotes H;

R¹⁰ denotes Hal, A, OA, —O(CY$_2$)$_n$—OA, NA$_2$ or Cyc;

$R^2$, $R^{10}$ together also denote —$(CH_2)_2$— or —$(CH)_2$—;

Y denotes H or A;

A denotes unbranched or branched alkyl having 1-6 C atoms, in which 1-4 H atoms can be replaced independently from one another by Hal;

Cyc denotes cycloalkyl having 3-6 C atoms, in which 1-3 H atoms can be replaced independently from one another by OH or COOH;

Ar denotes an aromatic monocyclic carbocycle having 6-8 C atoms, which can be mono- or disubstituted by A or Hal;

$Het^1$ denotes an unsaturated or aromatic monocyclic heterocycle having 1-6 C atoms and 1-3 N, O and/or S atoms, which can be mono- or disubstituted by at least one substituent selected from the group of Cyc, A or Hal;

$Het^3$ denotes a saturated monocyclic heterocycle having 3-6 C atoms and 1-3 N, O and/or S atoms, which can be mono- or disubstituted by at least one substituent selected from the group of =O, A or Hal;

Hal denotes F, Cl or Br; and n denotes 0, 1, 2 or 3;

and/or physiologically acceptable salts thereof.

The prior teaching of the present specification concerning the compounds of formula (I), including any radical definition and preferred embodiment thereof, is valid and applicable without restrictions to the compounds according to sub-formulae (I-A), (I-B), (I-C) and their salts if expedient.

Highly preferred embodiments are those compounds of formulae (I), (I-A), (I-B), (I-C) as listed in Table 1.

TABLE 1

| Compounds of formulae (I), (I-A), (I-B), (I-C). Assay A: Example 17; Assay B: Example 18. | | |
|---|---|---|
| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
| 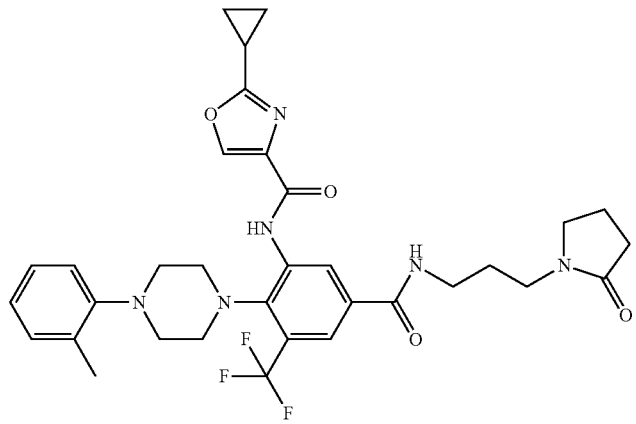 [SMILES: Cc1ccccc1N1CCN(c2c(NC(=O)c3coc(C4CC4)n3)cc(C(=O)NCCCN3CCCC3=O)cc2C(F)(F)F)CC1] | + | |
| 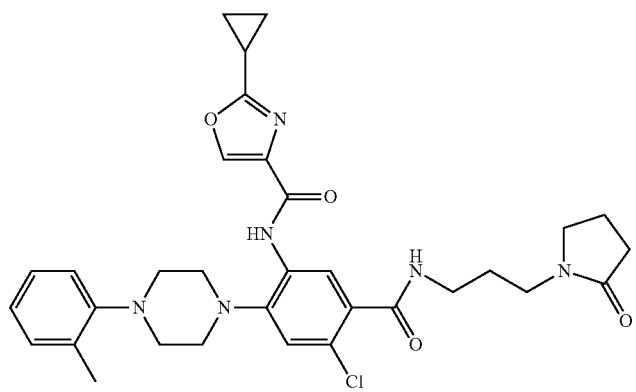 [SMILES: Cc1ccccc1N1CCN(c2cc(Cl)c(C(=O)NCCCN3CCCC3=O)cc2NC(=O)c2coc(C3CC3)n2)CC1] | +++ | ++ |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| *[structure: furan-2-carboxamide on benzene with 2-methylphenyl-piperazine, CF3, and N-(3-(2-oxopyrrolidin-1-yl)propyl)benzamide]* | 39% @ 3 μM | |
| *[structure: 2-cyclopropyloxazole-4-carboxamide on benzene with 2-methylphenyl-piperazine, OMe, and N-(3-(2-oxopyrrolidin-1-yl)propyl)benzamide]* | +++ | + |
| *[structure: 2-cyclopropyloxazole-4-carboxamide on benzene with 2-methylphenyl-piperazine, OH, and N-(3-(2-oxopyrrolidin-1-yl)propyl)benzamide]* | ++ | |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| [structure] | +++ | 133% @ 5 μM |
| [structure] | ++ | |
| [structure] | ++ | |

TABLE 1-continued
Compounds of formulae (I), (I-A), (I-B), (I-C). Assay A: Example 17; Assay B: Example 18.
| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| 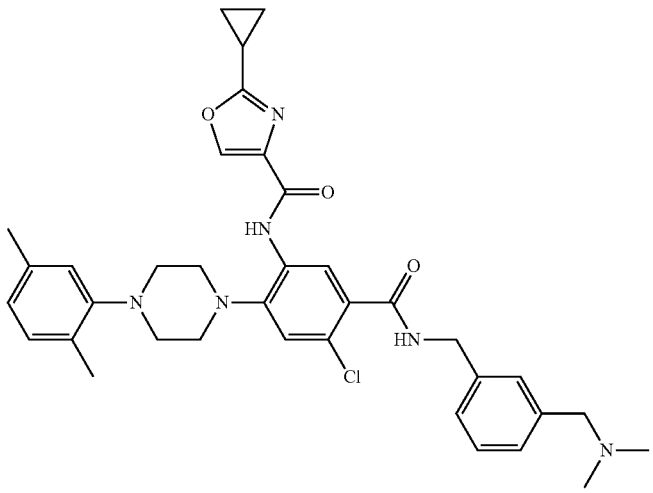 [SMILES: Cc1ccc(C)c(N2CCN(c3cc(Cl)c(C(=O)NCc4cccc(CN(C)C)c4)cc3NC(=O)c3coc(C4CC4)n3)CC2)c1] | + | |
| 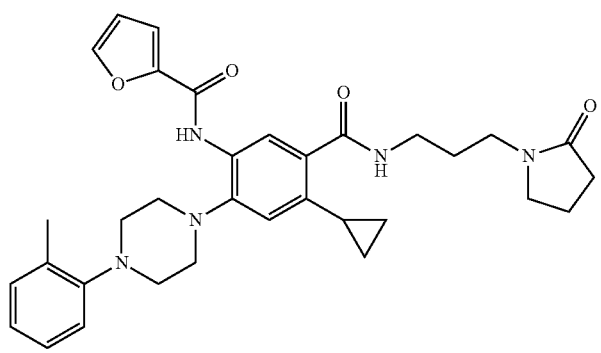 [SMILES: Cc1ccccc1N1CCN(c2cc(C3CC3)c(C(=O)NCCCN3CCCC3=O)cc2NC(=O)c2ccco2)CC1] | + | |
| 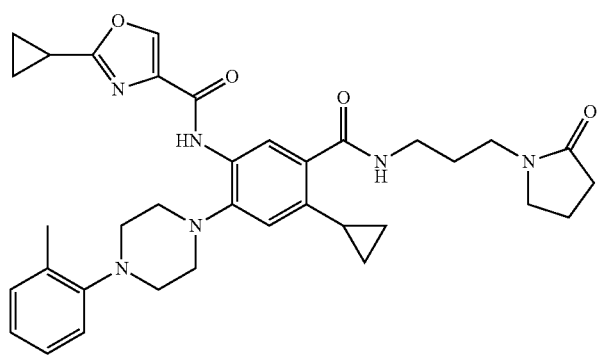 [SMILES: Cc1ccccc1N1CCN(c2cc(C3CC3)c(C(=O)NCCCN3CCCC3=O)cc2NC(=O)c2coc(C3CC3)n2)CC1] | ++ | |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| | ++ | ++ |
| 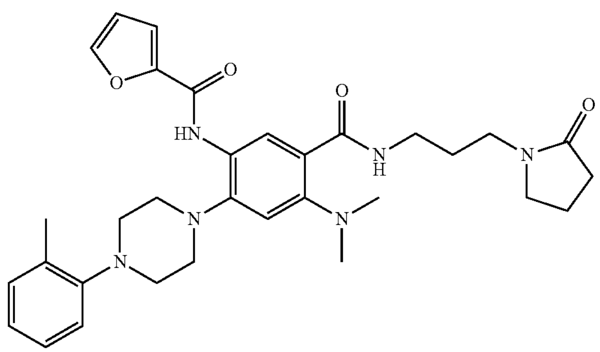 [SMILES: Cc1ccccc1N1CCN(c2cc(N(C)C)c(C(=O)NCCCN3CCCC3=O)cc2NC(=O)c2ccco2)CC1] | + | |
| | ++ | ++ |
| 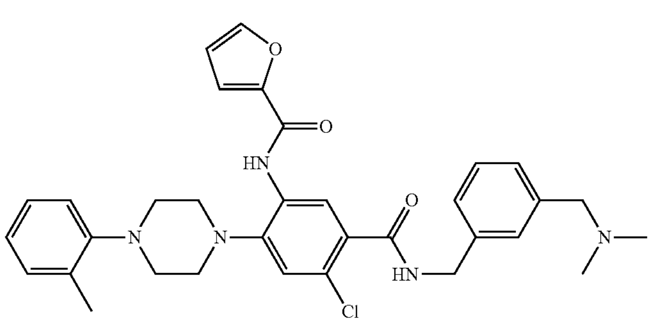 [SMILES: Cc1ccccc1N1CCN(c2cc(Cl)c(C(=O)NCc3cccc(CN(C)C)c3)cc2NC(=O)c2ccco2)CC1] | 0 | |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
| --- | --- | --- |
| | ++ | ++ |
| 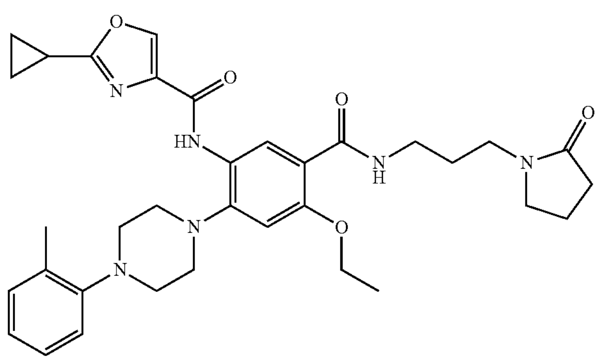 [SMILES: CCOc1cc(N2CCN(c3ccccc3C)CC2)c(NC(=O)c2coc(C3CC3)n2)cc1C(=O)NCCCN1CCCC1=O] | +++ | ++ |
| 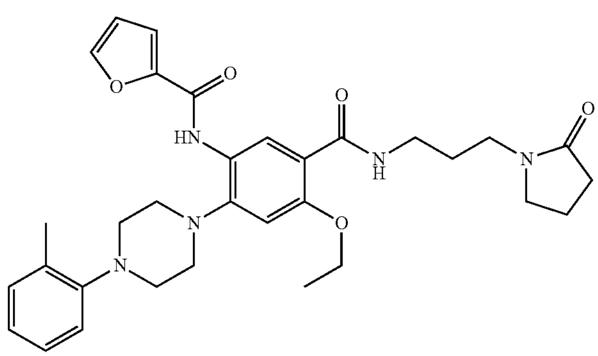 [SMILES: CCOc1cc(N2CCN(c3ccccc3C)CC2)c(NC(=O)c2ccco2)cc1C(=O)NCCCN1CCCC1=O] | + | |
| | ++ | |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| (structure) | +++ | ++ |
| (structure) | + | |
| (structure) | ++ | |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| (structure) | | ++ |
| (structure) | +++ | ++ |
| (structure) | + | |
| (structure) | ++ | + |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| (structure) | +++ | + |
| (structure) | ++ | ++ |
| (structure) | ++ | 46% @ 25 μM |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
| --- | --- | --- |
|  | ++ | + |
|  | ++ | 39% |
| 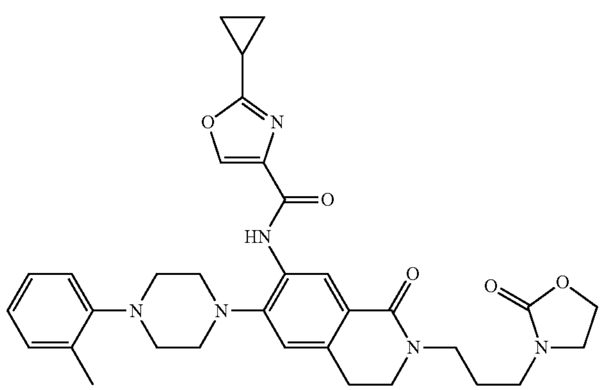 [SMILES: Cc1ccccc1N1CCN(c2cc3c(cc2NC(=O)c2coc(C4CC4)n2)C(=O)N(CCCN2CCOC2=O)CC3)CC1] | +++ | ++ |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
| --- | --- | --- |
| *[structure]* | ++ | + |
| *[structure]* | 0 | 11% |
| *[structure]* | ++ | +++ |

TABLE 1-continued

Compounds of formulae (I), (I-A), (I-B), (I-C). Assay A: Example 17; Assay B: Example 18.

| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| [structure] | +++ | |
| [structure] | ++ | |
| [structure] | +++ | |

TABLE 1-continued
Compounds of formulae (I), (I-A), (I-B), (I-C). Assay A: Example 17; Assay B: Example 18.
| Structure | Assay A<br>0 > 5 μM<br>+ > 1-5 μM<br>++ 0.1-1 μM<br>+++ < 0.1 μM | Assay B<br>0 > 5 μM<br>+ > 1-5 μM<br>++ 0.1-1 μM<br>+++ < 0.1 μM |
|---|---|---|
| 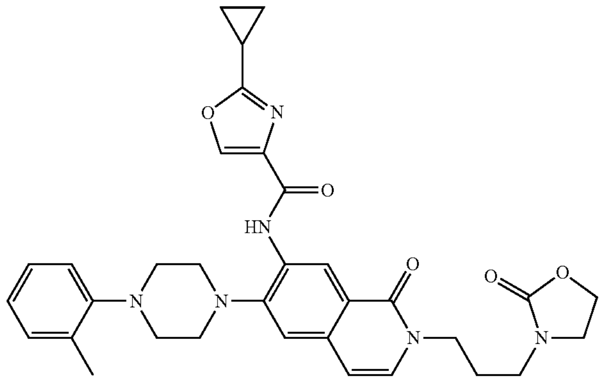 [SMILES: Cc1ccccc1N1CCN(c2cc3ccn(CCCN4CCOC4=O)c(=O)c3cc2NC(=O)c2coc(C3CC3)n2)CC1] | +++ | |
Particularly preferred embodiments are the compounds selected from the group of
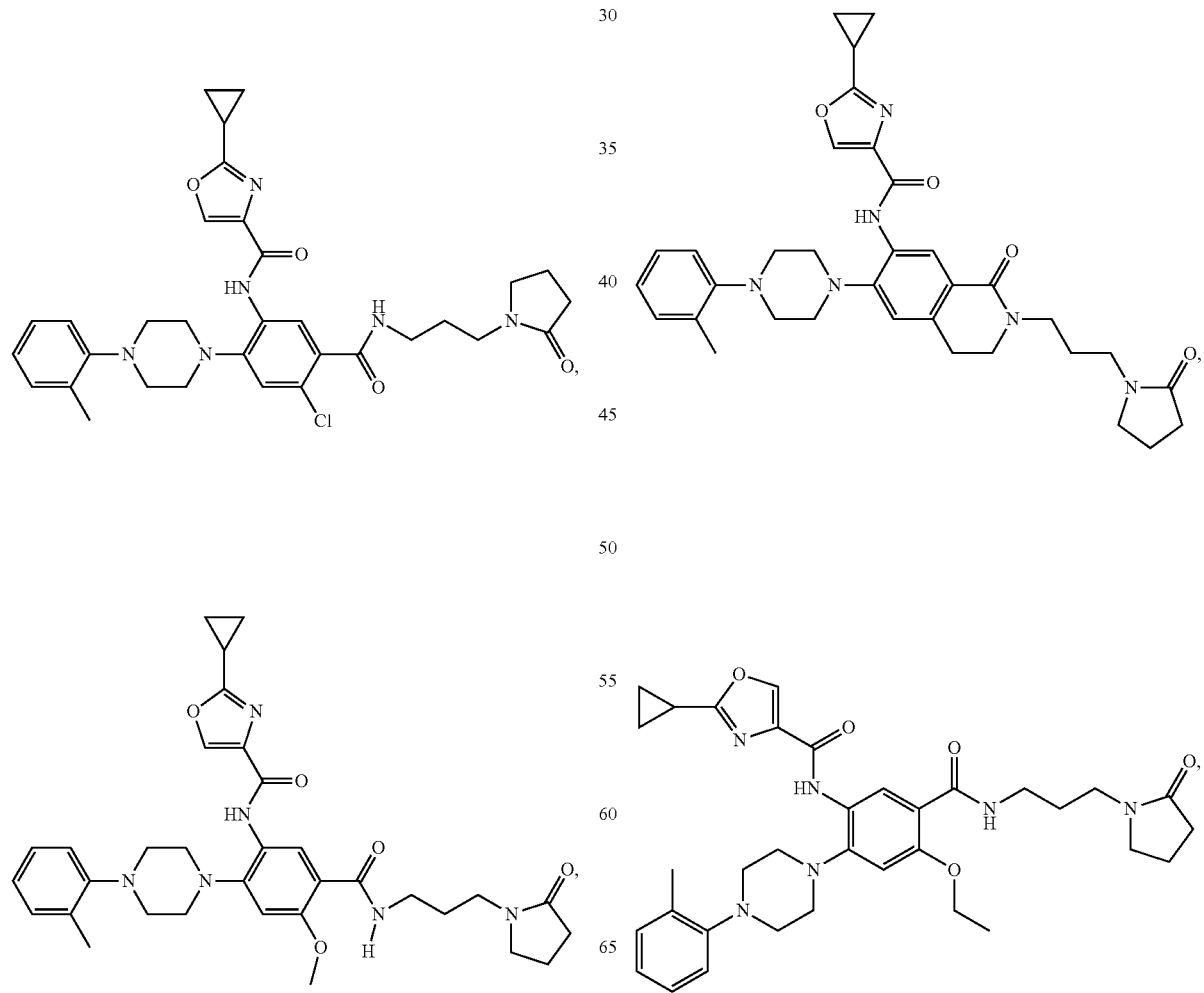

-continued

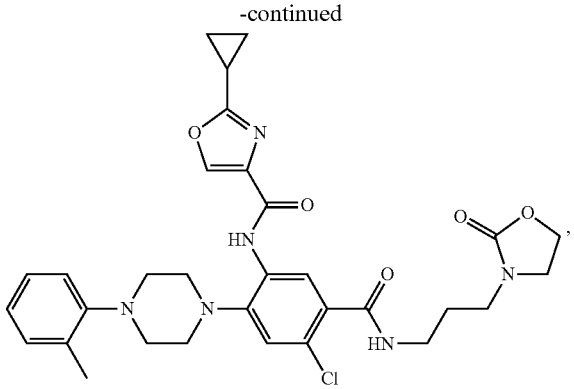

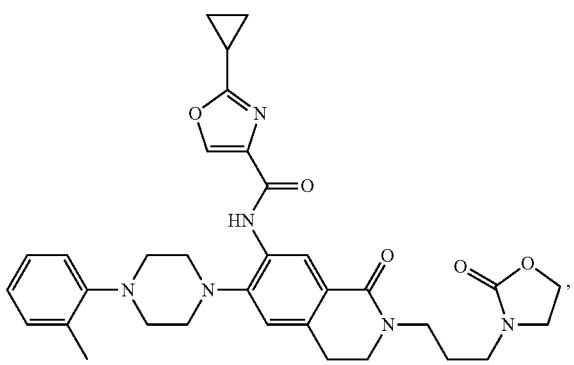

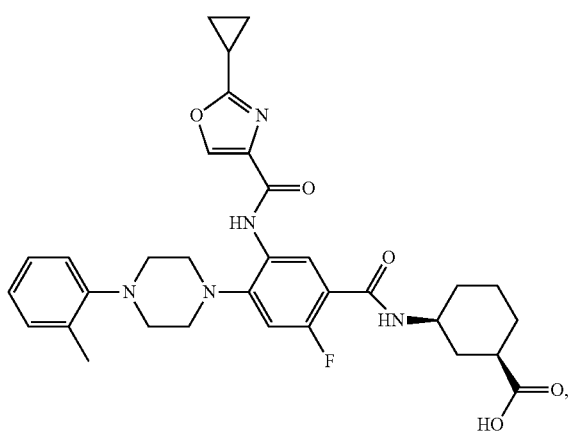

-continued

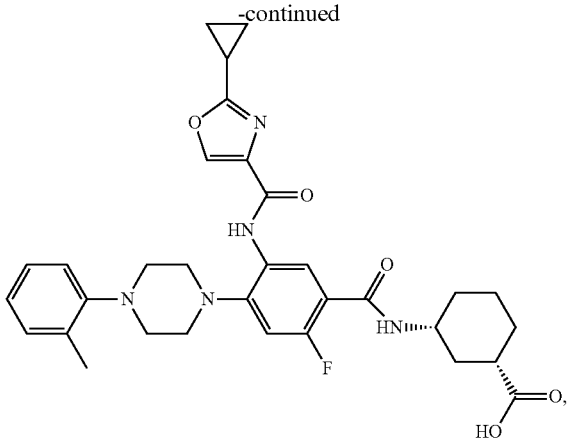

and/or physiologically acceptable salts thereof.

The benzamide derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert.-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to DMF, TFA, H$_2$O, THF, tert.-butanol, tert.-amylalcohol, triethylamine or dioxane.

Depending on the conditions used, the reaction time is between a few minutes and 14 days, the reaction temperature is between about −30° C. and 140° C., normally between −10° C. and 130° C., preferably between 30° C. and 125° C.

The present invention also relates to a process for manufacturing compounds of formula (I) comprising the steps of:
(a) reacting a compound of formula (II)

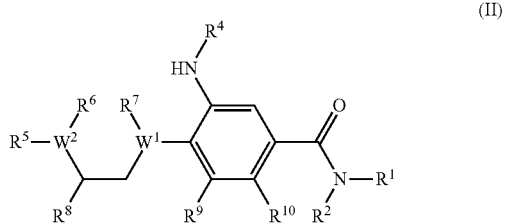

(II)

wherein W$^1$, W$^2$, R$^1$, R$^2$ and R$^4$ to R$^{10}$ have the meaning as defined above,
with a compound of formula (III)

(III)

wherein R$^3$ and X have the meaning as defined above,
to yield a compound of formula (I)

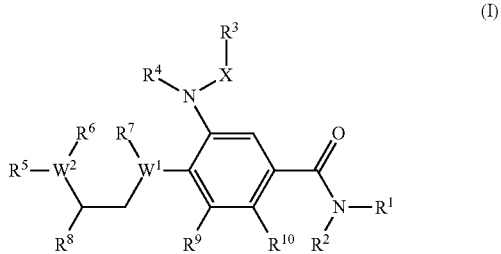

(I)

wherein W$^1$, W$^2$, R$^1$ to R$^{10}$ and X have the meaning as defined above,
and optionally
(b) converting a base or an acid of the compound of formula (I) into a salt thereof.

Object of the invention is also the provision of intermediate compounds of formula (II-A)

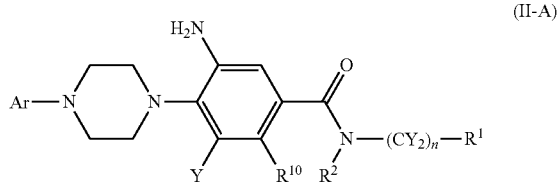

(II-A)

wherein
R$^1$ denotes Het$^3$ or Ar;
R$^2$ denotes H;
R$^{10}$ denotes Hal, A, OA, —O(CY$_2$)$_n$—OA, NA$_2$ or Cyc;
R$^2$, R$^{10}$ together also denote —(CH$_2$)$_2$— or —(CH)$_2$—;
Y denotes H or A;
A denotes unbranched or branched alkyl having 1-6 C atoms, in which 1-4 H atoms can be replaced independently from one another by Hal;

Cyc denotes cycloalkyl having 3-6 C atoms, in which 1-3 H atoms can be replaced independently from one another by OH;
Ar denotes an aromatic monocyclic carbocycle having 6-8 C atoms, which can be mono- or disubstituted by A, Hal or —(CY$_2$)$_n$—NY$_2$;
Het$^3$ denotes a saturated monocyclic heterocycle having 3-6 C atoms and 1-3 N, O and/or S atoms, which can be mono- or disubstituted by at least one substituent selected from the group of =O, A or Hal;
Hal denotes F, Cl or Br; and
n denotes 0, 1, 2 or 3.

A preferred intermediate of formula (II-A) is the following compound:

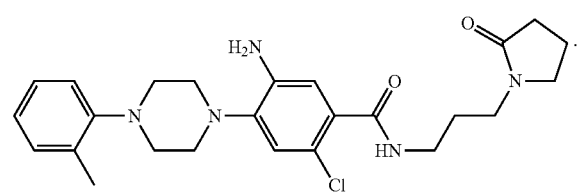 [SMILES: Cc1ccccc1N1CCN(c2cc(Cl)c(C(=O)NCCCN3CCCC3=O)cc2N)CC1]

The present invention also relates to another process for manufacturing compounds of formula (I) comprising the steps of:
(a) reacting a compound of formula (IV)

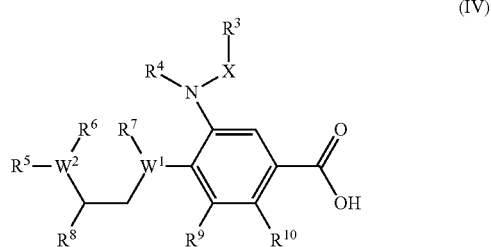

(IV)

wherein W$^1$, W$^2$, R$^3$ to R$^{10}$ and X have the meaning as defined above,
with a compound of formula (V)

(V)

wherein R$^1$ and R$^2$ have the meaning as defined above,
to yield a compound of formula (I)

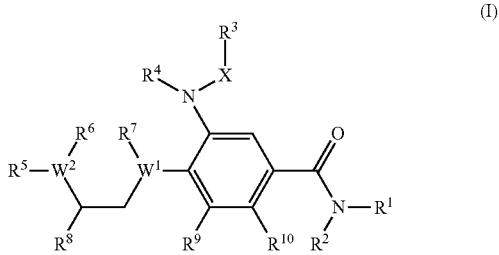

(I)

wherein W$^1$, W$^2$, R$^1$ to R$^{10}$ and X have the meaning as defined above,
and optionally
(b) converting a base or an acid of the compound of formula (I) into a salt thereof.

The benzamide derivatives of formula (I) are accessible via the route above. The starting materials, including the compounds of formulae (II), (III), (IV) and (V) are usually known to the skilled artisan, or they can be easily prepared by known methods. Accordingly, any compound of formulae (II), (III), (IV) and (V) can be purified, provided as intermediate product and used as starting material for the preparation of compounds of formula (I). The process step (a) is preferably performed in the presence of a crosslinking agent which is a carbodiimide derivative, particularly 1-ethyl-3-[3-dimethylaminopropyl]carbodiimide hydrochloride (EDC), and/or in the presence of a solvent, which is particularly DMF or an organic acid like TFA. It is more preferred in process step (a) to apply both EDC and TFA.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of PdO catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zink organyles (Negishi coupling) and tin organyles (Stille coupling) are useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (w2 as well as for O-arylation by using Cu catalysis and Pd catalysis.

In the final step of the processes above, a salt of the compounds according to formula (I) is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for modulating an FSH receptor, particularly in the presence of FSH. The term "modulation" denotes any change in FSHR-mediated signal transduction, which is based on the action of the specific inventive compounds capable to interact with the FSHR target in such a manner that makes recognition, binding and activating possible. The compounds are characterized by such a high affinity to FSHR, which ensures a reliable binding and preferably a positive allosteric modulation of FSHR. More preferably, the substances are mono-specific in order to guarantee an exclusive and directed recognition with the single FSHR target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

A preferred object of the present invention relates to a method for modulating an FSH receptor, preferably in a positive allosteric manner, wherein a system capable of expressing the FSH receptor, preferably expressing the FSH receptor, is contacted, preferably in the presence of FSH, with at least one compound of formula (I) according to the invention and/or physiologically acceptable salts thereof, under conditions such that said FSH receptor is modulated, preferably in a positive allosteric manner. Although a cellular system is preferred in the scope of the invention, an in-vitro translation system can be alternatively used which is based on the protein synthesis without living cells. The cellular system is defined to be any subject provided that the subject comprises cells. Hence, the cellular system can be selected from the group of single cells, cell cultures, tissues, organs and animals. The method for modulating an FSH receptor is preferably performed in-vitro. The prior teaching of the present specification concerning the compounds of formula (I), including any preferred embodiment thereof, is valid and applicable without restrictions to the compounds according to formula (I) and their salts when used in the method for modulating FSHR. The prior teaching of the present specification concerning the compounds of formula (I), including any preferred embodiment thereof, is valid and applicable without restrictions to the compounds according to formula (I) and their salts when used in the method for modulating FSHR.

The compounds according to the invention preferably exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect. It is preferred that the compounds of the invention have an FSHR agonist activity, as expressed by an $EC_{50}$ standard, of less than 5 µM, more preferably less than 1 µM, most preferably less than 0.5 µM, highly preferably less than 0.1 µM. "$EC_{50}$" is the effective concentration of a compound at which 50% of the maximal response of that obtained with FSH would be obtained.

As discussed herein, these signaling pathways are relevant for various diseases, preferably fertility disorders. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably agonists, more preferably positive allosteric modulators, of the signaling pathways described herein, preferably of the FSHR-mediated signaling pathway. The compounds of the invention are supposed to bind to the intracellular receptor domain without a competitive interaction with FSH, but they act as an allosteric enhancer of FSH on its receptor. The non-competitive interaction refers to the nature of the agonist activity exhibited by the compounds of the invention, wherein the compounds activate FSHR without substantially reducing the magnitude of binding of FSH to FSHR.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate FSHR activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing FSHR-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. The in-vitro use is preferably applied to samples of humans suffering from fertility disorders. Testing of several specific compounds and/or derivatives thereof makes the selection of that active ingredient possible that is best suited for the treatment of the human subject. The in-vivo dose rate of the chosen derivative is advantageously pre-adjusted to the FSHR susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the modulation of FSHR activity if expedient.

The invention furthermore relates to a medicament comprising at least one compound according to the invention and/or pharmaceutically usable derivatives, salts, solvates and stereoisomers thereof, including mixtures thereof in all ratios. Preferably, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or after-care of patients who suffer from diseases, which are associated with FSHR activity, in such a way that a pathogenic modification of their overall condition or of the condition of particular regions of the organism could establish at least temporarily.

Consequently, the invention also relates to a pharmaceutical composition comprising as active ingredient at least one compound of formula (I) according to the invention and/or physiologically acceptable salts thereof together with pharmaceutically tolerable adjuvants and/or excipients. It shall be understood that the compound of the invention is provided in an effective amount.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyitripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with known fertility-inducing agents. Preferably, the other active pharmaceutical ingredient is selected from the group of FSH, α-FSH (Gonal F), β-FSH, LH, hMG and 2-(4-(2-chloro-1,2-diphenylethenyl)-phenoxy)-N,N-diethyl-ethanamine citrate (Chlomifene citrate). Further ovulation adjuncts are known to those of skill in the art (cf. e.g. WO 2002/09706, which is incorporated herein by reference) and are useful with the compounds of the present invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient at least one compound of formula (I) according to the invention and/or physiologically acceptable salts thereof together with pharmaceutically tolerable adjuvants for oral administration, optionally in combination with at least another active pharmaceutical ingredient. Both active pharmaceutical ingredients are particularly provided in effective amount. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by FSHR activity. It is particularly preferred that the diseases are fertility disorders. It shall be understood that the host of the compound is included in the present scope of protection according to the present invention.

Particular preference is given to the stimulation of follicular development, ovulation induction, controlled ovarial hyperstimulation, assisted reproductive technology, including in-vitro fertilization, male hypogonadism and male infertility, including some types of failure of spermatogenesis.

The invention also relates to the use of compounds according to formula (I) and/or physiologically acceptable salts thereof for the prophylactic or therapeutic treatment and/or monitoring of diseases that are caused, mediated and/or propagated by FSHR activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by FSHR activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by FSHR activity. Another preferred object of the invention concerns compounds of formula (I) according to the invention and/or physiologically acceptable salts thereof for use in the prophylactic or therapeutic treatment and/or monitoring of fertility disorders. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of fertility disorders.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with FSHR activity in advance or to treat the arising and continuing symptoms. The disorders as concerned by the invention are preferably fertility disorders.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by FSHR activity, wherein at least one compound of formula (I) according to the invention and/or physiologically acceptable salts thereof is administered to a mammal in need of such treatment. It is another preferred object of the invention to provide a method for treating fertility disorders, wherein at least one compound of formula (I) according to the invention and/or physiologically acceptable salts thereof is administered to a mammal in need of such treatment. The compound is preferably provided in an effective amount as defined above. The preferred treatment is an oral administration. In another preferred aspect, the method of treatment aims to achieve ovulation induction and/or controlled ovarian hyperstimulation. In still another preferred aspect, the method of treatment forms the basis for a method for in-vitro fertilization comprising the steps of: (a) treating a mammal according to the method of treatment as described above, (b) collecting ova from said mammal, (c) fertilizing said ova, and (d) implanting said fertilized ova into a host mammal. The host mammal can be either the treated mammal (i.e. the patient) or a surrogate. The prior teaching of the invention and its embodiments is valid and applicable without restrictions to the methods of treatment if expedient.

In the scope of the present invention, novel benzamide compounds of formula (I) are provided for the first time. The low molecular weight compounds of the invention are strong and selective modulators of the FSH receptor. Their selectivity to the FSH receptor is 10-fold over the LH receptor and even 100-fold over the TSH receptor while the $IC_{50}$ amounts to more than 10 µM on unrelated G protein-coupled receptors (GPCR) or non-GPCR targets. The current invention comprises the use of present benzamide derivatives in the regulation and/or modulation of the FSHR signal cascade, which can be advantageously applied as research tool, for diagnosis and/or in treatment of any disorder arising from FSHR signaling.

For example, the compounds of the invention are useful in-vitro as unique tools for understanding the biological role of FSH, including the evaluation of the many factors thought to influence, and be influenced by, the production of FSH and the interaction of FSH with the FSHR (e. g. the mechanism of FSH signal transduction/receptor activation). The present compounds are also useful in the development of other compounds that interact with FSHR since the present compounds provide important structure-activity relationship (SAR) information that facilitate that development. Compounds of the present invention that bind to FSHR can be used as reagents for detecting FSHR on living cells, fixed cells, in biological fluids, in tissue homogenates, in purified, natural biological materials, etc. For example, by labeling such compounds, one can identify cells having FSHR on their surfaces. In addition, based on their ability to bind FSHR, compounds of the present invention can be used in in-situ staining, FACS (fluorescence-activated cell sorting), western blotting, ELISA (enzyme-linked immunoadsorptive assay), etc., receptor purification, or in purifying cells expressing FSHR on the cell surface or inside permeabilized cells.

The compounds of the invention can also be utilized as commercial research reagents for various medical research and diagnostic uses. Such uses can include but are not limited to: use as a calibration standard for quantifying the activities of candidate FSH agonists in a variety of functional assays; use as blocking reagents in random compound screening, i.e. in looking for new families of FSH receptor ligands, the compounds can be used to block recovery of the presently claimed FSH compounds; use in the co-crystallization with FSHR receptor, i.e. the compounds of the present invention will allow formation of crystals of the compound bound to FSHR, enabling the determination of receptor/compound structure by x-ray crystallography; other research and diagnostic applications, wherein FSHR is preferably activated or such activation is conveniently calibrated against a known quantity of an FSH agonist, etc.; use in assays as probes for determining the expression of FSHR on the surface of cells; and developing assays for detecting compounds which bind to the same site as the FSHR binding ligands.

The low molecular weight inhibitors can be applied either themselves and/or in combination with physical measurements for diagnostics of treatment effectiveness. Medicaments and pharmaceutical compositions containing said compounds and the use of said compounds to treat FSHR-mediated conditions is a promising, novel approach for a broad spectrum of therapies causing a direct and immediate improvement in the state of health, whether in man and animal. The impact is of special benefit to efficiently combat infertility, either alone or in combination with other fertility-inducing treatments. In particular, the compounds of the invention potentiate the native FSH effect for both ovulation induction and assisted reproductive technology. The orally bioavailable and active new chemical entities of the invention improve convenience for patients and compliance for physicians.

The compounds of the invention are active in the primary screen (CHO with or without FSH), selective in secondary screen (no or low activity against TSHR and LHR) and potent in the granulosa cell estrodiol assay. Neither hERG nor any toxic effects could be observed in-vitro.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

It is to be understood that this invention is not limited to the particular compounds, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved. Similarly, the features of any claim can be combined with the features of one or more other claims.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.
Standard Description of Analytical Equipment NMR Spectra were acquired on a Varian $^{Unity}$Inova 400 MHz NMR spectrometer equipped with an Automation Triple Broadband (ATB) probe. The ATB probe was simultaneously tuned to $^1$H, $^{19}$F and $^{13}$C. For typical $^1$H NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to second. Spectra were collected at 25° C. $^1$H NMR Spectra are typically processed with 0.2 Hz line broadening and zero-filling to 131072 points prior to Fourier transformation.

Method A (Rapid LC): A Shimadzu Shim-pack XR-ODS, 3.0×30 mm, 2.2 µm, was used at a temperature of 50° C. and at a flow rate of 1.5 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient, (II) hold for 0.8 min at 95% (B), (III) decrease from 95-15% (B) in a 0.1 min linear gradient, and (IV) hold for 0.29 min at 15% (B).

Method B (Polar Stop-Gap): An Agilent Zorbax Bonus RP, 2.1×50 mm, 3.5 µm, was used at a temperature of 50° C. and at a flow rate of 0.8 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient, (II) hold for 0.5 min at 95% (B), (III) decrease from 95-5% (B) in a 0.1 min linear gradient, and (IV) hold for 0.29 min at 5% (B).

Preparative HPLC was performed using a system controlled by Chromeleon software and consisting of two Varian PrepStar Model 218 Pumps, a Varian ProStar Model 320 UV/Vis detector, a SEDEX 55 ELSD detector, and a Gilson 215 liquid handler. Typical HPLC mobile phases consist of water and methanol. The standard column is a Varian Dynamax 21.4 mm diameter Microsorb Guard-8 C18 column.

EXAMPLE 1

Synthetic route towards 2-cyclopropyl-oxazole-4-carboxylic acid [4-chloro-5-[3-(2-oxo-pyrrolidin-1-yl)propylcarbamoyl]-2-(4-o-tolyl-piperazin-1-yl)-phenyl]-amide (1i)

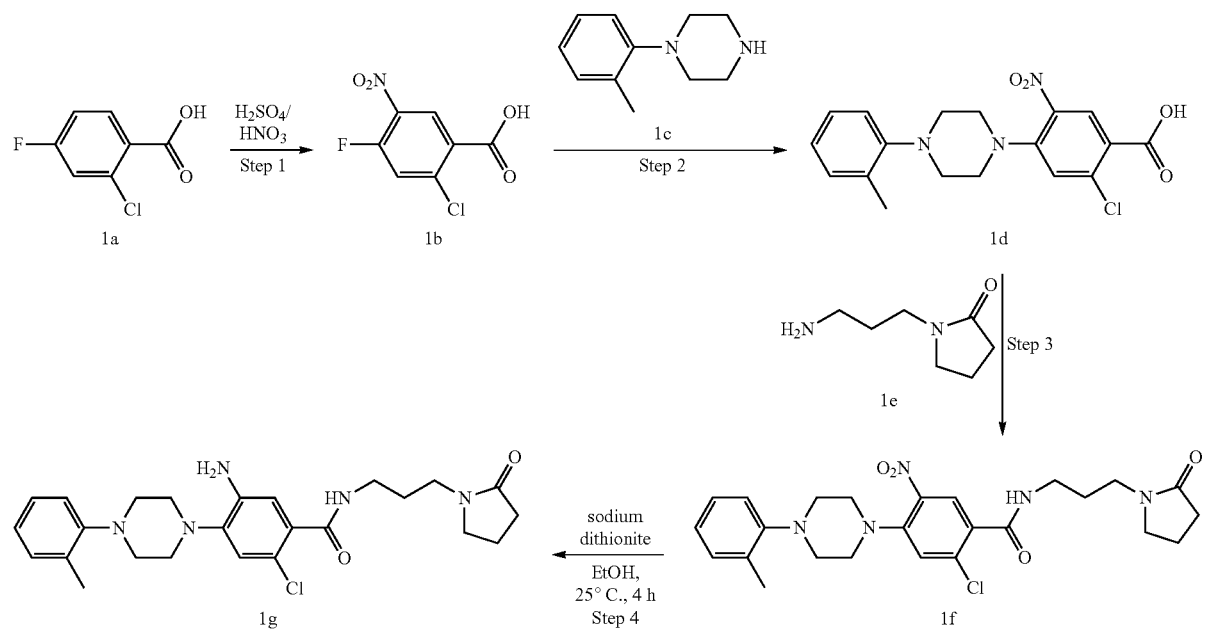

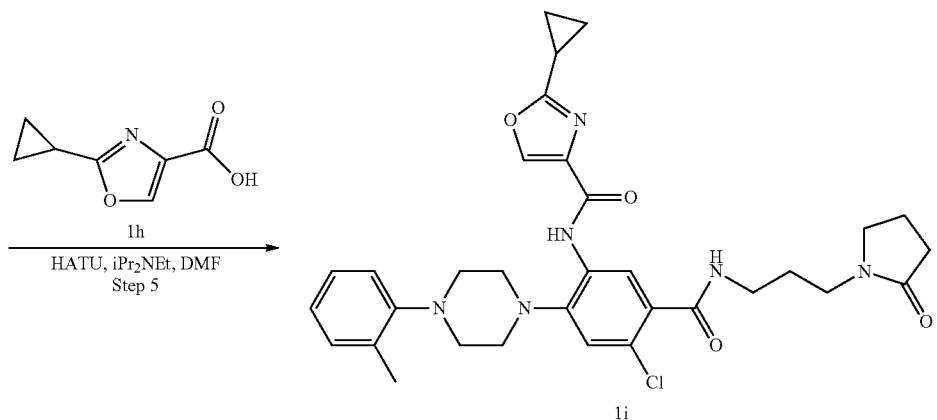

Step 1: 2-Chloro-4-fluoro-benzoic acid 1a (5.0 g, 28.64 mmol) was taken in sulphuric acid (20.0 mL) and cooled to 0° C. Nitric acid (10.0 ml) was added to this very carefully and slowly. The reaction was stirred at 0-25° C. for 6 h. The white solid was filtered and washed with water and dried at 40° C. under vacuum and used in the next step.

Step 2: To a solution of 2-chloro-4-fluoro-5-nitro-benzoic acid 1b (2.0 g, 9.1 mmol) in DMF (20.0 mL) was added potassium carbonate (2.51 g, 18.21 mmol) slowly followed by 1-o-tolyl-piperazine 1e (1.9 g, 10.93 mmol) and the reaction was stirred at room temperature for 16 h. Water was added carefully and the solution was acidified to pH 5.0 using 1N HCl to give yellow solid which was filtered and dried.

Step 3: To a solution of 2-chloro-5-nitro-4-(4-o-tolyl-piperazin-1-yl)-benzoic acid 1d (1.0 g, 2.6 mmol) in DMF was added HATU (2.0 g, 5.32 mmol) and stirred for 4 min. N,N-diisopropylethylamine (2.3 mL, 13.30 mmol) was added to this and the solution was stirred for another 4 min. 1-(3-Amino-propyl)-pyrrolidin-2-one 1e (0.56 ml, 3.99 mmol) was added to this and the reaction was stirred at room temperature for 16 h. A saturated solution of lithium chloride was added and extracted with ethyl acetate. Organic layer was washed with brine and dried on anhydrous sodium sulfate, concentrated and crude 1f was taken to next step.

Step 4: 2-Chloro-5-nitro-N-[3-(2-oxo-pyrrolidin-1-yl)-propyl]-4-(4-o-tolyl-piperazin-1-yl)-benzamide 1f (0.7 g, 1.40 mmol) was taken in ethanol (20.0 mL). Sodium dithionite (0.98 g, 5.6 mmol) was dissolved in water (10.0 ml) and added to this. The reaction was stirred at 45° C. for 6 h. Cooled and ethanol was rotavaped out. Crude 1 g was extracted with dichloromethane and concentrated and this was purified on silica gel using dichloromethane/MeOH (10%) (376 mg, 57%).

Step 5: To a solution of 2-cyclopropyl-oxazole-4-carboxylic acid 1h (122.2 mg, 0.79 mmol) in DMF (5.0 mL) HATU (404.4 mg, 1.06 mmol) was added and stirred for 3 min. N,N-diisopropylethylamine (0.46 mL, 2.66 mmol) was added to this followed by 5-amino-2-chloro-N-[3-(2-oxo-pyrrolidin-1-yl)-propyl]-4-(4-o-tolyl-piperazin-1-yl)-benzamide 1g (250.0 mg, 0.53 mmol) in DMF (5.0 mL) and the reaction was stirred at 25° C. for 16 h. LCMS indicated the completion of reaction. Saturated solution of lithium chloride was added to this and the contents were extracted with ethyl acetate, organic layer was dried on anhydrous sodium sulfate, concentrated and the crude ii was purified on preparative HPLC using water/methanol (0.1% TFA) (42.0 mg, 13%).

LCMS (ESI) 605 (M+H);

$^1$H NMR (400 MHz, METHANOL-$d_4$) δ ppm 1.00-1.14 (m, 4H) 1.76-1.90 (m, 2H) 1.99-2.18 (m, 3H) 2.31-2.41 (m, 5H) 3.02-3.13 (m, 3H) 3.17-3.23 (m, 4H) 3.32-3.42 (m, 4H) 3.50 (t, J=7.08 Hz, 2H) 6.88-7.06 (m, 2H) 7.11-7.25 (m, 3H) 8.31 (s, 1H) 8.52 (s, 1H).

EXAMPLE 2A

Synthetic route towards 2-cyclopropyl-oxazole-4-carboxylic acid [4-methoxy-5-[3-(2-oxo-pyrrolidin-1-yl)-propylcarbamoyl]-2-(4-o-tolyl-piperazin-1-yl)-phenyl]-amide 2c

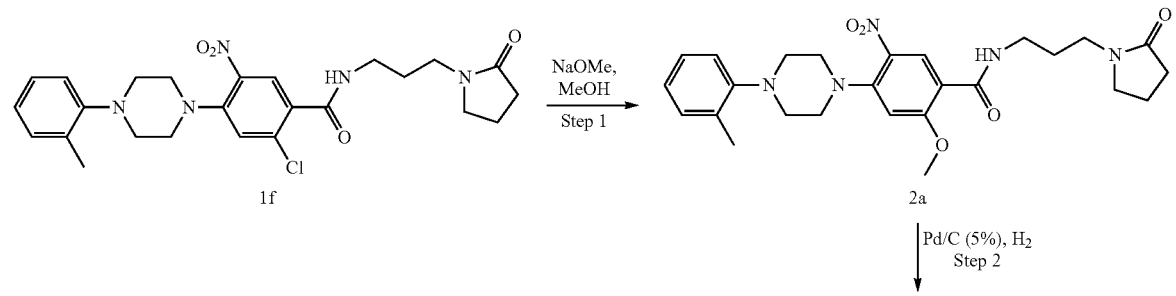

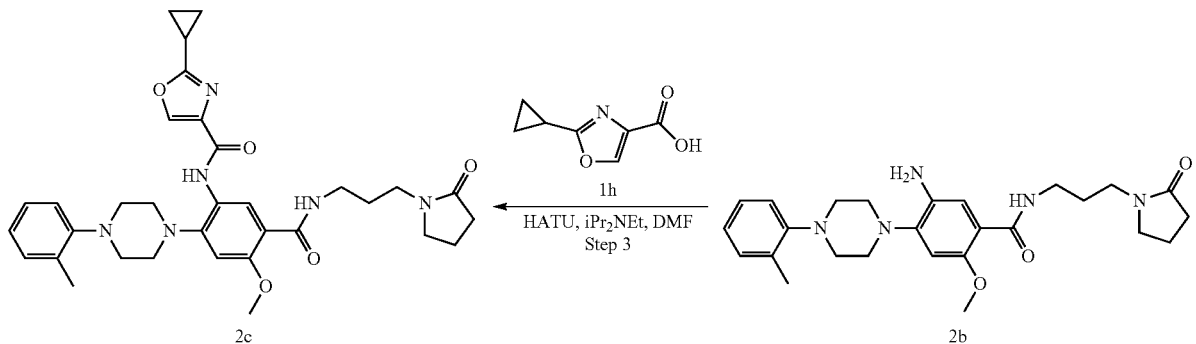

Step 1: To a solution of 2-chloro-5-nitro-N-[3-(2-oxo-pyrrolidin-1-yl)-propyl]-4-(4-o-tolyl-piperazin-1-yl)-benzamide 1f (350.0 mg, 0.70 mmol) in methanol (10.0 ml) was added sodium methoxide (378.1 mg, 7.0 mmol) and the reaction was stirred at 45° C. for 6 h. The reactions mixture was concentrated, water was added carefully and extracted with ethyl acetate. Organic layer was washed with water and brine and concentrated. Crude 2a was purified on silica gel using dichloromethane/MeOH (10%) to give product (248 mg, 71%).

Step 2: 2-Methoxy-5-nitro-N-[3-(2-oxo-pyrrolidin-1-yl)-propyl]-4-(4-o-tolyl-piperazin-1-yl)-benzamide 2a (350.0 mg, 0.706 mmol) was taken in ethanol and evacuated and nitrogen purged. This was added to a flask containing Pd/C (5 wt %) (300.6 mg, 0.141 mmol) under nitrogen. Flask was evacuated again and reaction was stirred under hydrogen balloon for 4 h. Hydrogen was removed and the reaction was evacuated and nitrogen purged. The content was filtered over Celite and concentrated to give crude product 2b which was taken to next step.

Step 3: 2-Cyclopropyl-oxazole-4-carboxylic acid 1h (74.8 mg, 0.489 mmol) was taken in DMF (5.0 ml) and HATU (212.3 mg, 0.558 mmol) was added to this and stirred for 3 min. N,N-diisopropylethylamine (0.243 mL, 1.396 mmol) was added to this and the mixture was stirred again for 3 min. 5-Amino-2-methoxy-N-[3-(2-oxo-pyrrolidin-1-yl)-propyl]-4-(4-o-tolyl-piperazin-1-yl)-benzamide 2b (130.0 mg, 0.279 mmol) was added and the reaction mixture was stirred at room temperature for 16 h. A saturated solution of lithium chloride was added and the product was extracted with ethyl acetate. Organic layer was washed with brine and dried over anhydrous sodium sulfate and concentrated to give the crude product 2c which was purified on preparative HPLC using water/methanol as eluent.

LCMS (ESI) 601 (M+H);

$^1$H NMR (400 MHz, METHANOL-$d_4$) δ ppm 1.08-1.13 (m, 4H) 1.80 (t, J=6.54 Hz, 2H) 1.99-2.18 (m, 3H) 2.34 (s, 3H) 2.35-2.41 (m, 2H) 3.12-3.17 (m, 8H) 3.33-3.42 (m, 4H) 3.47 (t, J=7.13 Hz, 2H) 4.01 (s, 3H) 6.79-7.05 (m, 2H) 7.09-7.30 (m, 3H) 8.27 (s, 1H) 8.88 (s, 1H).

EXAMPLE 2B

Synthetic route towards 2-cyclopropyl-oxazole-4-carboxylic acid [4-hydroxy-5-[3-(2-oxo-pyrrolidin-1-yl)-propylcarbamoyl]-2-(4-o-tolyl-piperazin-1-yl)-phenyl]-amide 2d

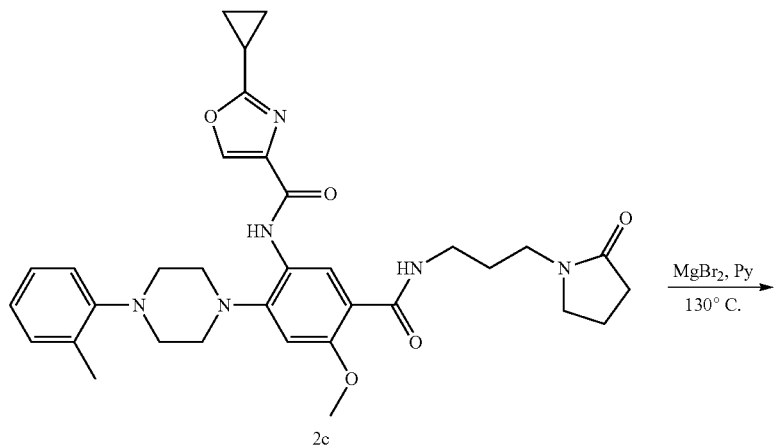

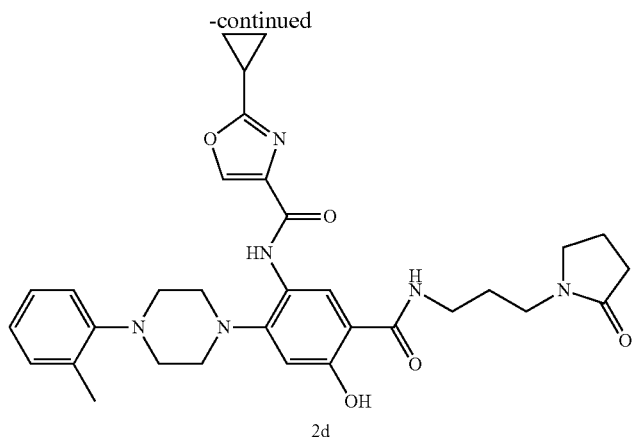

To a solution of 2-cyclopropyl-oxazole-4-carboxylic acid [4-methoxy-5-[3-(2-oxo-pyrrolidin-1-yl)-propylcarbamoyl]-2-(4-o-tolyl-piperazin-1-yl)-phenyl]-amide 2c (40.0 mg, 0.067 mmol) in pyridine (5.0 mL) was added magnesium bromide (49.0 mg, 0.268 mmol). The reaction was stirred at 130° C. for 16 h. Cooled, concentrated and the crude 2d was dissolved in methanol/water mixture and purified on preparative HPLC using methanol/water as eluent.

LCMS (ESI) 587 (M+H);
$^1$H NMR (400 MHz, DICHLOROMETHANE-$d_2$) δ ppm 1.14 (d, J=2.34 Hz, 4H) 1.70-1.85 (m, 2H) 2.00-2.14 (m, 3H) 2.34 (s, 3H) 2.42 (d, J=8.30 Hz, 2H) 3.04-3.19 (m, 8H) 3.31-3.45 (m, 4H) 6.76 (s, 1H) 6.92-7.04 (m, 1H) 7.18 (d, J=13.42 Hz, 3H) 7.85-7.99 (m, 1H) 8.10 (s, 1H) 8.70 (s, 1H) 9.41-9.60 (m, 1H) 12.83 (s, 1H).

EXAMPLE 3

Synthetic route towards 2-cyclopropyl-oxazole-4-carboxylic acid [4-fluoro-5-[3-(2-oxo-pyrrolidin-1-yl)-propylcarbamoyl]-2-(4-o-tolyl-piperazin-1-yl)-phenyl]-amide 3c

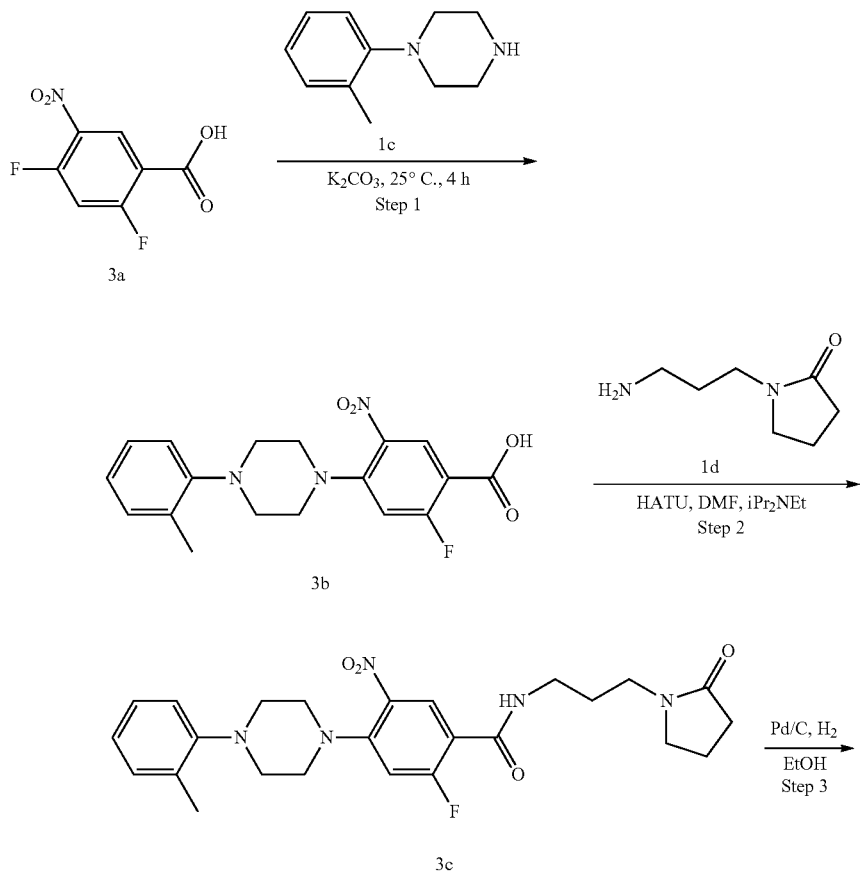

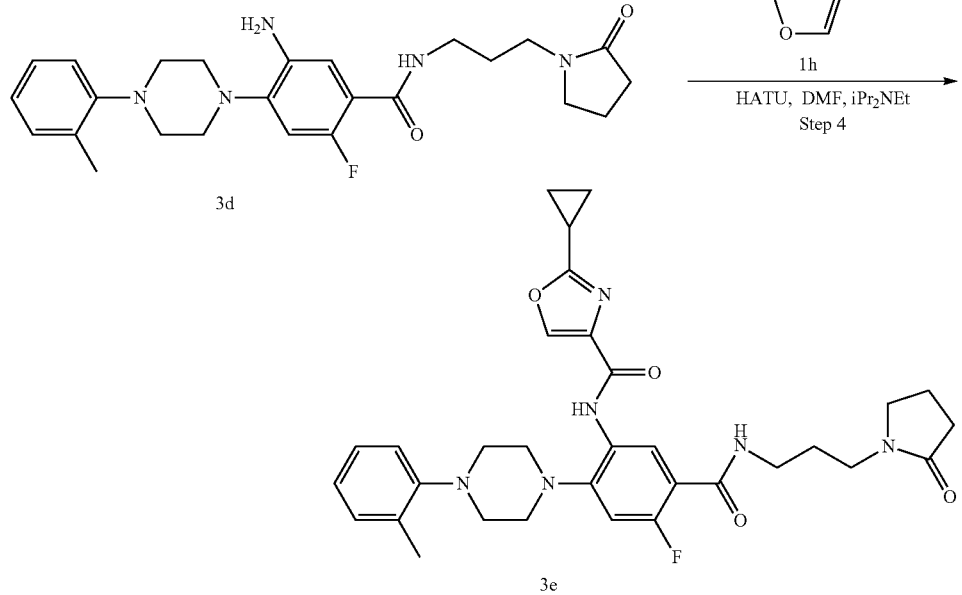

Step 1: 2,4-Difluoro-5-nitro-benzoic acid 3a (1.0 g, 4.9 mmol) was taken in DMF (20 ml) and potassium carbonate (1.36 g, 9.84 mmol), 1-o-tolyl-piperizine 1c (1.29 g, 7.35 mmol) were stirred at 25° C. for 16 h. LCMS indicated the formation of regio-isomers. Filtered and the solid was washed with methanol (100 mL). This was this was taken to preparative HPLC and the products were separated. The desired product 3b was confirmed by NMR analysis and taken to next step.

LCMS (ESI) 360 (M+H);

$^1$H NMR (400 MHz, DICHLOROMETHANE-$d_2$) δ ppm 2.30 (s, 3H) 2.97-3.06 (m, 3H) 3.25-3.34 (m, 4H) 3.40 (br s, 2H) 6.82 (d, J=13.13 Hz, 1H) 6.93-7.09 (m, 2H) 7.12-7.24 (m, 2H) 8.47 (d, J=7.81 Hz, 1H).

Step 2: 2-Fluoro-5-nitro-4-(4-o-tolyl-piperazin-1-yl)-benzoic acid 3b (65.0 mg, 0.18 mmol) was taken in DMF (2.0 mL) and HATU (137.5 mg, 0.36 mmol) was added to this and stirred for 3 min. N,N-diisopropylethylamine (0.90 mmol, 0.117 g) was added to this and the mixture was stirred again for 3 min. 1-(3-Amino-propyl)-pyrrolidin-2-one 1e (38.5 mg, 0.27 mmol) was added and the reaction mixture was stirred at room temperature for 16 h. A saturated solution of lithium chloride was added and the product was extracted with dichloromethane. Organic layer was washed with brine and dried over anhydrous sodium sulfate and concentrated to give the crude product 3c which was purified on preparative HPLC using water/methanol as eluent.

Step 3: To a solution of degassed ethanol (5.0 mL) and Pd/C (5 wt %) (48.4 mg, 0.023 mmol) was added 2-fluoro-5-nitro-N-[3-(2-oxo-pyrrolidin-1-yl)-propyl]-4-(4-o-tolyl-piperazin-1-yl)-benzamide 3c (55.0 mg, 0.114 mmol) in ethanol (1.0 mL). The solution stirred under hydrogen (1 atm) for 4 h then concentrated to give crude product 3d.

Step 4: To a solution of 2-cyclopropyl-oxazole-4-carboxylic acid 1h (22.8 mg, 0.149 mmol) in DMF (5.0 mL) HATU (75.4 mg, 0.198 mmol) was added and stirred for 3 min. N,N-diisopropylethylamine (0.086 mL, 0.496 mmol) was added to this followed by 5-amino-2-fluoro-N-[3-(2-oxo-pyrrolidin-1-yl)-propyl]-4-(4-o-tolyl-piperazin-1-yl)-benzamide 3d (45.0 mg, 0.099 mmol) in DMF (2.0 mL) and the reaction was stirred at room temperature for 16 h. Saturated solution of lithium chloride was added to this and the contents were extracted with ethyl acetate dried on anhydrous sodium sulfate, concentrated and the crude 3e was dissolved in methanol and purified on preparative HPLC using water/methanol as eluent.

LCMS (ESI) 589 (M+H);

$^1$H NMR (400 MHz, METHANOL-$d_4$) δ ppm 1.04-1.18 (m, 4H) 1.65-1.87 (m, 2H) 1.85-1.92 (m, 1H) 1.99-2.18 (m, 3H) 2.33 (s, 5H) 3.07-3.20 (m, 8H) 3.32-3.41 (m, 4H) 3.44-3.54 (m, 2H) 6.91-7.02 (m, 1H) 7.10-7.20 (m, 5H) 8.23-8.34 (m, 1H) 8.67-8.78 (m, 1H).

EXAMPLE 4

Synthetic route towards 2-cyclopropyl-oxazole-4-carboxylic acid [5-[3-(2-oxo-pyrrolidin-1-yl)-propyl-carbamoyl]-2-(4-o-tolyl-piperazin-1-yl)-3-trifluoromethyl-phenyl]-amide 4e

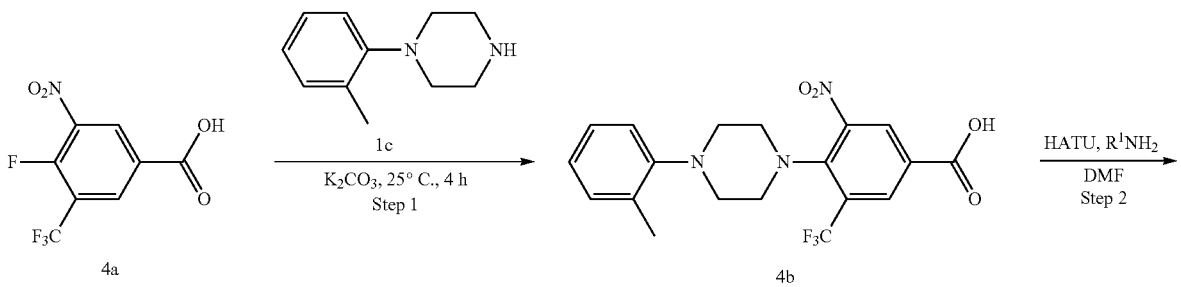

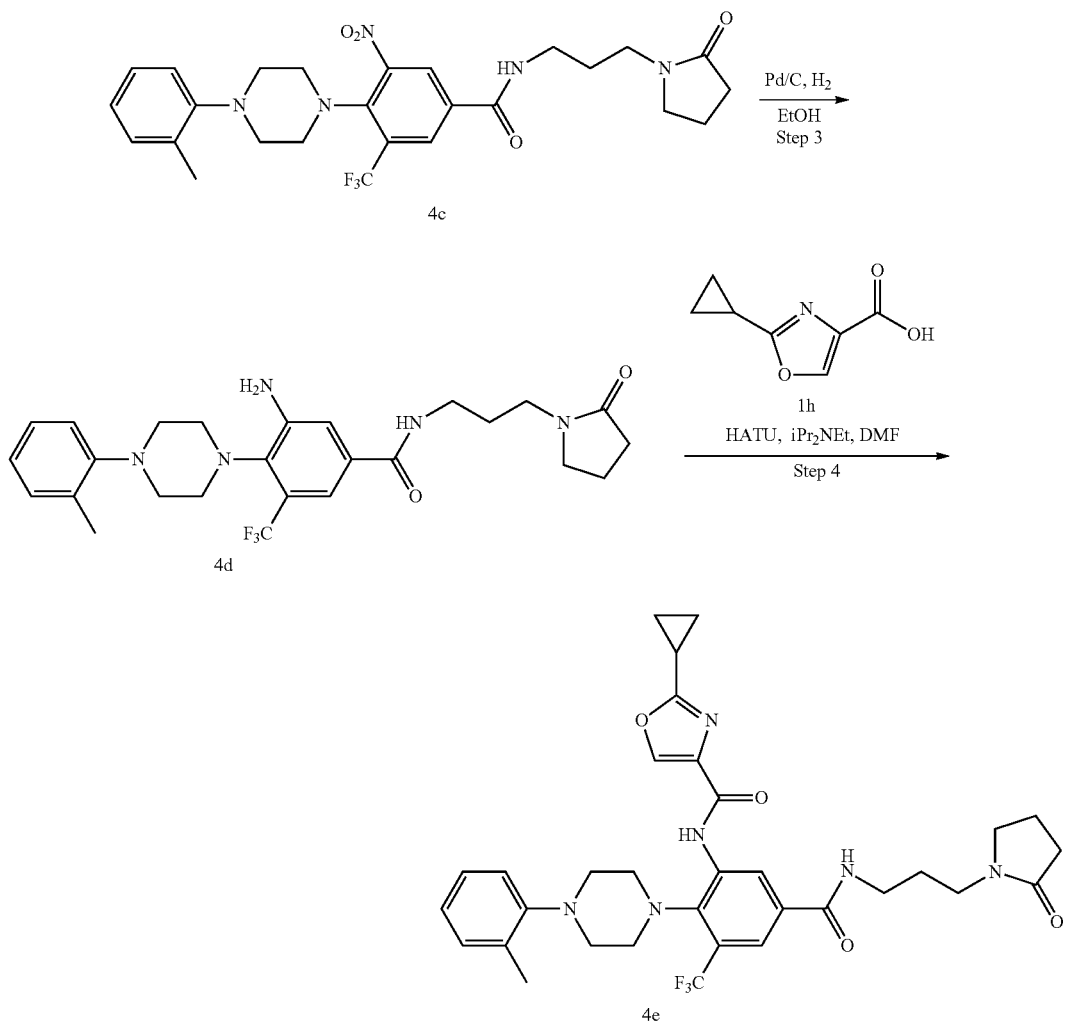

Step 1: To a solution of 4-fluoro-3-nitro-5-trifluoromethyl-benzoic acid 4a (1.0 g, 3.95 mmol) in DMF (20.0 mL) was added slowly 1-o-tolyl-piperazine 1c (835.6 mg, 4.74 mmol) followed by potassium carbonate (1.1 g, 7.90 mmol) and the reaction was stirred for 16 h. 20.0 mL of a saturated lithium chloride solution was added to this and extracted with ethyl acetate and concentrated to provide crude 4b.

Step 2: To a solution of 3-nitro-4-(4-o-tolyl-piperazin-1-yl)-5-trifluoromethyl-benzoic acid 4b (500 mg, 1.2 mmol) in DMF (5.0 mL) was added HATU (928.8 mg, 2.44 mmol) and stirred for 4 min. N, N-diisopropylethylamine (1.1 mL, 6.10 mmol) was added to this and stirred for another 4 min. 1-(3-Amino-propyl)-pyrrolidin-2-one 1e (260.5 mg, 1.83 mmol) was added to this and the reaction was stirred at room temperature for 16 h. A saturated solution of lithium chloride was added and extracted with ethyl acetate. Organic layer was washed with brine and dried on anhydrous sodium sulfate, concentrated and the crude 4c was taken to next step.

Step 3: 3-Nitro-N-[3-(2-oxo-pyrrolidin-1-yl)-propyl]-4-(4-o-tolyl-piperazin-1-yl)-5-trifluoromethyl-benzamide 4c (600.0 mg, 1.125 mmol) was taken in ethanol and evacuated and nitrogen purged. This was added to a flask containing Pd/C (5 wt %) (23.9 mg, 0.23 mmol) under nitrogen. The solution was evacuated again and the solution was stirred under hydrogen for 4 h. Hydrogen was removed, the reaction was evacuated and nitrogen purged. The content was filtered over Celite and concentrated to give crude 4d product which was taken to next step.

Step 4: To a solution of 3-amino-N-[3-(2-oxo-pyrrolidin-1-yl)-propyl]-4-(4-o-tolyl-piperazin-1-yl)-5-trifluoromethyl-benzamide 4d (87.0 mg, 0.173 mmol) in DMF (3.0 mL) was added HATU (131.4 mg, 0.346 mmol) and stirred for 4 min. N,N-diisopropylethylamine (0.11 g, 0.86 mmol) was added to this and the solution was stirred for another 4 min. 2-Cyclopropyl-oxazole-4-carboxylic acid 1h (39.6 mg, 0.26 mmol) was added to this and the reaction was stirred at 25° C. for 16 h. A saturated solution of lithium chloride was added and extracted with ethyl acetate. Organic layer was washed with brine and dried on anhydrous sodium sulfate, concentrated and the crude 4e was dissolved in methanol and purified on preparative HPLC using water/methanol as eluent.

LCMS (ESI) 639 (M+H);
$^1$H NMR (400 MHz, DICHLOROMETHANE-$d_2$) δ ppm 1.00-1.14 (m, 4H) 1.76 (t, J=6.03 Hz, 2H) 1.98-2.13 (m, 3H) 2.35-2.45 (m, 5H) 2.99-3.17 (m, 4H) 3.27-3.43 (m, 9H) 3.45-3.54 (m, 2H) 6.94-7.04 (m, 1H) 7.12-7.23 (m, 3H) 7.82 (s, 1H) 7.95 (d, J=2.15 Hz, 1H) 8.16 (s, 1H) 9.22 (d, J=2.05 Hz, 1H) 10.26 (br. s, 1H).

EXAMPLE 5

Synthetic route towards 2-cyclopropyl-oxazole-4-carboxylic acid [4-cyclopropyl-5-[3-(2-oxo-pyrrolidin-1-yl)-propylcarbamoyl]-2-(4-o-tolyl-piperazin-1-yl)-phenyl]-amide 5c and furan-2-carboxylic acid [4-cyclopropyl-5-[3-(2-oxo-pyrrolidin-1-yl)-propylcarbamoyl]-2-(4-o-tolyl-piperazin-1-yl)-phenyl]-amide 5d

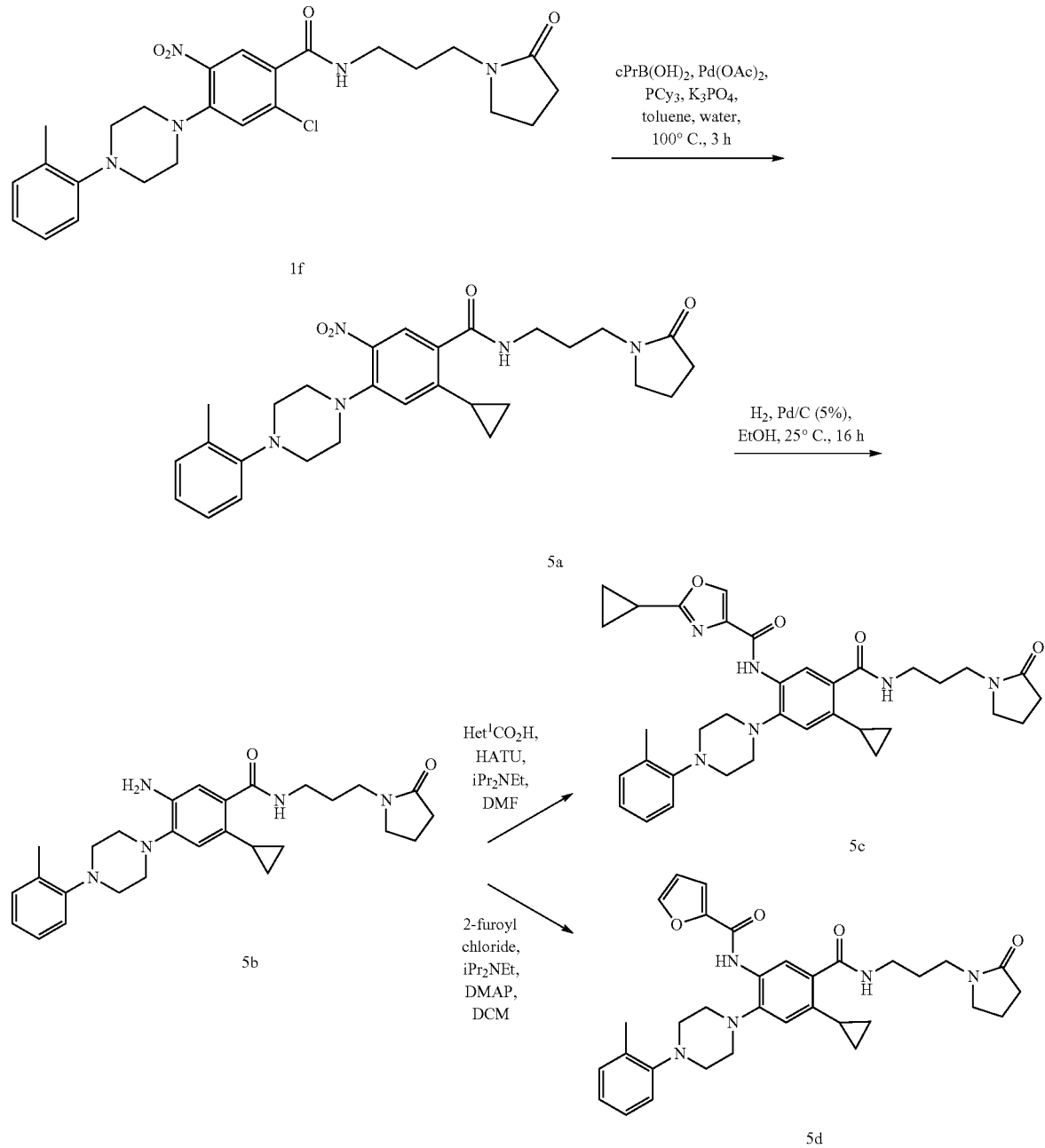

Step 1: 2-Chloro-5-nitro-N-[3-(2-oxo-pyrrolidin-1-yl)-propyl]-4-(4-o-tolyl-piperazin-1-yl)-benzamide 1f (200.0 mg, 0.40 mmol, 100 mol %), potassium phosphate tribasic (169.8 mg, 0.80 mmol, 200 mol %), cyclopropylboronic acid (41.2 mg, 0.48 mmol, 120 mol %), tricyclohexylphosphine (11.2 mg, 0.04 mmol, 10 mol %), and palladium(II) acetate (4.5 mg, 0.02 mmol, 5 mol %) were combined in de-gassed toluene (4.0 ml) and 200 mL of water was added. The vessel was sealed and heated to 100° C. for 3 h and then the reaction was cooled and diluted with water and ethyl acetate. The suspension was filtered through a pad of Celite and the mixture was extracted twice with ethyl acetate and the combined organic extracts were dried over sodium sulfate and concentrated. Column chromatography (dichloromethane to 10% methanol in dichloromethane) afforded 2-cyclopropyl-5-nitro-N-[3-(2-oxo-pyrrolidin-1-yl)-propyl]-4-(4-o-tolyl-piperazin-1-yl)-benzamide 5a (161.0 mg; 0.32 mmol; 79.6%) as an amorphous yellow solid. LCMS (ESI) 506 (M+H).

Step 2: 2-Cyclopropyl-5-nitro-N-[3-(2-oxo-pyrrolidin-1-yl)-propyl]-4-(4-o-tolyl-piperazin-1-yl)-benzamide 5a (161.0 mg, 0.32 mmol, 100 mol %) was dissolved in ethanol (8.0 ml) and palladium on carbon (5 wt %) (67.8 mg, 0.03 mmol, 10 mol %) was added. The reaction was placed under an atmosphere of hydrogen and stirred for 16 h at room temperature. The reaction was then filtered through a pad of Celite and the filtrate was concentrated to an off-white solid, 5-amino-2-cyclopropyl-N-[3-(2-oxo-pyrrolidin-1-yl)-propyl]-4-(4-o-tolyl-piperazin-1-yl)-benzamide 5b (155.0 mg, 0.33 mmol), that was used without additional purification. LCMS (ESI) 476 (M+H).

Step 3-5c: 5-Amino-2-cyclopropyl-N-[3-(2-oxo-pyrrolidin-1-yl)-propyl]-4-(4-o-tolyl-piperazin-1-yl)-benzamide 5b (89.0 mg, 0.19 mmol, 100 mol %), 2-cyclopropyl-oxazole-4-carboxylic acid 1h (43.0 mg, 0.28 mmol, 150 mol %) and N,N-diisopropylethylamine (0.10 ml, 0.56 mmol, 300 mol %) were combined in N,N-dimethylformamide (3.0 ml) and HATU (106.7 mg, 0.28 mmol, mol %) was added and the reaction was stirred at room temperature for 16 h. The reaction was then diluted with water and extracted three times with ethyl acetate. The combined organics were dried over sodium sulfate and then concentrated to a residue that was purified by column chromatography (dichloromethane to 10% methanol/dichloromethane) to afford 2-cyclopropyl-oxazole-4-carboxylic acid [4-cyclopropyl-5-[3-(2-oxo-pyrrolidin-1-yl)-propylcarbamoyl]-2-(4-o-tolyl-piperazin-1-yl)-phenyl]-amide 5c (34.0 mg; 0.06 mmol, 29.8%) as a white solid.

LCMS (ESI) 611 (M+H);
$^1$H NMR (400 MHz, METHANOL-d4) δ ppm 0.63-0.79 (m, 2H) 0.88-1.04 (m, 2H) 1.09-1.19 (m, 4H) 2.04-2.13 (m, 2H) 2.36 (s, 5H) 2.99-3.11 (m, 4H) 3.17 (d, J=4.98 Hz, 4H) 3.40 (d, J=6.98 Hz, 4H) 3.48-3.64 (m, 2H) 6.96 (s, 2H) 7.12-7.27 (m, 3H) 8.31 (s, 1H) 8.40 (s, 1H).

Step 3-5d: To a solution of 5-amino-2-cyclopropyl-N-[3-(2-oxo-pyrrolidin-1-yl)-propyl]-4-(4-o-tolyl-piperazin-1-yl)-benzamide 5b (66.0 mg, 0.14 mmol, 100 mol %) and N,N-diisopropylethylamine (0.07 ml, 0.42 mmol, 300 mol %) in dichloromethane (4.0 ml) was added furan-2-carbonyl chloride (0.02 ml, 0.21 mmol, 150 mol %) and a catalytic amount of N,N-dimethylaminopyridine. The reaction was stirred for 16 h at room temperature and then diluted with water and extracted three times with dichloromethane. The combined organics were dried over sodium sulfate and concentrated to a residue that was purified by column chromatography (dichloromethane to 10% methanol/dichloromethane) to afford furan-2-carboxylic acid [4-cyclopropyl-5-[3-(2-oxo-pyrrolidin-1-yl)-propylcarbamoyl]-2-(4-o-tolyl-piperazin-1-yl)-phenyl]-amide 5d (39.3 mg; 0.07 mmol, 49.7%) as an off-white solid.

LCMS (ESI) 570 (M+H);
$^1$H NMR (400 MHz, METHANOL-d4) δ ppm 0.64-0.81 (m, 2H) 0.90-1.05 (m, 2H) 2.04-2.14 (m, 2H) 2.35 (s, 3H) 2.37-2.47 (m, 2H) 3.02-3.19 (m, 8H) 3.37-3.45 (m, 4H) 3.48-3.61 (m, 2H) 6.60-6.72 (m, 1H) 6.93-7.03 (m, 2H) 7.12-7.21 (m, 3H) 7.24-7.33 (m, 1H) 7.69-7.90 (m, 1H) 8.20-8.40 (m, 1H).

EXAMPLE 6

Synthetic route towards 2-cyclopropyl-oxazole-4-carboxylic acid [4-ethyl-5-[3-(2-oxo-pyrrolidin-1-yl)-propylcarbamoyl]-2-(4-o-tolyl-piperazin-1-yl)-phenyl]-amide 6c

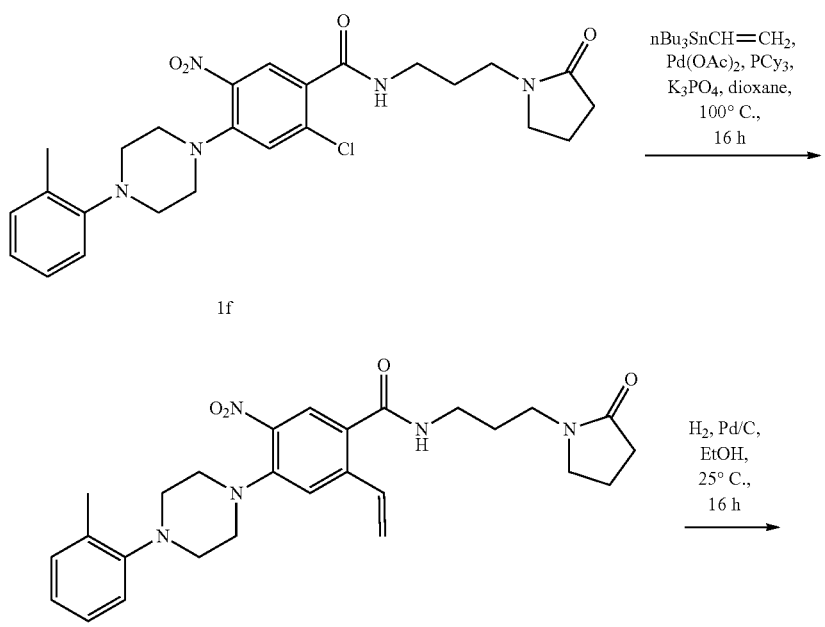

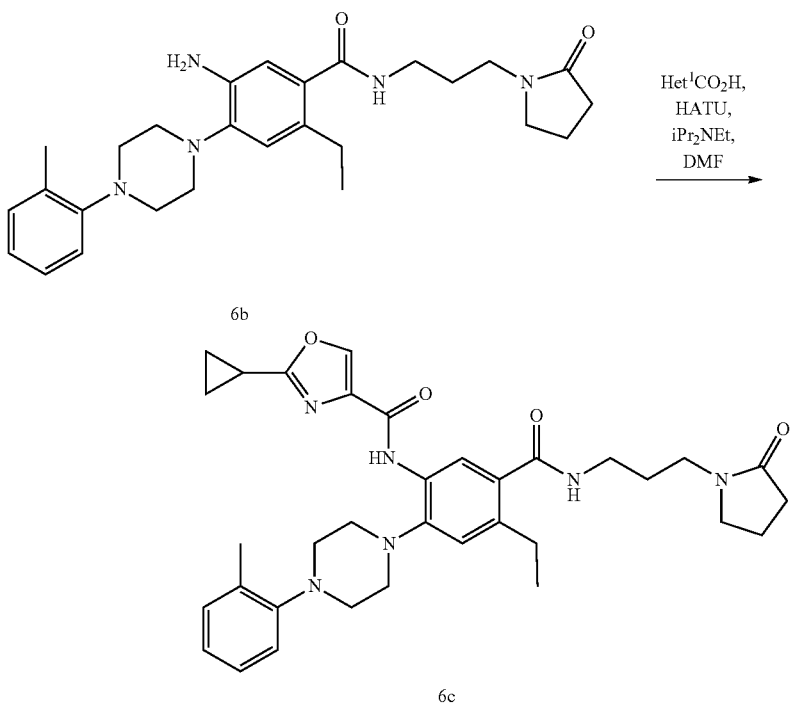

Step 1: 2-Chloro-5-nitro-N-[3-(2-oxo-pyrrolidin-1-yl)-propyl]-4-(4-o-tolyl-piperazin-1-yl)-benzamide 1f (400.0 mg, 0.80 mmol, 100 mol %), 1M aqueous potassium phosphate, tribasic (1.6 ml, 1.60 mmol, 200 mol %), tricyclohexylphosphine (22.4 mg, 0.08 mmol, 10 mol %), tributyl-vinyl-stannane (304.4 mg, 0.96 mmol, 120 mol %) and palladium (II) acetate (9.0 mg, 0.04 mmol, 5 mol %) were dissolved in 12.0 mL of dioxane in a 40 mL scintillation vial and the vessel was sealed and heated to 100° C. for 16 h. The reaction was then diluted with water and ethyl acetate and filtered through a pad of Celite. The filtrate was extracted twice with ethyl acetate and the combined organics were dried over sodium sulfate and concentrated. After two column chromatography runs, first with dichloromethane/methanol and then with ethyl acetate/methanol, 5-nitro-N-[3-(2-oxo-pyrrolidin-1-yl)-propyl]-4-(4-o-tolyl-piperazin-1-yl)-2-vinyl-benzamide 6a (41.0 mg, 0.08 mmol, 10.4%) was obtained in pure form. LCMS (ESI) 492 (M+H).

Step 2: 5-Nitro-N-[3-(2-oxo-pyrrolidin-1-yl)-propyl]-4-(4-o-tolyl-piperazin-1-yl)-2-vinyl-benzamide 6a (41.0 mg, 0.08 mmol, 100 mol %) was dissolved in ethanol (4.0 ml) and tetrahydrofuran (1.0 mL) and palladium on carbon (5 wt %) (17.8 mg, 0.01 mmol, 10 mol %) was added. The reaction was placed under an atmosphere of hydrogen and stirred for 16 h at room temperature. The reaction was then filtered through a pad of Celite and the filtrate was concentrated to an off-white solid, 5-amino-2-ethyl-N-[3-(2-oxo-pyrrolidin-1-yl)-propyl]-4-(4-o-tolyl-piperazin-1-yl)-benzamide 6b (36.0 mg; 0.08 mmol) that was used without additional purification. LCMS (ESI) 464 (M+H).

Step 3: 5-Amino-2-ethyl-N-[3-(2-oxo-pyrrolidin-1-yl)-propyl]-4-(4-o-tolyl-piperazin-1-yl)-benzamide 6b (36.0 mg, 0.08 mmol, 100 mol %), 2-cyclopropyl-oxazole-4-carboxylic acid 1h (17.8 mg, 0.12 mmol, 150 mol %) and N,N-diisopropylethylamine (0.04 ml, 0.23 mmol, 300 mol %) were combined in N,N-dimethylformamide (2.0 ml) and HATU (44.3 mg, 0.12 mmol, mol %) was added and the reaction was stirred at room temperature for 16 h. The reaction was then diluted with water and extracted three times with ethyl acetate. The combined organics were dried over sodium sulfate and then concentrated to a residue that was purified by column chromatography (dichloromethane to 10% methanol/dichloromethane) to afford 2-cyclopropyl-oxazole-4-carboxylic acid [4-ethyl-5-[3-(2-oxo-pyrrolidin-1-yl)-propyl-carbamoyl]-2-(4-o-tolyl-piperazin-1-yl)-phenyl]-amide 6c (23.4 mg; 0.04 mmol, 50.3%) as a white solid.

LCMS (ESI) 599 (M+H);

$^1$H NMR (400 MHz, METHANOL-d4) δ ppm 1.12 (d, J=6.64 Hz, 4H) 1.21 (s, 3H) 1.75-1.88 (m, 2H) 2.01-2.10 (m, 2H) 2.34 (s, 5H) 2.68-2.83 (m, 2H) 3.03-3.11 (m, 4H) 3.14-3.19 (m, 4H) 3.32-3.42 (m, 4H) 3.46-3.56 (m, 2H) 6.92-7.02 (m, 1H) 7.11-7.19 (m, 3H) 7.20-7.25 (m, 1H) 8.28 (s, 1H) 8.37 (s, 1H).

EXAMPLE 7

Synthetic route towards furan-2-carboxylic acid [4-dimethylamino-5-[3-(2-oxo-pyrrolidin-1-yl)-propylcarbamoyl]-2-(4-o-tolyl-piperazin-1-yl)-phenyl]-amide 7d and 2-cyclopropyl-oxazole-4-carboxylic acid [4-dimethylamino-5-[3-(2-oxo-pyrrolidin-1-yl)-propylcarbamoyl]-2-(4-o-tolyl-piperazin-1-yl)-phenyl]-amide 7e concentrated to dryness and purified by column chromatography (heptane/ethyl acetate gradient) to afford the anilino-acid intermediate 7a (120 mg) as a pale yellow solid. LCMS (ESI) 383 (M−H).

Step 2: 7a was then dissolved in N,N-dimethylformamide (4.0 ml) and N,N-diisopropylethylamine (0.17 ml, 0.98

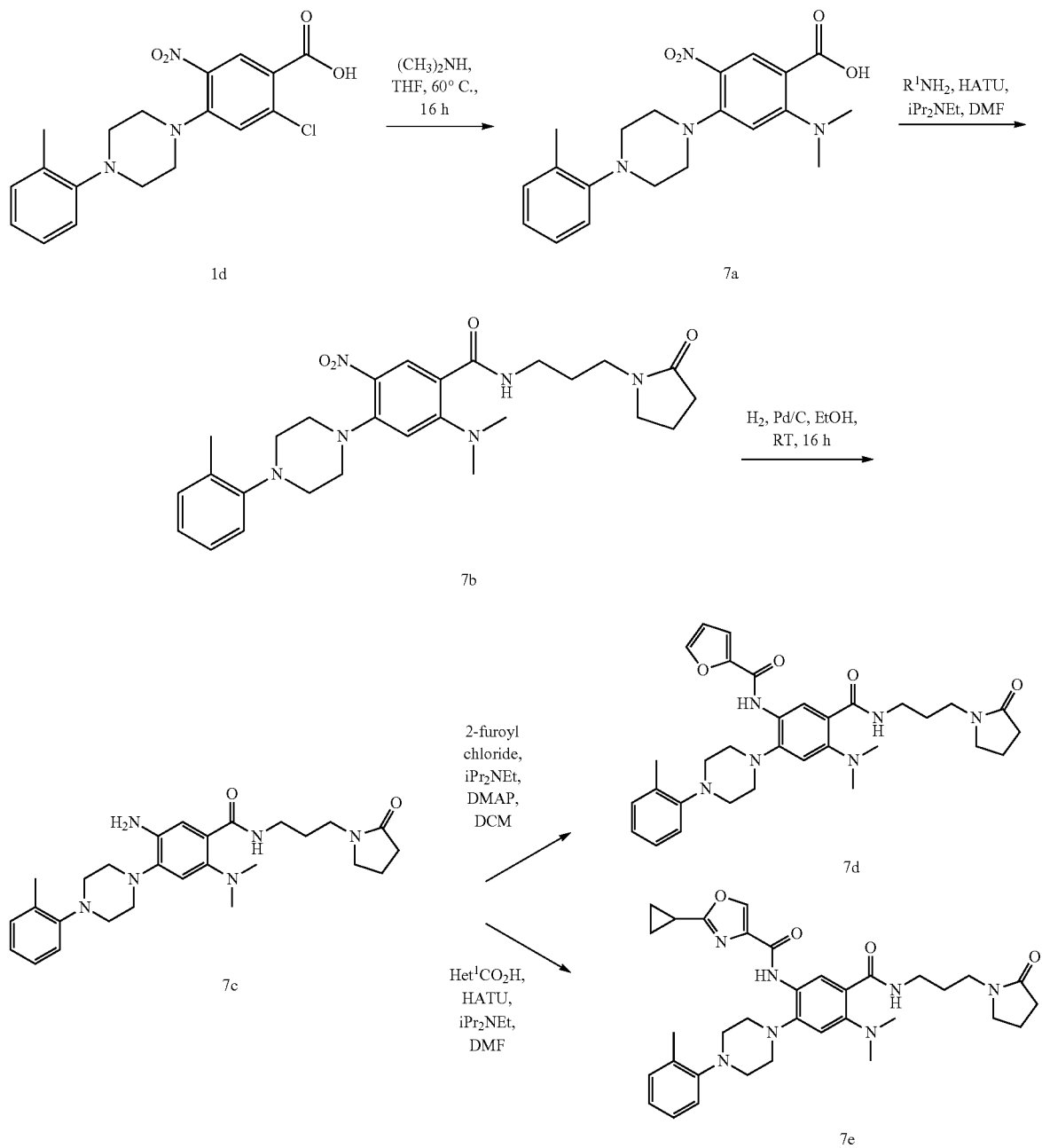

Step 1: 2-Chloro-5-nitro-4-(4-o-tolyl-piperazin-1-yl)-benzoic acid 1d (250.0 mg, 0.66 mmol, 100 mol %) was dissolved in 2M dimethyl-amine (8.0 ml; 16.00 mmol) in THF and the reaction was heated to 60° C. for 16 h. The reaction was then mmol, 146.71 mol %) and 1-(3-amino-propyl)-pyrrolidin-2-one 1e (0.09 ml, 0.63 mmol, 94.08 mol %) were added followed by HATU (143.0 mg, 0.38 mmol, 56.53 mol %). The reaction was run at room temperature for 16 h and then diluted with water and ethyl acetate. The mixture was extracted two times with ethyl acetate and the combined organic extracts were dried over sodium sulfate and concentrated. The residue was purified by column chromatography (dichloromethane to 10% methanol/dichloromethane) to afford 2-dimethylamino-5-nitro-N-[3-(2-oxo-pyrrolidin-1-yl)-propyl]-4-(4-o-tolyl-piperazin-1-yl)-benzamide 7b (161.0 mg; 0.32 mmol, 47.6%, 2 steps) as a yellow solid. LCMS (ESI) 509 (M+H).

Step 3: 2-Dimethylamino-5-nitro-N-[3-(2-oxo-pyrrolidin-1-yl)-propyl]-4-(4-o-tolyl-piperazin-1-yl)-benzamide 7b (161.0 mg, 0.32 mmol, 100 mol %) was dissolved in ethanol (10.0 ml) and tetrahydrofuran (2.0 mL) and palladium on carbon (5 wt %) (10.0 mol %) was added. The reaction was placed under an atmosphere of hydrogen and stirred for 16 h at room temperature. The reaction was then filtered through a pad of Celite and the filtrate was concentrated to an off-white solid, 5-amino-2-dimethylamino-N-[3-(2-oxo-pyrrolidin-1-yl)-propyl]-4-(4-o-tolyl-piperazin-1-yl)-benzamide 7c (150.0 mg; 0.31 mmol) that was used without additional purification. LCMS (ESI) 479 (M+H).

Step 4-7d: To a solution of 5-amino-2-dimethylamino-N-[3-(2-oxo-pyrrolidin-1-yl)-propyl]-4-(4-o-tolyl-piperazin-1-yl)-benzamide 7c (91.7 mg, 0.19 mmol, 100 mol %) and N,N-diisopropylethylamine (0.10 ml, 0.58 mmol, 300 mol %) in dichloromethane (4.0 ml) was added furan-2-carbonyl chloride (0.02 ml, 0.23 mmol, 120 mol %) and a catalytic amount of N,N-dimethylaminopyridine. The reaction was stirred for 16 h at room temperature and then diluted with water and extracted three times with dichloromethane. The combined organics were dried over sodium sulfate and concentrated to a residue that was purified by column chromatography (dichloromethane to 10% methanol/dichloromethane) to afford furan-2-carboxylic acid [4-dimethylamino-5-[3-(2-oxo-pyrrolidin-1-yl)-propylcarbamoyl]-2-(4-o-tolyl-piperazin-1-yl)-phenyl]-amide 7d (50.0 mg; 0.09 mmol, 45.6%) as an off-white solid.

LCMS (ESI) 573 (M+H);
$^1$H NMR (400 MHz, METHANOL-d4) δ ppm 1.86 (s, 2H) 1.99-2.15 (m, 2H) 2.35 (s, 3H) 2.38 (d, J=8.15 Hz, 2H) 2.80 (s, 6H) 3.10-3.21 (m, 8H) 3.37-3.46 (m, 4H) 3.51 (t, J=7.13 Hz, 2H) 6.62-6.74 (m, 1H) 6.91-7.05 (m, 1H) 7.11-7.22 (m, 4H) 7.24-7.31 (m, 1H) 7.73-7.86 (m, 1H) 8.70 (s, 1H).

Step 4-7e: 5-Amino-2-dimethylamino-N-[3-(2-oxo-pyrrolidin-1-yl)-propyl]-4-(4-o-tolyl-piperazin-1-yl)-benzamide 7c (111.4 mg, 0.23 mmol, 100 mol %), 2-cyclopropyl-oxazole-4-carboxylic acid 1h (53.5 mg, 0.35 mmol, 150 mol %) and N,N-diisopropylethylamine (0.12 ml, 0.70 mmol, 300 mol %) were combined in N,N-dimethylformamide (2.0 ml) and HATU (132.7 mg, 0.35 mmol, mol %) was added and the reaction was stirred at room temperature for 16 h. The reaction was then diluted with water and extracted three times with ethyl acetate. The combined organics were dried over sodium sulfate and then concentrated to a residue that was purified by column chromatography (dichloromethane to 10% methanol/dichloromethane) to afford 2-cyclopropyl-oxazole-4-carboxylic acid [4-dimethylamino-5-[3-(2-oxo-pyrrolidin-1-yl)-propylcarbamoyl]-2-(4-o-tolyl-piperazin-1-yl)-phenyl]-amide 7e (100.0 mg; 0.16 mmol, 70.0%) as a white solid.

LCMS (ESI) 614 (M+H);
$^1$H NMR (400 MHz, METHANOL-d4) δ ppm 1.07-1.20 (m, 4H) 1.86 (s, 2H) 2.02-2.13 (m, 2H) 2.33-2.48 (m, 5H) 2.75-2.84 (m, 6H) 3.16 (dd, J=16.62, 5.59 Hz, 8H) 3.41 (d, J=2.34 Hz, 4H) 3.46-3.59 (m, 2H) 6.94-7.07 (m, 1H) 7.14-7.29 (m, 4H) 8.30 (s, 1H) 8.87 (s, 1H).

EXAMPLE 8

Synthetic route towards 2-cyclopropyl-oxazole-4-carboxylic acid [4-ethoxy-5-[3-(2-oxo-pyrrolidin-1-yl)-propylcarbamoyl]-2-(4-o-tolyl-piperazin-1-yl)-phenyl]-amide 8e, 2-cyclopropyl-oxazole-4-carboxylic acid [4-(2-methoxy-ethoxy)-5-[3-(2-oxo-pyrrolidin-1-yl)-propylcarbamoyl]-2-(4-o-tolyl-piperazin-1-yl)-phenyl]-amide 8f and furan-2-carboxylic acid [4-ethoxy-5-[3-(2-oxo-pyrrolidin-1-yl)-propylcarbamoyl]-2-(4-o-tolyl-piperazin-1-yl)-phenyl]-amide 8g

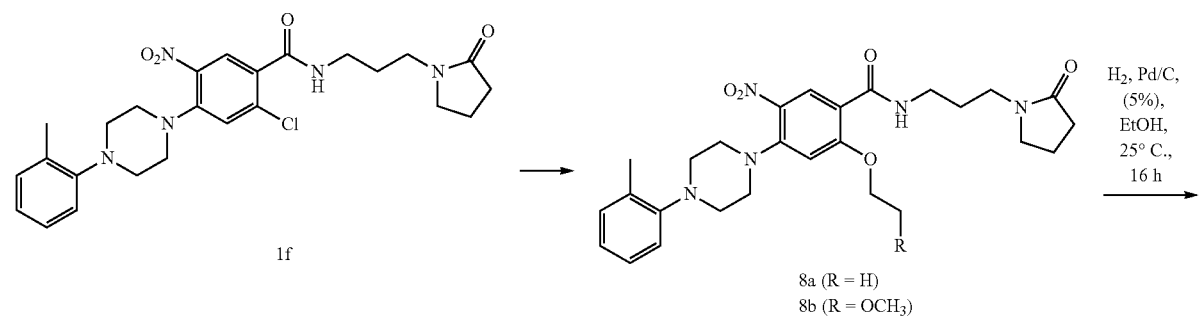

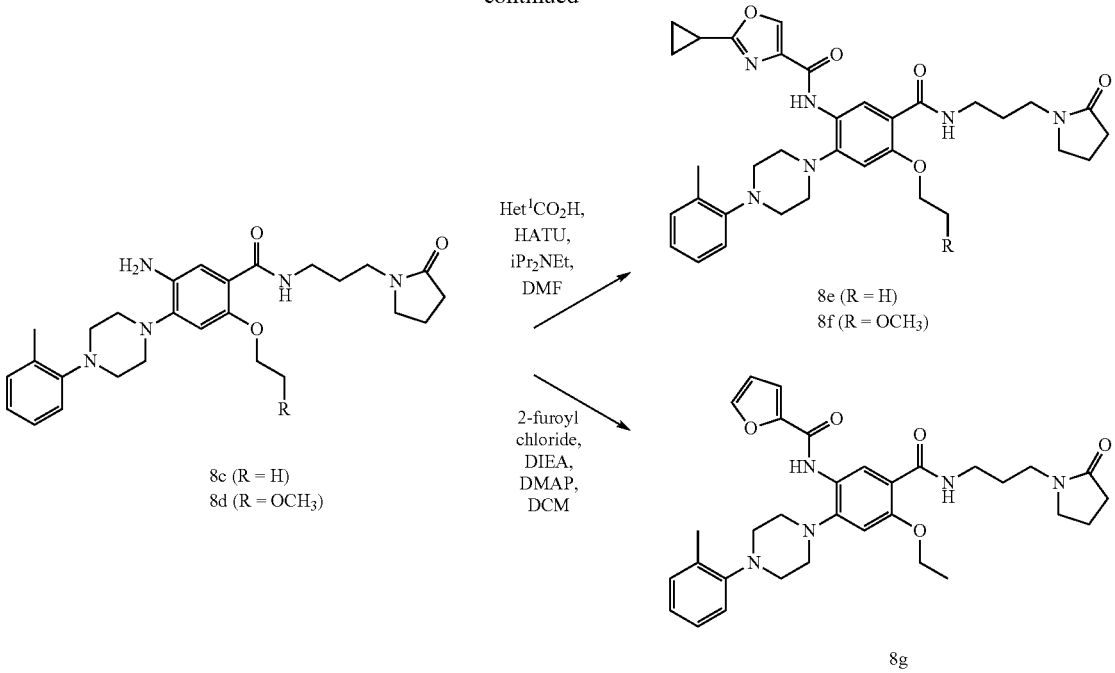

Step 1-8e: 2-Chloro-5-nitro-N-[3-(2-oxo-pyrrolidin-1-yl)-propyl]-4-(4-o-tolyl-piperazin-1-yl)-benzamide 1f (265.0 mg, 0.53 mmol, 100 mol %) was dissolved in ethanol (4.0 ml) and tetrahydrofuran (4.0 ml) and sodium hydride (60%, 106.0 mg, 2.65 mmol, 500 mol %) was added carefully in small portions. The reaction was stirred at room temperature for 16 h and then diluted with saturated aqueous ammonium chloride and ethyl acetate. The mixture was extracted with ethyl acetate two times and the combined organics were dried over sodium sulfate and concentrated.

Step 2-8e: The resulting residue 8a was dissolved in 12.0 ml of ethanol and a catalytic amount (10 mol %) of 5% palladium on carbon was added. The vessel was charged with a hydrogen atmosphere and the reaction was stirred for 16 h. The suspension was then filtered through a pad of Celite and the filtrate was concentrated to a light brown foam 5-amino-2-ethoxy-N-[3-(2-oxo-pyrrolidin-1-yl)-propyl]-4-(4-o-tolyl-piperazin-1-yl)-benzamide 8c (103.1 mg, 0.22 mmol, 40.6%, 2 steps) that was used without additional purification. LCMS (ESI) 480 (M+H).

Step 3-8e: 5-Amino-2-ethoxy-N-[3-(2-oxo-pyrrolidin-1-yl)-propyl]-4-(4-o-tolyl-piperazin-1-yl)-benzamide 8c (58.3 mg, 0.12 mmol, 100 mol %), 2-cyclopropyl-oxazole-4-carboxylic acid 1 h (27.9 mg, 0.18 mmol, 150 mol %) and N,N-diisopropylethylamine (0.06 ml, 0.36 mmol, 300 mol %) were combined in N,N-dimethylformamide (3.0 ml) and HATU (69.3 mg, 0.18 mmol, mol %) was added and the reaction was stirred at room temperature for 16 h. The reaction was then diluted with water and extracted three times with ethyl acetate. The combined organics were dried over sodium sulfate and then concentrated to a residue that was purified by reverse phase HPLC (methanol+0.1% formic acid/water) to afford 2-cyclopropyl-oxazole-4-carboxylic acid [4-ethoxy-5-[3-(2-oxo-pyrrolidin-1-yl)-propylcarbamoyl]-2-(4-o-tolyl-piperazin-1-yl)-phenyl]-amide 8e (54.8 mg, 0.09 mmol, 73.3%) as a white solid.

LCMS (ESI) 615 (M+H);
$^1$H NMR (400 MHz, METHANOL-d4) δ ppm 1.08-1.16 (m, 4H) 1.51 (t, J=7.03 Hz, 3H) 1.84 (t, J=6.64 Hz, 2H) 2.06 (d, J=7.61 Hz, 3H) 2.34 (s, 3H) 2.36-2.44 (m, 2H) 3.06-3.21 (m, 8H) 3.36-3.44 (m, 4H) 3.49 (t, J=7.03 Hz, 2H) 4.27 (d, J=7.03 Hz, 2H) 6.97 (s, 2H) 7.12-7.24 (m, 3H) 8.28 (s, 1H) 8.41-8.52 (m, 1H) 8.89 (s, 1H).

Step 3-8g: To a solution of 5-amino-2-ethoxy-N-[3-(2-oxo-pyrrolidin-1-yl)-propyl]-4-(4-o-tolyl-piperazin-1-yl)-benzamide 8c (44.8 mg, 0.09 mmol, 100 mol %) and N,N-diisopropylethylamine (0.05 ml, 0.28 mmol, 300 mol %) in dichloromethane (2.0 ml) was added furan-2-carbonyl chloride (0.01 ml, 0.11 mmol, 120 mol %) and a catalytic amount of N,N-dimethylaminopyridine. The reaction was stirred for 16 h at room temperature and then diluted with water and extracted three times with dichloromethane. The combined organics were dried over sodium sulfate and concentrated and the residue was purified by column chromatography (dichloromethane to 10% methanol/dichloromethane) to afford furan-2-carboxylic acid [4-ethoxy-5-[3-(2-oxo-pyrrolidin-1-yl)-propylcarbamoyl]-2-(4-o-tolyl-piperazin-1-yl)-phenyl]-amide 8g (30.7 mg, 0.05 mmol, 53.6%) as an off-white solid.

LCMS (ESI) 574 (M+H);
$^1$H NMR (400 MHz, DICHLOROMETHANE-d2) δ ppm 1.42-1.55 (m, 2H) 1.81 (t, J=6.74 Hz, 2H) 1.93-2.11 (m, 2H) 2.30 (d, J=8.40 Hz, 2H) 2.35 (s, 3H) 3.05-3.26 (m, 8H) 3.30-3.49 (m, 6H) 4.25 (q, J=6.96 Hz, 2H) 6.59 (dd, J=3.51, 1.76 Hz, 1H) 6.86 (s, 1H) 7.01 (s, 1H) 7.14 (s, 1H) 7.17-7.27 (m, 3H) 7.59 (d, J=0.98 Hz, 1H) 8.05-8.20 (m, 1H) 8.94 (s, 1H) 8.99 (s, 1H).

Step 1-8f: 2-Chloro-5-nitro-N-[3-(2-oxo-pyrrolidin-1-yl)-propyl]-4-(4-o-tolyl-piperazin-1-yl)-benzamide 1f (265.0 mg, 0.53 mmol, 100 mol %) was dissolved in 2-methoxyethanol (4.0 ml) and tetrahydrofuran (4.0 ml) and sodium hydride (60%, 106.0 mg, 2.65 mmol, 500 mol %) was added carefully in small portions. The reaction was stirred at room temperature for 16 h and then diluted with saturated aqueous ammonium chloride and ethyl acetate. The mixture was extracted with ethyl acetate two times and the combined organics were dried over sodium sulfate and concentrated.

Step 2-8f: The resulting residue 8b was dissolved in 12 ml of ethanol and a catalytic amount (10 mol %) of 5% palladium on carbon was added. The vessel was charged with a hydrogen atmosphere and the reaction was stirred for 16 h. The suspension was then filtered through a pad of Celite and the filtrate was concentrated to a light brown foam 5-amino-2-(2-methoxy-ethoxy)-N-[3-(2-oxo-pyrrolidin-1-yl)-propyl]-4-(4-o-tolyl-piperazin-1-yl)-benzamide 8d (91.7 mg, 0.18 mmol, 33.9%, 2 steps) that was used without additional purification. LCMS (ESI) 510 (M+H).

Step 3-8f: 5-Amino-2-(2-methoxy-ethoxy)-N-[3-(2-oxo-pyrrolidin-1-yl)-propyl]-4-(4-o-tolyl-piperazin-1-yl)-benzamide 8d (91.7 mg, 0.18 mmol, 100 mol %), 2-cyclopropyl-oxazole-4-carboxylic acid 1h (41.3 mg, 0.27 mmol, 150 mol %) and N,N-diisopropylethylamine (0.09 ml; 0.54 mmol; 300 mol %) were combined in N,N-dimethylformamide (4.0 ml) and HATU (102.6 mg, 0.27 mmol, 150 mol %) was added and the reaction was stirred at room temperature for 16 h. The reaction was then diluted with water and extracted three times with ethyl acetate. The combined organics were dried over sodium sulfate and then concentrated to a residue that was purified by reverse phase HPLC (methanol+0.1% formic acid/water) to afford 2-cyclopropyl-oxazole-4-carboxylic acid [4-(2-methoxy-ethoxy)-5-[3-(2-oxo-pyrrolidin-1-yl)-propylcarbamoyl]-2-(4-o-tolyl-piperazin-1-yl)-phenyl]-amide 8f (89.3 mg; 0.14 mmol, 77%) as a white solid.

LCMS (ESI) 645 (M+H);

$^1$H NMR (400 MHz, METHANOL-d4) δ ppm 1.06-1.16 (m, 4H) 1.85 (t, J=6.96 Hz, 2H) 1.99-2.18 (m, 3H) 2.33 (s, 3H) 2.34-2.41 (m, 2H) 3.03-3.17 (m, 8H) 3.35-3.43 (m, 4H) 3.44 (s, 3H) 3.48 (t, J=7.05 Hz, 2H) 3.74-3.89 (m, 2H) 4.25-4.40 (m, 2H) 6.90-7.05 (m, 2H) 7.11-7.25 (m, 3H) 8.27 (s, 1H) 8.53-8.68 (m, 1H) 8.94 (s, 1H).

EXAMPLE 9

Synthetic route towards 2-cyclopropyl-oxazole-4-carboxylic acid [5-[3-(2-oxo-pyrrolidin-1-yl)-propylcarbamoyl]-2-(4-o-tolyl-piperazin-1-yl)-4-trifluoromethyl-phenyl]-amide 9e

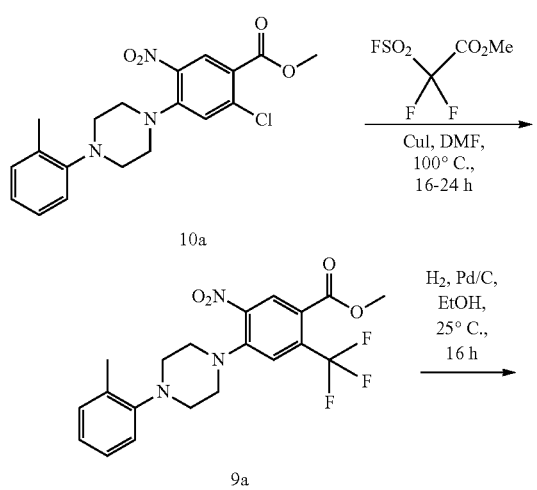

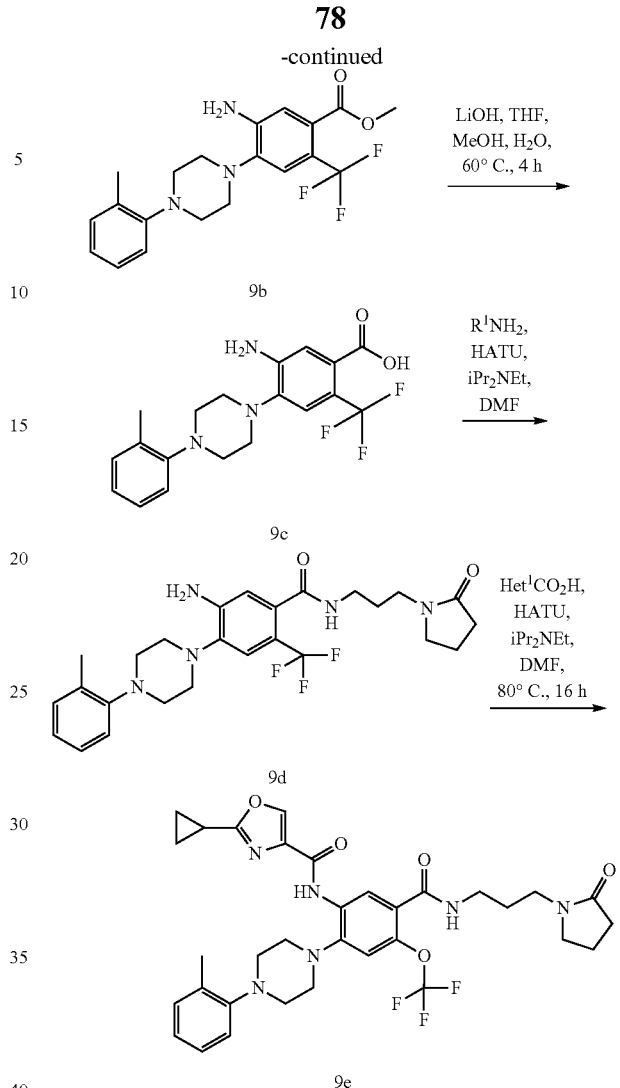

Step 1: 2-Chloro-5-nitro-4-(4-o-tolyl-piperazin-1-yl)-benzoic acid methyl ester 10a (329.0 mg, 0.84 mmol, 100 mol %) and copper iodide (160.7 mg, 0.84 mmol, 100 mol %) were combined in N,N-dimethylformamide (5.0 ml) and difluoro-fluorosulfonyl-acetic acid methyl ester (0.54 ml, 4.22 mmol, 500 mol %) was added. The reaction was heated to 100° C. under nitrogen for 6 h and then additional difluoro-fluorosulfonyl-acetic acid methyl ester (0.54 ml, 4.22 mmol, 500 mol %) was added. The reaction was then heated at the same temperature for 16 h and then cooled and diluted with water. The mixture was extracted three times with ethyl acetate and the combined organics were dried over sodium sulfate and concentrated to a residue. This material was purified by column chromatography (heptane/ethyl acetate gradient) and the starting chloride was recovered and recycled. After two cycles, a sufficient amount of 5-nitro-4-(4-o-tolyl-piperazin-1-yl)-2-trifluoromethyl-benzoic acid methyl ester 9a (212.9 mg; 0.50 mmol, 59.6%) was obtained. LCMS (ESI) 424 (M+H).

Step 2: To a solution of 5-nitro-4-(4-o-tolyl-piperazin-1-yl)-2-trifluoromethyl-benzoic acid methyl ester 9a (212.9 mg, 0.50 mmol, 100 mol %) in ethanol (5.0 ml) and tetrahydrofuran (2.0 ml) was added palladium on carbon (5 wt %) (107.0 mg, 0.05 mmol, 10 mol %) and the reaction was stirred at room temperature for 16 h and then filtered through a pad of Celite. The filtrate was then concentrated to a residue that was purified by column chromatography (dichloromethane to 10% methanol/dichloromethane) to afford 5-amino-4-(4-o-tolyl-piperazin-1-yl)-2-trifluoromethyl-benzoic acid methyl ester 9b (139.5 mg, 0.36 mmol) as an off-white solid. LCMS (ESI) 394 (M+H).

Step 3: 5-Amino-4-(4-o-tolyl-piperazin-1-yl)-2-trifluoromethyl-benzoic acid methyl ester 9b (139.5 mg, 0.36 mmol, 100 mol %) was dissolved in tetrahydrofuran (6.0 ml), methanol (3.0 ml), and water (3.0 ml) and lithium hydroxide (25.5 mg, 1.06 mmol, 300 mol %) was added. The reaction was heated at 60° C. for 4 h and then diluted with water and acidified to pH 4 with 2N aqueous hydrochloric acid. The mixture was then extracted three times with dichloromethane and the combined organic extracts were dried over sodium sulfate and concentrated to a solid 5-amino-4-(4-o-tolyl-piperazin-1-yl)-2-trifluoromethyl-benzoic acid 9c that was used in the next step without additional purification. LCMS (ESI) 378 (M−H).

Step 4: To a solution of 5-amino-4-(4-o-tolyl-piperazin-1-yl)-2-trifluoromethyl-benzoic acid 9c (160.0 mg, 0.42 mmol, 100 mol %), 1-(3-amino-propyl)-pyrrolidin-2-one 1e (0.30 ml, 2.11 mmol, 500 mol %) and N,N-diisopropylethylamine (0.22 ml, 1.26 mmol, 300 mol %) in N,N-dimethyl-formamide (3.0 ml) was added HATU (240.5 mg, 0.63 mmol, 150 mol %) and the reaction was stirred for 16h at room temperature. The reaction was then diluted with water and the mixture was extracted three times with ethyl acetate. The combined organics were then dried over sodium sulfate and concentrated to a sticky solid 9d that was used crude in the next step.

Step 5: This material was dissolved in N,N-dimethyl-formamide (3.0 ml) and treated with 2-cyclopropyl-oxazole-4-carboxylic acid 1h (77.5 mg, 0.51 mmol, 120 mol %), N,N-diisopropylethylamine (0.22 ml, 1.26 mmol, 300 mol %) and then HATU (240.5 mg, 0.63 mmol, 150 mol %) and the reaction was stirred for 16 h at 80° C. The reaction was then cooled and diluted with water and the mixture was extracted three times with ethyl acetate. The combined organics were dried over sodium sulfate and concentrated to a residue that was purified by column chromatography (dichloromethane to 10% methanol/dichloromethane) to afford 2-cyclopropyl-oxazole-4-carboxylic acid [5-[3-(2-oxo-pyrrolidin-1-yl)-propylcarbamoyl]-2-(4-o-tolyl-piperazin-1-yl)-4-trifluoromethyl-phenyl]-amide 9e (73.7 mg; 0.12 mmol, 27.4%, 2 steps) as an off-white solid.

LCMS (ESI) 639 (M+H);

$^1$H NMR (400 MHz, DMSO-d6) δ ppm 1.03-1.21 (m, 4H) 1.62-1.76 (m, 2H) 1.87-1.97 (m, 2H) 2.17-2.27 (m, 2H) 2.32 (s, 3H) 3.05-3.15 (m, 8H) 3.16-3.27 (m, 4H) 3.33-3.40 (m, 2H) 6.95-7.07 (m, 1H) 7.11-7.17 (m, 1H) 7.19-7.26 (m, 2H) 7.61-7.76 (m, 1H) 8.43-8.57 (m, 2H) 8.74 (s, 1H) 10.05-10.20 (m, 1H).

EXAMPLE 10A

Synthetic route towards 2-cyclopropyl-oxazole-4-carboxylic acid [1-oxo-2-[3-(2-oxo-pyrrolidin-1-yl)-propyl]-6-(4-o-tolyl-piperazin-1-yl)-1,2,3,4-tetrahydro-isoquinolin-7-yl]-amide 10e

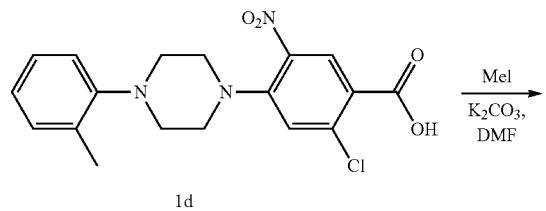

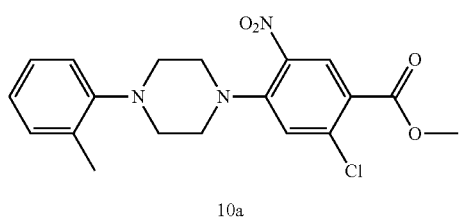 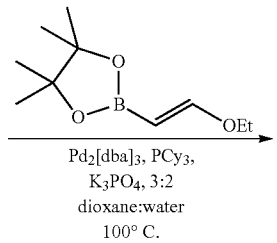

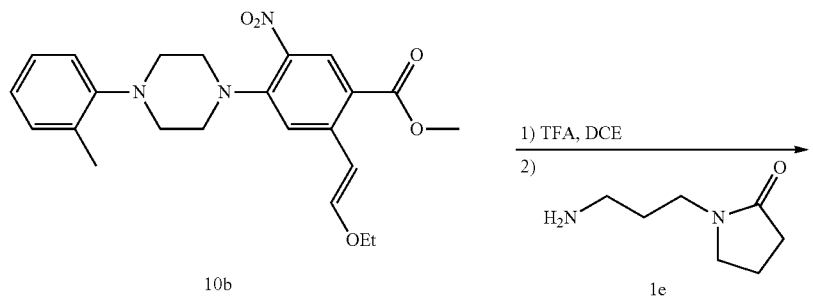

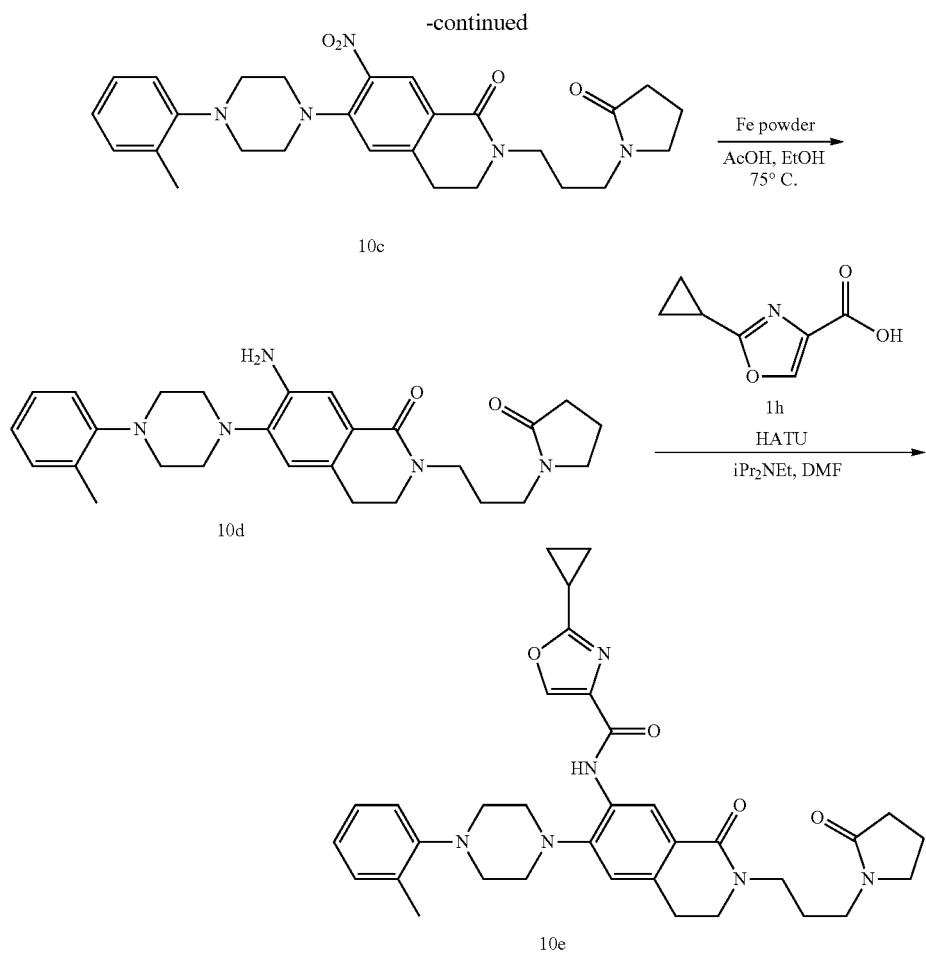

Step 1: In a 250 ml round bottom flask equipped with a magnetic stir bar, the potassium carbonate (2.06 g, 14.91 mmol) was suspended in clean, dry N,N-dimethylformamide (50.00 ml, 645.74 mmol) and the mixture was stirred together under nitrogen at room temperature as the 2-chloro-5-nitro-4-(4-o-tolyl-piperazin-1-yl)-benzoic acid 1d (2.54 g, 6.76 mmol) was added in one portion. The mixture was stirred until it appeared all the organic solids were in solution and then iodomethane (0.46 ml, 7.39 mmol) was added. The reaction was diluted with 100 ml of water and the product was extracted from the aqueous using ethyl acetate (3×100 ml). The layers were separated and the organic phases were combined, washed with brine (1×150 ml) and saturated aqueous lithium chloride solution (2×150 ml). The solution was then dried over $Na_2SO_4$; the solution was decanted and the solvent was removed under reduced pressure. The compound was purified using silica gel column chromatography, eluting a gradient of 100% heptanes to 75% ethyl acetate in heptane. 2-Chloro-5-nitro-4-(4-o-tolyl-piperazin-1-yl)-benzoic acid methyl ester 10a (2.45 g, 6.27 mmol) was isolated as a yellowish-white solid and was carried on without further purification. LCMS (m/e)=390 (M+H).

Step 2: In a 10 ml round bottom flask equipped with a magnetic stir bar and a nitrogen inlet, the 2-chloro-5-nitro-4-(4-o-tolyl-piperazin-1-yl)-benzoic acid methyl ester 10a (115.70 mg, 0.30 mmol) was combined dry with the tricyclohexylphosphine (20.00 mg, 0.07 mmol) and was then taken up in clean, dry 1,4-dioxane (0.75 ml, 8.77 mmol) and the mixture was stirred at room temperature under nitrogen atmosphere until all solids were in solution. While that was stirring, the potassium phosphate tribasic (126.00 mg, 0.59 mmol) was dissolved in water (0.50 ml, 27.75 mmol) and once complete dissolution was achieved, the basic solution was added to the stirring dioxane solution. The reaction mixture was then placed under vacuum for 10 min and was then flushed with nitrogen. The 2-((E)-2-ethoxy-vinyl)-4,4,5,5-tetramethyl-[1,3,2]dioxaborolane (64.60 mg, 0.33 mmol) was added to the solution, and the system was degassed once more. After flushing the system with nitrogen once more, the tris(dibenzylideneacetone)dipalladium (27.00 mg, 0.03 mmol) was added in one portion and the flask was fitted with a jacketed reflux condenser and the system was purged under vacuum once more. The reaction mixture system was then flushed with nitrogen and warmed to 100° C. The reaction was allowed to stir overnight under nitrogen at elevated temperatures. The reaction was cooled to room temperature and the mixture was filtered through Celite, washing heavily with ethyl acetate. The liquid filtrate was then collected and the solvent was removed under reduced pressure, absorbing the residue onto Celite. The product was then purified using silica gel column chromatography, eluting a gradient of 100% heptanes to 75% ethyl acetate in heptane. The product 2-((E)-2- ethoxy-vinyl)-5-nitro-4-(4-o-tolyl-piperazin-1-yl)-benzoic acid methyl ester 10b (97.10 mg, 0.23 mmol), was isolated as an off-white, slightly yellowish solid. LCMS (m/e)=426 (M+H).

Step 3: In a 40 ml scintillation vial equipped with a magnetic stir bar, the 2-((E)-2-ethoxy-vinyl)-5-nitro-4-(4-o-tolyl-piperazin-1-yl)-benzoic acid methyl ester 10b (97.10 mg, 0.23 mmol) was taken up in clean, dry 1,2-dichloroethane (2.00 ml, 25.38 mmol) and the mixture was stirred together at room temperature under a nitrogen atmosphere until all solids were in solution. The solution was then cooled to 0° C. using a wet ice bath and the trifluoroacetic acid (0.10 ml, 1.35 mmol) was added slowly. The reaction was allowed to warm to room temperature over an hour. The volatiles were then removed from the reaction mixture under reduced pressure. The resultant deep amber oil was taken up in 2 ml of dichloroethane and once again the volatiles were removed under reduced pressure. The resultant dark-colored semi-solid was then taken back up in 1,2-dichloroethane (2.00 ml, 25.38 mmol) and to this was added the 1-(3-amino-propyl)-pyrrolidin-2-one 1e (0.08 ml, 0.57 mmol) followed by the triethylamine (0.08 ml, 0.57 mmol) and the reaction mixture was stirred for 5 min at room temperature under an inert nitrogen atmosphere. The sodium triacetoxyborohydride (165.50 mg, 0.78 mmol) was added in one portion and the mixture stirred until all solids were in solution. The reaction mixture was then warmed to 60° C. and allowed to stir overnight under an inert nitrogen atmosphere. The reaction was cooled to room temperature and diluted with 10 ml of water along with 10 ml of dichloromethane. The layers were separated and the product was extracted from the aqueous layer using dichloromethane (3×10 ml). The organic phases were combined, washed with brine (1×25 ml) and dried over $MgSO_4$. The product solution was filtered under vacuum and the product solution was then concentrated under reduced pressure. The resultant amber oil was then purified using silica gel column chromatography, eluting a gradient of 100% dichloromethane to 5% MeOH in dichloromethane. 7-nitro-2-[3-(2-oxo-pyrrolidin-1-yl)-propyl]-6-(4-o-tolyl-piperazin-1-yl)-3,4-dihydro-2H-isoquinolin-1-one 10c (71.80 mg, 0.15 mmol) was isolated as an off-white solid and was carried on without further purification. LCMS (m/e)=492 (M+H).

Step 4: In a 25 ml round-bottom flask equipped with a magnetic stir bar, the iron powder (204.00 mg, 3.65 mmol) was suspended in clean, dry ethanol (8.00 ml, 137.01 mmol) at room temperature under an inert nitrogen atmosphere. To this was added the 7-nitro-2-[3-(2-oxo-pyrrolidin-1-yl)-propyl]-6-(4-o-tolyl-piperazin-1-yl)-3,4-dihydro-2H-isoquinolin-1-one 10c (71.80 mg, 0.15 mmol) dissolved in 1 ml of ethanol followed by the addition of acetic acid (2.00 ml, 34.94 mmol). The reaction mixture was warmed to 75° C. and was allowed to stir overnight. The reaction was cooled to room temperature and the mixture was filtered through Celite, washing with methanol. The collected solution was then concentrated under reduced pressure. The resultant ruby red oil was then diluted with 50 ml of ethyl acetate and the solution was neutralized with 30 ml of saturated $NaHCO_{3\,(aq)}$ solution. The layers were then separated and the product was extracted from the aqueous using ethyl acetate (3×30 ml). The organic phases were combined, washed with brine (1×50 ml) and dried over $Na_2SO_4$. The solution was then decanted and the solvent was removed under reduced pressure. The product was then purified from the ruby red concentrate using silica gel column chromatography, eluting a gradient of 100% dichloromethane to 10% MeOH in dichloromethane. The product, 7-amino-2-[3-(2-oxo-pyrrolidin-1-yl)-propyl]-6-(4-o-tolyl-piperazin-1-yl)-3,4-dihydro-2H-isoquinolin-1-one 10d (48.10 mg, 0.10 mmol), was isolated as an off-white solid and was carried forward without further purification. LCMS (m/e)=462 (M+H).

Step 5: In a 40 ml scintillation vial equipped with a magnetic stir bar and fitted with a nitrogen inlet, the 7-amino-2-[3-(2-oxo-pyrrolidin-1-yl)-propyl]-6-(4-o-tolyl-piperazin-1-yl)-3,4-dihydro-2H-isoquinolin-1-one 10d (48.10 mg, 0.10 mmol) was taken up in clean, dry N,N-dimethylformamide (2.00 ml, 25.83 mmol) and the mixture was stirred at room temperature and under an inert nitrogen atmosphere until all solids were in solution. To this was added the HATU (47.50 mg, 0.12 mmol) followed by the N,N-diisopropylethylamine (0.04 ml, 0.23 mmol) and the mixture was stirred until all solids were in solution. The reaction mixture was allowed to stir for 15 min and then the 2-cyclopropyl-oxazole-4-carboxylic acid 1h (20.70 mg, 0.14 mmol) was added in one portion. The reaction was then allowed to stir overnight at room temperature. The reaction was diluted with 10 ml of water and 10 ml of ethyl acetate. The layers were separated and the product was extracted from the aqueous with ethyl acetate (3×15 ml). The organic phases were combined, washed with brine (1×25 ml) and then with saturated lithium chloride aqueous solution (2×15 ml). The organic solution was then dried over $Na_2SO_4$; the solution was then decanted and the solvent was removed under reduced pressure. The product was purified using silica gel column chromatography, eluting with a gradient of 100% dichloromethane to 7.5% MeOH in dichloromethane. A secondary purification was undertaken using reverse-phase prep HPLC, eluting a gradient of 30% MeOH in water to 100% MeOH over a five minute period. The product, 2-cyclopropyl-oxazole-4-carboxylic acid [1-oxo-2-[3-(2-oxo-pyrrolidin-1-yl)-propyl]-6-(4-o-tolyl-piperazin-1-yl)-1,2,3,4-tetrahydro-isoquinolin-7-yl]-amide 10e (6.10 mg, 0.01 mmol), was isolated as a slightly off-white solid.

LCMS (m/e)=597 (M+H);

$^1$H NMR (CHLOROFORM-d) δ: 9.75 (s, 1H), 9.04 (s, 1H), 8.13 (s, 1H), 7.20-7.26 (m, 2H), 7.14-7.19 (m, 1H), 7.04 (t, J=7.3 Hz, 1H), 6.99 (s, 1H), 3.51-3.64 (m, 4H), 3.42-3.50 (m, 2H), 3.32-3.39 (m, 2H), 3.15-3.23 (m, 4H), 3.06-3.14 (m, 4H), 2.97 (t, J=6.5 Hz, 2H), 2.31-2.45 (m, 5H), 1.99-2.14 (m, 3H), 1.90 (quin, J=7.2 Hz, 2H), 1.05-1.21 (m, 4H).

EXAMPLE 10B

Synthetic route towards 2-Cyclopropyl-oxazole-4-carboxylic acid [(S)-2-((2R,3S)-2,3-dihydroxy-cyclohexyl)-1-oxo-6-(4-o-tolyl-piperazin-1-yl)-1,2,3,4-tetrahydro-isoquinolin-7-yl]-amide

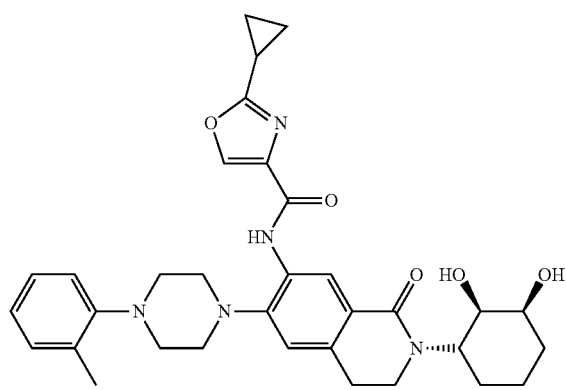

Step 1: Compound (S)-2-((3aR,7aS)-2,2-dimethyl-hexahydro-benzo[1,3]dioxol-4-yl)-7-nitro-6-(4-o-tolyl-piperazin-1-yl)-3,4-dihydro-2H-isoquinolin-1-one was prepared in the same procedure as compound 10c above (cf. Example 10A).

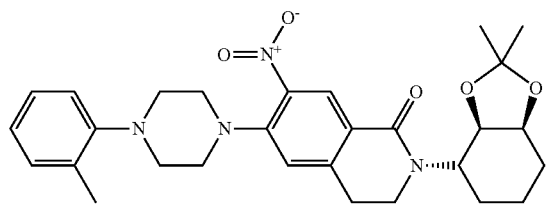

LCMS: 521.3 (M+H)$^+$;

$^1$H NMR (400 MHz, DMSO-d$_6$) δ 8.21 (s, 1H), 7.24 (s, 1H), 7.18-7.14 (m, 2H), 7.06 (d, J=7.2 Hz, 1H), 6.99-6.95 (m, 1H), 4.56-4.54 (m, 1H), 4.27 (br, s, 1H), 4.15-4.12 (m, 1H), 3.56-3.46 (m, 2H), 3.26-3.24 (m, 4H), 2.96-2.94 (m, 6H), 2.28 (s, 3H), 2.07-2.02 (m, 1H), 1.72-1.62 (m, 1H), 1.57-1.48 (m, 4H), 1.45 (s, 3H), 1.23 (s, 3H).

Step 2: To a stirred solution (S)-2-((3aR,7aS)-2,2-dimethyl-hexahydro-benzo[1,3]dioxol-4-yl)-7-nitro-6-(4-o-tolyl-piperazin-1-yl)-3,4-dihydro-2H-isoquinolin-1-one (0.53 g, 1.01 mmol) in ethyl acetate (40 mL) was charged Pd/C (20%, 0.106 g) under N$_2$ atmosphere. The reaction mixture was allowed to stir at room temperature under H$_2$ bladder for 5 h. The starting material consumption was monitored by the TLC. Upon completion of the reaction, the reaction mass was filtered through celite bed. Solvent removed under vacuo. The crude product (S)-7-amino-2-((3aR,7aS)-2,2-dimethyl-hexahydro-benzo[1,3]dioxol-4-yl)-6-(4-o-tolyl-piperazin-1-yl)-3,4-dihydro-2H-isoquinolin-1-one was as such taken for next step without purification.

Yield (0.35 g, 71%, off white solid).

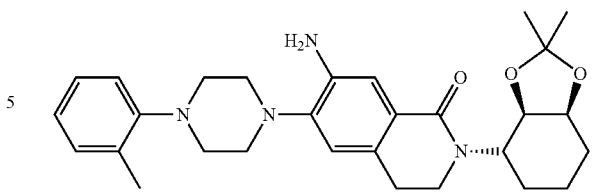

LCMS: 491.3 (M+H)$^+$;

$^1$H NMR (400 MHz, DMSO-d$_6$) δ 7.24 (s, 1H), 7.18-7.14 (m, 2H), 7.07 (d, J=7.4 Hz, 1H), 6.97-6.94 (m, 1H), 6.81 (s, 1H), 4.77 (s, 2H), 4.54-4.52 (m, 1H), 4.26 (br, s, 1H), 4.12-4.09 (m, 1H), 3.47-3.33 (m, 2H), 3.01-2.99 (m, 9H), 2.75 (br, s, 2H), 2.27 (s, 3H), 2.02-1.95 (m, 1H), 1.72-1.63 (m, 1H), 1.55-1.47 (m, 2H), 1.44 (s, 4H), 1.23 (s, 3H).

Step 3: Compound 2-Cyclopropyl-oxazole-4-carboxylic acid [(S)-2-((3aR,7aS)-2,2-dimethyl-hexahydro-benzo[1,3]dioxol-4-yl)-1-oxo-6-(4-o-tolyl-piperazin-1-yl)-1,2,3,4-tetrahydro-isoquinolin-7-yl]-amide was prepared in the same procedure as compound 10e above (cf. Example 10A).

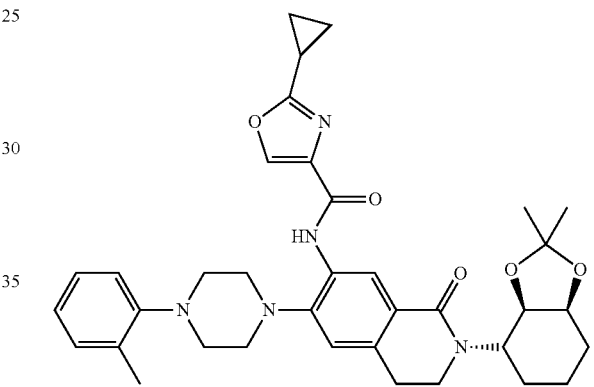

LCMS: 626.4 (M+H)$^+$;

$^1$H NMR (400 MHz, DMSO-d$_6$) δ 9.84 (s, 1H), 8.81 (s, 1H), 8.67 (s, 1H), 7.26 (s, 1H), 7.20-7.19 (m, 2H), 7.13 (d, J=7.4 Hz, 1H), 7.01-7.0 (m, 1H), 4.65-4.54 (s, 1H), 4.28 (br, s, 1H), 4.13-4.09 (m, 1H), 3.54-3.41 (m, 2H), 3.31-3.30 (br, s, 1H), 3.10-3.08 (m, 4H), 3.05-3.03 (m, 4H), 2.90-2.86 (m, 2H), 2.30 (s, 3H), 2.20-2.17 (m, 1H), 2.02-1.97 (m, 1H), 1.73-1.61 (m, 2H), 1.60-1.44 (m, 5H), 1.23 (s, 3H), 1.13-1.09 (m, 2H), 1.07-1.04 (m, 2H).

Step 4: To a stirred solution of 2-cyclopropyl-oxazole-4-carboxylic acid [(S)-2-((3aR,7aS)-2,2-dimethyl-hexahydro-benzo[1,3]dioxol-4-yl)-1-oxo-6-(4-o-tolyl-piperazin-1-yl)-1,2,3,4-tetrahydro-isoquinolin-7-yl]-amide (0.165 g, 0.26 mmol) in anhydrous methanol (2 mL) was added methanolic HCl (5 mL) at 0° C. under N$_2$ atmosphere. The reaction mixture was allowed to stir at room temperature for 1 h. The progress of the reaction was monitored by the TLC. Upon completion of the reaction, the reaction mixture was concentrated in vacuo, residue obtained was diluted with dichloromethane (100 mL); and was washed with 10% NaHCO$_3$ solution, water followed by brine solution and dried over anhydrous Na$_2$SO$_4$. The crude product obtained was purified by the flash column chromatography (230-400 size mesh) by eluting 3.25-3.5% methanol in dichloromethane to afford the title compound. Finally, the title compound 2-cyclopropyl-oxazole-4-carboxylic acid [(S)-2-((2R,3S)-2,3-dihydroxy-cyclohexyl)-1-oxo-6-(4-o-tolyl-piperazin-1-yl)-1,2,3,4-tetrahydro-isoquinolin-7-yl]-amide was purified again by preparative HPLC to afford the pure compound. Yield (0.110 g, 65%, off white solid).

LCMS: 586.3 (M+H)+;

$^1$H NMR (400 MHz, DMSO-d6) δ 9.82 (s, 1H), 8.81 (s, 1H), 8.66 (s, 1H), 7.24 (s, 1H), 7.20-7.18 (m, 2H), 7.13 (d, J=7.6 Hz, 1H), 7.01-6.97 (m, 1H), 4.70-4.64 (br, s, 1H), 4.44 (d, J=2.8 Hz, 1H), 4.32 (d, J=7.0 Hz, 1H), 3.92 (s, 1H), 3.49-3.40 (m, 3H), 3.10-3.08 (m, 4H), 3.04-3.02 (m, 4H), 2.92-2.78 (m, 2H), 2.30 (s, 3H), 2.20-2.16 (m, 1H), 1.73-1.67 (m, 2H), 1.58-1.43 (m, 2H), 1.41-1.36 (m, 2H), 1.12-1.09 (m, 2H), 1.07-1.05 (m, 2H).

In a similar chemistry as mentioned above, the following compound was prepared:

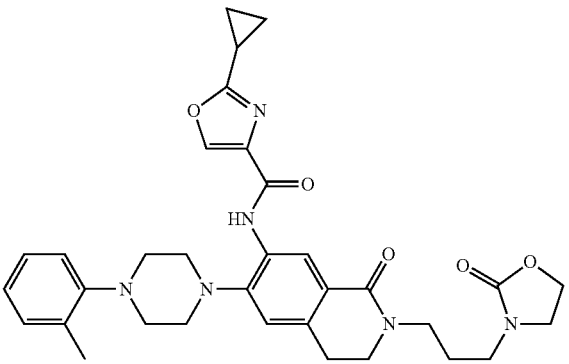 [SMILES: Cc1ccccc1N1CCN(c2cc3c(cc2NC(=O)c2coc(C4CC4)n2)C(=O)N(CCCN2CCOC2=O)CC3)CC1]

2-Cyclopropyl-oxazole-4-carboxylic acid [1-oxo-2-[3-(2-oxo-oxazolidin-3-yl)-propyl]-6-(4-o-tolyl-piperazin-1-yl)-1,2,3,4-tetrahydro-isoquinolin-7-yl]-amide.

EXAMPLE 11A

Synthetic route towards furan-2-carboxylic acid [2-(3-dimethylaminomethyl-benzyl)-1-oxo-6-(4-o-tolyl-piperazin-1-yl)-1,2,3,4-tetrahydro-isoquinolin-7-yl]-amide 11c

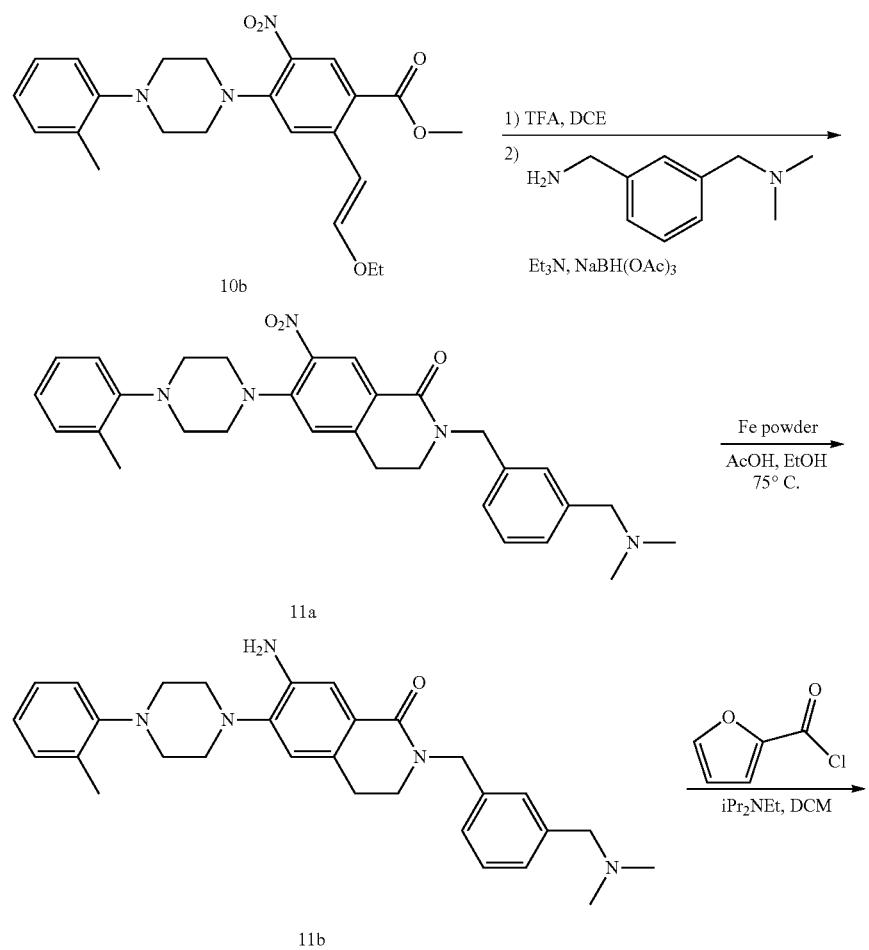

-continued

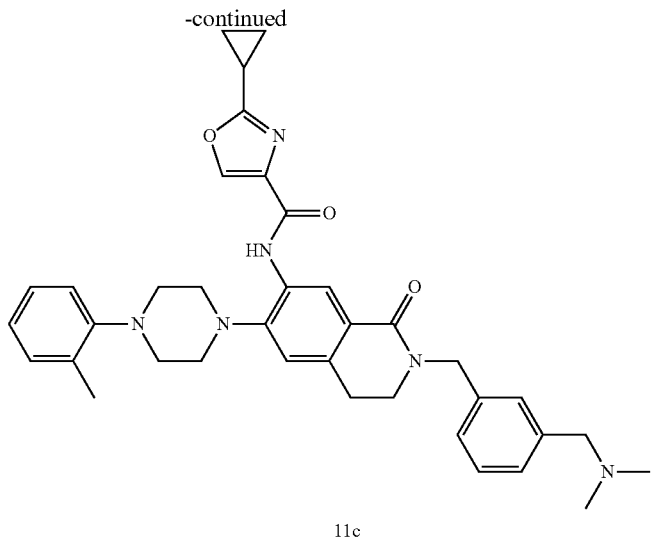

11c

Step 1: In a 25 ml round bottom flask equipped with a magnetic stir bar and fitted with a septum containing a nitrogen inlet, the 2-((E)-2-ethoxy-vinyl)-5-nitro-4-(4-o-tolyl-piperazin-1-yl)-benzoic acid methyl ester 10b (209.90 mg, 0.49 mmol) was taken up in clean, dry 1,2-dichloroethane (3.50 ml, 44.42 mmol) and was stirred at room temperature under nitrogen until all solids were in solution. To this was slowly added the trifluoroacetic acid (0.80 ml, 10.77 mmol) and the reaction was stirred at room temperature for 30 min. After 30 min., the volatiles were removed from the solution under reduced pressure. The resultant red-orange oil was taken up in 5 ml of DCE and the volatiles were removed under reduced pressure once more. The red-orange semi-solid was then taken up in 1,2-dichloroethane (3.50 ml, 44.42 mmol) and stirred vigorously under nitrogen. The 3-dimethylaminomethyl-benzylamine (202.60 mg, 1.23 mmol) was added to the solution followed by the triethylamine (0.17 ml, 1.22 mmol) and the mixture was stirred until a homogeneous solution was achieved. The sodium triacetoxyborohydride (365.90 mg, 1.73 mmol) was added to the reaction mixture and the reaction was warmed to 60° C. and was stirred under nitrogen. The reaction stirred at elevated temperatures overnight. The reaction was cooled to room temperature and the reaction mixture was diluted with 10 ml of dichloromethane and with 10 ml of water. The product was then extracted from the aqueous layer using dichloromethane (3×10 ml) and the organic phases were combined, washed with brine (1×25 ml) and the solution was then dried over $MgSO_4$. The product solution was then filtered under vacuum and the collected solution was further concentrated under reduced pressure. The product was purified using silica gel column chromatography, eluting a gradient of 100% dichloromethane to 10% MeOH in dichloromethane. The product, 2-(3-dimethylaminomethyl-benzyl)-7-nitro-6-(4-o-tolyl-piperazin-1-yl)-3,4-dihydro-2H-isoquinolin-1-one 11a (140.80 mg, 0.27 mmol), was isolated as a yellowish solid and was carried on without further purification. LCMS=513 (M+H).

Step 2: In a 100 ml round bottom flask equipped with a magnetic stir bar and fitted with a septum with a nitrogen inlet, the iron powder (382.70 mg, 6.85 mmol) was suspended in clean, dry, reagent-grade ethanol (30.00 ml, 513.81 mmol) under nitrogen and at room temperature. To the stirred reaction was added the acetic acid (3.00 ml, 52.40 mmol) and the mixture was stirred to ensure homogeneity. The 2-(3-dimethylaminomethyl-benzyl)-7-nitro-6-(4-o-tolyl-piperazin-1-yl)-3,4-dihydro-2H-isoquinolin-1-one 11a (140.80 mg, 0.27 mmol) was then added in one portion and the reaction was warmed to 75° C. and allowed to stir under nitrogen for 4 h. After 4 h, the reaction was cooled to room temperature and the reaction solution was filtered through Celite, eluting heavily with methanol. The collected solution was then concentrated under reduced pressure and the solvent was removed under reduced pressure. The resultant red oil was taken up in 50 ml of ethyl acetate and washed with 50 ml of saturated $NaHCO_3$ (aq) solution. The product was then extracted from the aqueous using ethyl acetate (3×30 ml) and the organic phases were combined and washed with brine (1×100 ml). The solution was then dried over $Na_2SO_4$; the solution was decanted and the solvent was removed under reduced pressure. The resultant brown solid was then purified using silica gel column chromatography, eluting a gradient of 100% dichloromethane to 10% MeOH in dichloromethane. 7-amino-2-(3-dimethylaminomethyl-benzyl)-6-(4-o-tolyl-piperazin-1-yl)-3,4-dihydro-2H-isoquinolin-1-one 1 b (73.70 mg, 0.15 mmol) was isolated as a tan solid and was carried on without further purifications. LCMS (m/e)=483 (M+H).

In a 40 ml scintillation vial equipped with a magnetic stir bar and fitted with a nitrogen inlet, the 7-amino-2-(3-dimethylaminomethyl-benzyl)-6-(4-o-tolyl-piperazin-1-yl)-3,4-dihydro-2H-isoquinolin-1-one 11b (73.70 mg, 0.15 mmol) was taken up in clean, dry, reagent-grade dichloromethane (3.00 ml, 46.52 mmol) and the mixture was stirred at room temperature under nitrogen atmosphere until the solids were all in solution. To this stirred solution was then added the N,N-diisopropylethylamine (0.08 ml, 0.46 mmol) followed by the furan-2-carbonyl chloride (0.02 ml, 0.20 mmol) and the reaction was allowed to stir overnight. The reaction was quenched with 3 ml of 2N HCl. The product solution was diluted with 10 ml of water and 10 ml of dichloromethane. The layers were separated and the product was extracted using dichloromethane (3×10 ml). The organic phases were combined and washed with brine (1×25 ml) and the product solution was then dried over $MgSO_4$. The solution was then filtered under vacuum and the collected solution was concentrated under reduced pressure. The resultant yellow oil was then purified using silica gel column chromatography, eluting 100% dichloromethane to 7.5% MeOH in dichloromethane. The product needed further purification and was subjected to reverse-phase HPLC, eluting a gradient of 30% MeOH in water to 100% MeOH over a 5 min period. Furan-2-carboxylic acid [2-(3-dimethylaminomethyl-benzyl)-1-oxo-6-(4-o-tolyl-piperazin-1-yl)-1,2,3,4-tetrahydro-isoquinolin-7-yl]-amide 11c (11.30 mg, 0.02 mmol) was isolated as a white solid.

LCMS=569;
$^1$H NMR (CHLOROFORM-d) δ: 9.21 (s, 1H), 9.13 (s, 1H), 7.55 (s, 1H), 7.28-7.40 (m, 6H), 7.24 (s, 2H), 7.13 (d, J=7.8 Hz, 1H), 7.05 (t, J=7.3 Hz, 1H), 7.01 (s, 1H), 6.58 (dd, J=3.3, 1.6 Hz, 1H), 4.82 (s, 2H), 4.59 (s, 2H), 3.44-3.55 (m, 3H), 3.17 (br s, 5H), 3.13 (d, J=5.2 Hz, 4H), 2.93 (t, J=6.5 Hz, 2H), 2.36 (s, 4H), 1.57 (br s, 6H).

EXAMPLE 11B

Synthetic route towards 2-cyclopropyl-oxazole-4-carboxylic acid-[1-oxo-2-[3-(2-oxo-oxazolidin-3-yl)-propyl]-6-(4-o-tolyl-piperazin-1-yl)-1,2,-dihydro-isoquinolin-7-yl]-amide

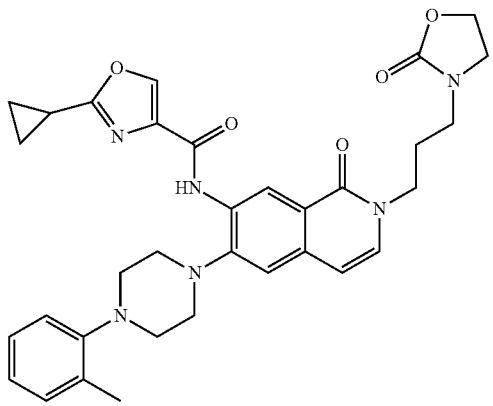 [SMILES: Cc1ccccc1N1CCN(c2cc3ccn(CCCN4CCOC4=O)c(=O)c3cc2NC(=O)c2coc(C3CC3)n2)CC1]

Step 1: To a pre-cooled solution of 1,3-dibromopropane (23.1 g, 114 mmol) in anhydrous DMSO (10 mL), powdered potassium hydroxide (1.67 g, 29.8 mmol) was added followed by 2-oxazolidinone (2.0 g, 22.9 mmol) portionwise over a period of 15 min. The reaction mixture was allowed to stir at room temperature overnight. The starting material consumption was monitored by TLC. After completion of the reaction, solvent was removed in vacuo and the residue obtained was diluted with water and extracted in ethyl acetate (3×75 mL). The combined extract was washed with water, brine solution and dried over anhydrous Na$_2$SO$_4$. The organic layer was evaporated under reduced pressure to afford the required product 3-(3-bromo-propyl)-oxazolidin-2-one. Yield (3.8 g, 80%; and colorless liquid).

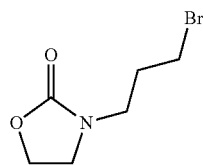

LCMS: 210.0 (M+2H)$^+$;
$^1$H NMR (400 MHz, CDCl$_3$) δ 4.36-4.31 (m, 2H), 3.63-3.59 (m, 2H), 3.45-3.39 (m, 4H), 2.17-2.14 (m, 2H).

Step 2: A cooled mixture of fuming nitric acid (2.5 mL) and conc. sulfuric acid (25 mL) was slowly added to 4-fluoro-2-methyl-benzoic acid (9 g, 58.3 mmol) at 0° C. under N$_2$ atmosphere over a period of 45 min. Reaction mixture was allowed to stir at 0° C. for 1 h. Starting material consumption was monitored by the TLC. Upon completion of the reaction the reaction mass was poured onto crushed ice and extracted in ethyl acetate (3×100 mL). Combined extract was washed with water, brine solution and dried over anhydrous Na$_2$SO$_4$. The solid obtained was washed with pet ether to afford the pure product 4-fluoro-2-methyl-5-nitro-benzoic acid.

Yield (7.8 g, 67%; and off-color solid).

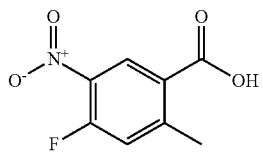

LCMS: 198.0 (M−H)$^+$;
$^1$H NMR (400 MHz, DMSO-d$_6$) δ 13.60 (br, s, 1H), 8.52 (d, J=8.0 Hz, 1H), 7.61 (d, J=12.5 Hz, 1H), 2.61 (s, 3H).

Step 3: To a stirred solution of 4-fluoro-2-methyl-5-nitro-benzoic acid (5.0 g, 25.10 mmol) in anhydrous DMF (100 mL), potassium carbonate (10.4 g, 75.3 mmol) was added under N$_2$ atmosphere followed by 1-o-tolyl-piperazine 2 HCl (8.13 g, 32.6 mmol). The reaction mixture was allowed to stir at room temperature overnight. The progress of the reaction was checked by TLC, upon completion of the reaction, solvent was removed in vacuo. The residue obtained was acidified with conc. HCl (≈pH=2-3). Yellow solid obtained was filtered and washed with water (3×75 mL), diethyl ether and dried under vacuo to obtain the pure product 2-methyl-5-nitro-4-(4-o-tolyl-piperazin-1-yl)-benzoic acid. Yield (6.5 g, 73%; and yellow solid).

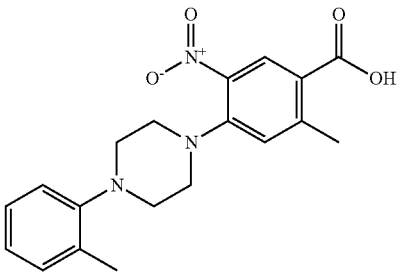 [SMILES: Cc1cc(N2CCN(c3ccccc3C)CC2)c([N+](=O)[O-])cc1C(=O)O]

LCMS: 356.0 (M+H)$^+$;
$^1$H NMR (400 MHz, DMSO-d$_6$) δ 8.32 (s, 1H), 7.21 (s, 1H), 7.19-7.14 (m, 2H), 7.09 (d, J=7.7 Hz, 1H), 7.00 (t, J=7.3 Hz, 1H), 4.64 (br, s, 1H), 3.29-3.27 (m, 4H), 2.98-2.95 (m, 4H), 2.58 (s, 3H), 2.28 (s, 3H).

Step 4: To a stirred solution of 2-methyl-5-nitro-4-(4-o-tolyl-piperazin-1-yl)-benzoic acid (6.2 g, 17.4 mmol) in anhydrous dichloromethane (170 mL), 1,1'-carbonyldiimidazole (7.07 g, 43.6 mmol) was added at 0° C. under N$_2$ atmosphere. The reaction mixture was allowed to stir at room temperature for 2 h. Where upon a solution of ammonia in THF (≈4M) was added slowly at 0° C. under N$_2$ atmosphere. The reaction mixture was allowed to stir at room temperature overnight. After the completion of the reaction as monitored by the TLC, solvent was removed in vacuo. Residue obtained was diluted with dichloromethane/methanol (150 mL, 9:1 by volume), and washed with water. Aqueous layer was again extracted in dichloromethane/methanol (3×50 mL). The combined extract was washed with brine solution and dried over anhydrous Na$_2$SO$_4$. The solvent was evaporated under reduced pressure to afford the pure product 2-methyl-5-nitro-4-(4-o-tolyl-piperazin-1-yl)-benzamide. Yield (6.0 g, 97%; and yellow solid).

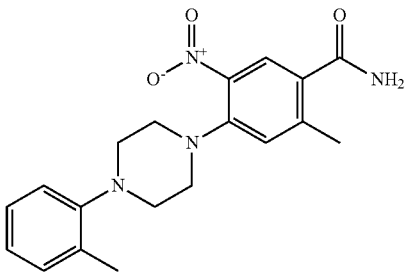 [SMILES: Cc1cc(N2CCN(c3ccccc3C)CC2)c([N+](=O)[O-])cc1C(N)=O]

LCMS: 355.0 (M+H)+;

$^1$H NMR (400 MHz, DMSO-d$_6$) δ 7.89 (s, 1H), 7.82 (br, s, 1H), 7.41 (br, s, 1H), 7.21 (s, 1H), 7.18-7.14 (m, 2H), 7.06 (d, J=7.7 Hz, 1H), 6.98 (t, J=7.3 Hz, 1H), 3.21 (t, J=4.1 Hz, 4H), 2.95 (t, J=4.4 Hz, 4H), 2.44 (s, 3H), 2.27 (s, 3H).

Step 5: A mixture of 2-methyl-5-nitro-4-(4-o-tolyl-piperazin-1-yl)-benzamide (3.0 g, 8.46 mmol) and dimethylformamide dimethyl acetal (1.32 g, 11.08 mmol) in 2-methyl tetrahydrofuran (60 mL) were heated in a Dean stark apparatus at 105° C. for 30 min. The progress of the reaction was monitored by LCMS. The volume of the reaction was reduced to half and the reaction mass was cooled to 55° C. A solution of potassium tert-butoxide (1.44 g, 12.8 mL, 12.86 mmol) in THF (1 M) was added dropwise over a period of 30 min. The reaction mixture was allowed to heat at 65° C. overnight. After completion of the reaction, solvent was removed in vacuo, residue obtained was acidified with 1.5 N HCl. The aqueous layer was extracted in dichloromethane (5×75 mL). The combined extract was washed with water, brine solution and dried over anhydrous Na$_2$SO$_4$. The crude product obtained was purified by the flash column chromatography (230-400 size mesh) using 1.0-1.25% methanol in dichloromethane to afford the compound 7-nitro-6-(4-o-tolyl-piperazin-1-yl)-2H-isoquinolin-1-one. Yield (0.25 g, 8.3%; and reddish brown solid).

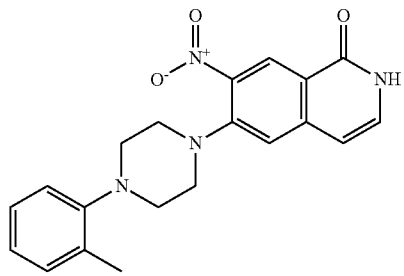 [SMILES: Cc1ccccc1N1CCN(c2cc3cc[nH]c(=O)c3cc2[N+](=O)[O-])CC1]

LCMS: 365.2 (M+H)+;

$^1$H NMR (400 MHz, DMSO-d$_6$) δ 11.36 (d, J=5.0 Hz, 1H), 8.50 (s, 1H), 7.44 (s, 1H), 7.31-7.28 (m, 1H), 7.18-7.14 (m, 2H), 7.08-7.02 (m, 1H), 6.99-6.95 (m, 1H), 6.54 (d, J=7.0 Hz, 1H), 3.21 (t, J=4.2 Hz, 4H), 2.95 (t, J=4.5 Hz, 4H), 2.27 (s, 3H).

Step 6: To a stirred solution of 7-nitro-6-(4-o-tolyl-piperazin-1-yl)-2H-isoquinolin-1-one (0.25 g, 0.68 mmol) in anhydrous DMF (10 mL), 3-(3-bromo-propyl)-oxazolidin-2-one (0.14 g, 0.68 mmol) was added followed by potassium bis(trimethylsilyl) amide (0.27 g, 1.37 mmol) at 0° C. under N$_2$ atmosphere. The reaction mass allowed to stir at room temperature for 6 h. The progress of the reaction was monitored by LCMS analysis. Upon completion of the reaction, solvent was removed in vacuo. Residue obtained was quenched with water, and extracted in dichloromethane (3×75 mL). The combined extract was washed with water, brine solution and dried over anhydrous Na$_2$SO$_4$. The crude product obtained was purified by the flash column chromatography (230-400 size mesh) using 1.5-1.75% methanol in dichloromethane to afford the compound 7-nitro-2-[3-(2-oxo-oxazolidin-3-yl)-propyl]-6-(4-o-tolyl-piperazin-1-yl)-2H-isoquinolin-1-one. Yield (0.25 g, 75%; and off-color solid).

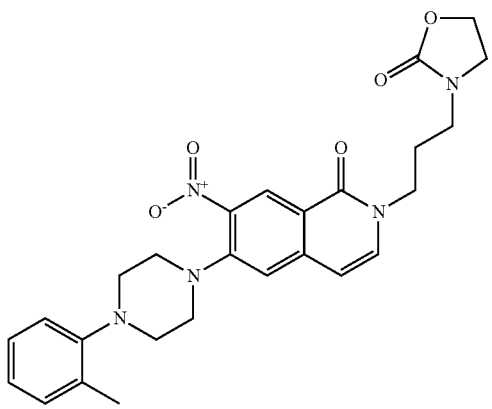 [SMILES: Cc1ccccc1N1CCN(c2cc3ccn(CCCN4CCOC4=O)c(=O)c3cc2[N+](=O)[O-])CC1]

LCMS: 492.3 (M+H)+. $^1$H NMR (400 MHz, DMSO-d$_6$) δ 8.55 (s, 1H), 7.62 (d, J=7.4 Hz, 1H), 7.44 (s, 1H), 7.18-7.14 (m, 2H), 7.07 (d, J=6.9 Hz, 1H), 6.99 (t, J=7.3 Hz, 1H), 6.62 (d, J=7.4 Hz, 1H), 4.27-4.23 (m, 2H), 3.95-3.89 (m, 2H), 3.48-3.46 (m, 2H), 3.24-3.22 (m, 4H), 3.22-3.18 (m, 2H), 2.99-2.97 (m, 4H), 2.27 (s, 3H), 1.92-1.86 (s, 2H).

Step 7: Compound 7-amino-2-[3-(2-oxo-oxazolidin-3-yl)-propyl]-6-(4-o-tolyl-piperazin-1-yl)-2H-isoquinolin-1-one was prepared in the same procedure as in the preparation of compound 11b above (cf. Example 11A).

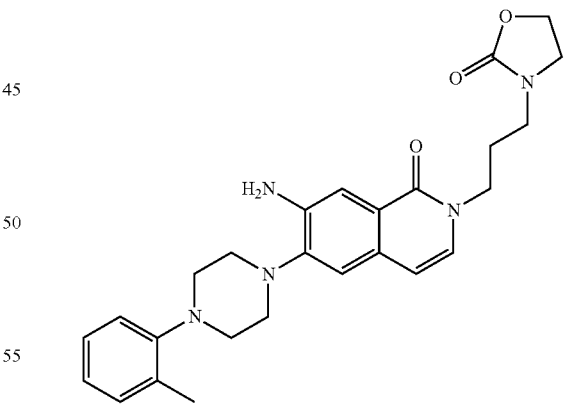

LCMS: 462.2 (M+H)+;

$^1$H NMR (400 MHz, DMSO-d$_6$) δ 7.47 (s, 1H), 7.19-7.13 (m, 4H), 7.09 (d, J=7.3 Hz, 1H), 6.98-6.95 (m, 1H), 6.44 (d, J=7.2 Hz, 1H), 5.18 (s, 2H), 4.25-4.21 (m, 2H), 3.91-3.87 (m, 2H), 3.56-3.52 (m, 2H), 3.19 (t, J=7.0 Hz, 2H), 3.05-2.98 (m, 8H), 2.29 (s, 3H), 1.91-1.82 (s, 2H).

Step 8: The title compound 2-cyclopropyl-oxazole-4-carboxylic acid-[1-oxo-2-[3-(2-oxo-oxazolidin-3-yl)-propyl]-6-(4-o-tolyl-piperazin-1-yl)-1,2,-dihydro-isoquinolin-7-yl]- amide was prepared in the same procedure as in the preparation of compound 11c above (cf. Example 11A).

LCMS: 597.3 (M+H)$^+$;

$^1$H NMR (400 MHz, DMSO-d$_6$) δ 9.97 (s, 1H), 9.15 (s, 1H), 8.71 (s, 1H), 7.58 (s, 1H), 7.44 (d, J=7.2 Hz, 1H), 7.21-7.20 (m, 2H), 7.15 (d, J=7.8 Hz, 1H), 7.02 (t, J=7.3 Hz, 1H), 6.60 (d, J=7.3 Hz, 1H), 4.26-4.22 (m, 2H), 3.97-3.93 (m, 2H), 3.57-3.53 (m, 2H), 3.23-3.15 (m, 2H), 3.12-3.11 (m, 8H), 2.31 (s, 3H), 2.22-2.18 (m, 1H), 1.93-1.88 (m, 2H), 1.14-1.10 (m, 2H), 1.08-1.06 (m, 2H).

EXAMPLE 11C

Alternative synthetic route towards 2-cyclopropyl-oxazole-4-carboxylic acid-[1-oxo-2-[3-(2-oxo-oxazolidin-3-yl)-propyl]-6-(4-o-tolyl-piperazin-1-yl)-1,2,-dihydro-isoquinolin-7-yl]-amide

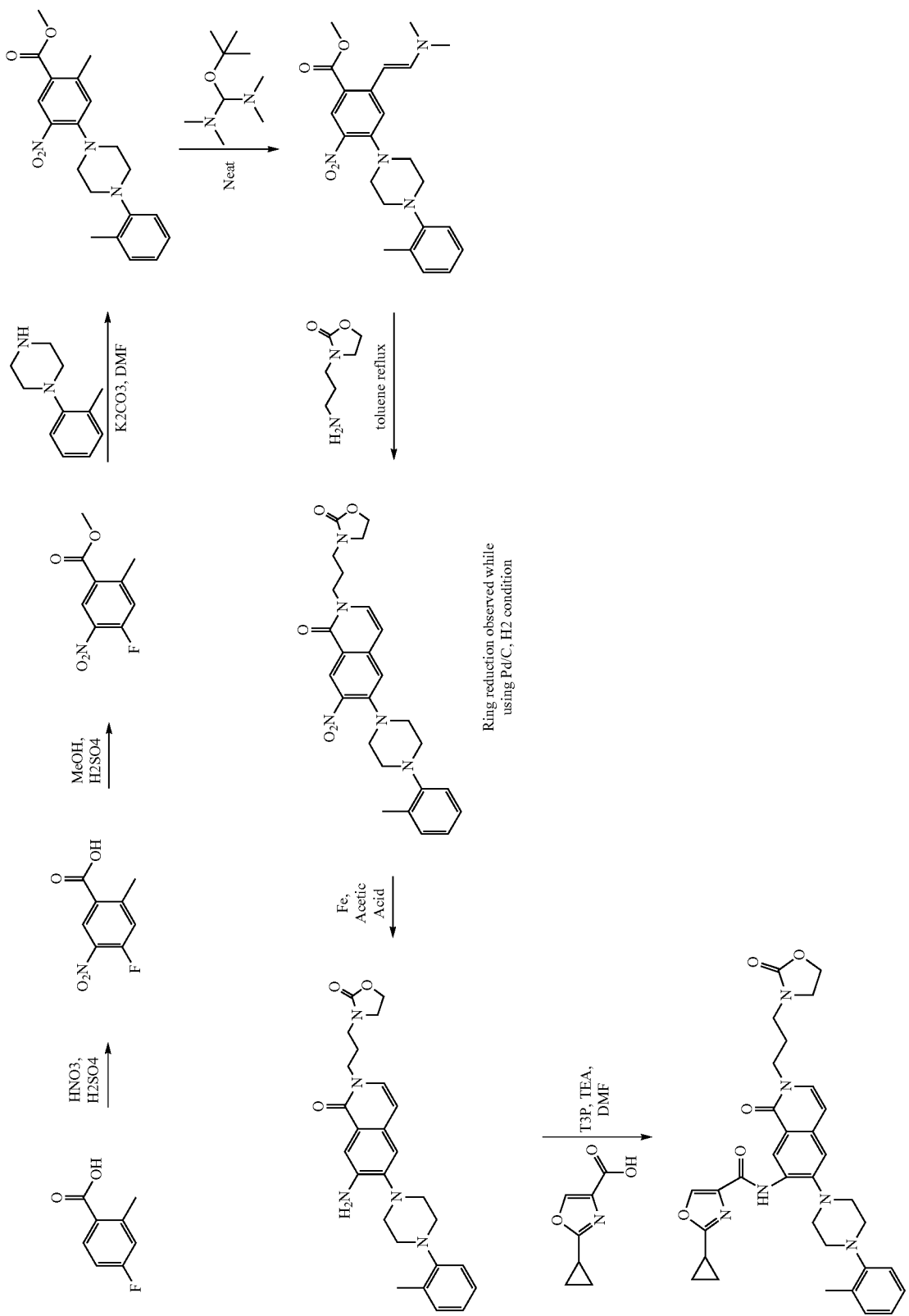

EXAMPLE 12

Synthetic route towards 2-cyclopropyl-oxazole-4-carboxylic acid {4-chloro-2-[4-(2,5-dimethyl-phenyl)-piperazin-1-yl]-5-[3-(2-oxo-pyrrolidin-1-yl)-propylcarbamoyl]-phenyl}-amide 12e Step 1: In a 100 ml round bottom flask equipped with a magnetic stir bar and fitted with a nitrogen inlet, the potassium carbonate (947.00 mg, 6.85 mmol) was suspended in clean, dry N,N-dimethylformamide (5.00 ml, 64.57 mmol) and the suspension was stirred at room temperature under nitrogen. To this was added the 2-chloro-4-fluoro-5-nitro-

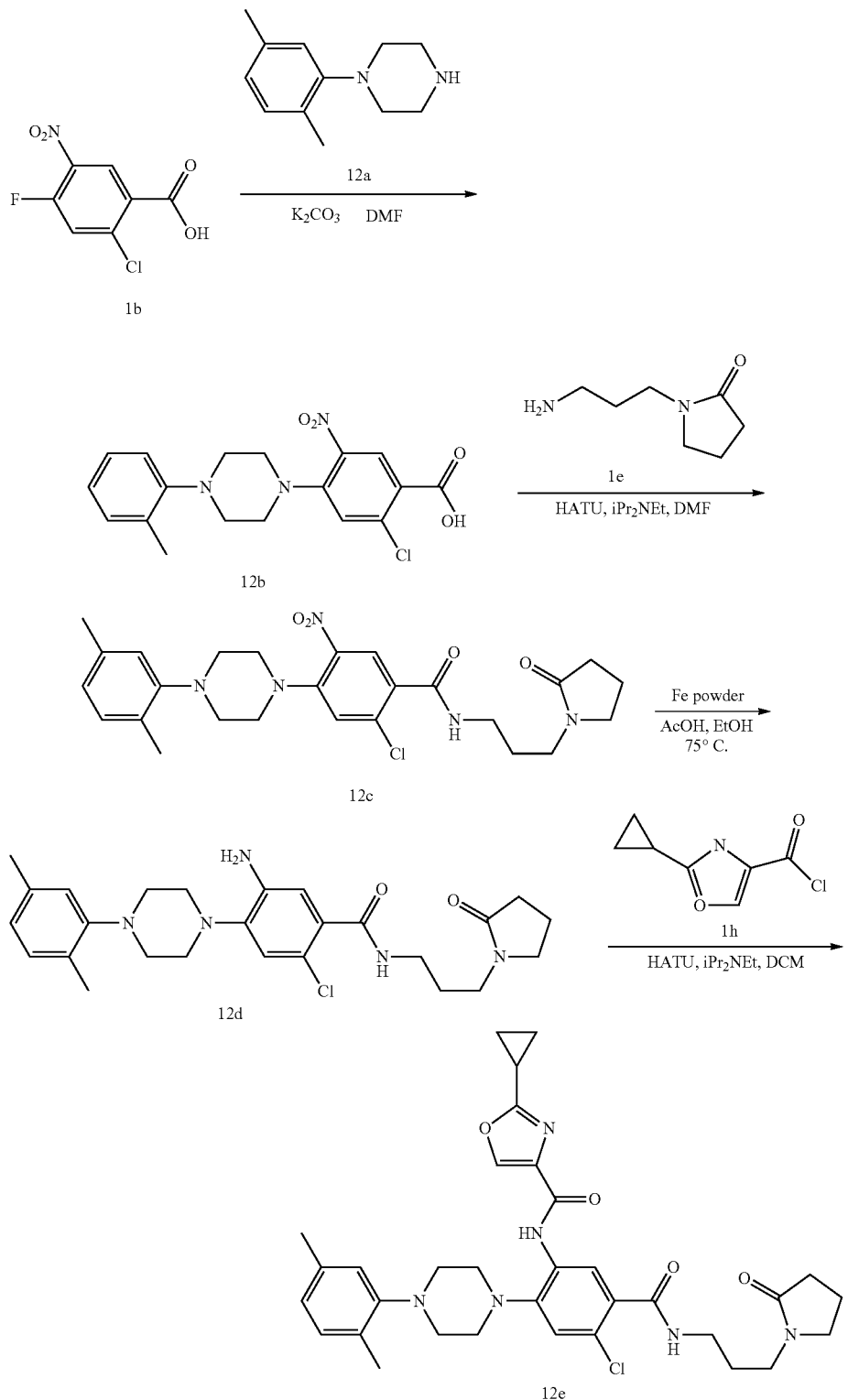

benzoic acid 1b (724.60 mg, 3.30 mmol) and the reaction mixture was allowed to stir until it appeared all the organic solids had gone into solution. To this stirred solution was then added the 1-(2,5-dimethyl-phenyl)-piperazine 12a (752.20 mg, 3.95 mmol) in one portion. The reaction solution immediately turned orange. The reaction was allowed to stir at room temperature overnight. The reaction was diluted with 10 ml of water followed by 5 ml of 2N HCl. An orange solid began crashing out of solution as the pH dropped, and the solid was collected by vacuum filtration. The collected yellow solid was then washed with water and dried under high vacuum to afford the desired compound, 2-chloro-4-[4-(2,5-dimethyl-phenyl)-piperazin-1-yl]-5-nitro-benzoic acid 12b (987.30 mg, 2.53 mmol), as a yellow powder. LCMS (m/e)=390 (M+H). Compound was carried forward without further purification.

Step 2: In a 40 ml scintillation vial equipped with a magnetic stir bar and a nitrogen inlet, the 2-chloro-4-[4-(2,5-dimethyl-phenyl)-piperazin-1-yl]-5-nitro-benzoic acid 12b (165.90 mg, 0.43 mmol) was taken up in clean, dry N,N-dimethylformamide (5.00 ml, 64.57 mmol) and was stirred under an inert nitrogen atmosphere at room temperature until all solids were in solution. To this was added the HATU (194.10 mg, 0.51 mmol) followed by the N,N-diisopropylethylamine (0.15 ml, 0.86 mmol) and the reaction mixture was stirred until all solids were in solution. The 1-(3-aminopropyl)-pyrrolidin-2-one 1e (0.08 ml, 0.57 mmol) was added in one portion and the reaction was allowed to stir at room temperature overnight. The reaction was diluted with 15 ml of water and 15 ml of ethyl acetate. The layers were separated and the product was extracted from the aqueous layer with ethyl acetate (3×20 ml). The organic phases were combined, washed with brine (1×25 ml) and with saturated lithium chloride aqueous solution (2×25 ml). The solution was dried over $Na_2SO_4$; the solution was decanted and the solvent was removed under reduced pressure. The crude product, 2-chloro-4-[4-(2,5-dimethyl-phenyl)-piperazin-1-yl]-5-nitro-N-[3-(2-oxo-pyrrolidin-1-yl)-propyl]-benzamide 12c (212.90 mg, 0.41 mmol), was carried on as an amber oil without any further purification. LCMS (m/e)=515 (M=H).

Step 3: In a 250 ml round bottom flask equipped with a magnetic stir bar and fitted with a septum with a nitrogen inlet, the iron powder (578.30 mg, 10.36 mmol) was suspended in clean, dry, reagent-grade ethanol (50.00 ml, 856.34 mmol) and was stirred vigorously at room temperature under nitrogen as the acetic acid (5.00 ml, 87.34 mmol) was added. The 2-chloro-4-[4-(2,5-dimethyl-phenyl)-piperazin-1-yl]-5-nitro-N-[3-(2-oxo-pyrrolidin-1-yl)-propyl]-benzamide 12c (212.90 mg, 0.41 mmol) was added in one portion and the reaction was warmed to 75° C. The reaction was allowed to stir for 4 h. After 4 h, the reaction was cooled to room temperature and filtered through Celite, eluting with methanol. The solvent was then removed under reduced pressure and the ruby red oil was taken up in 100 ml of ethyl acetate. 100 ml of saturated $NaHCO_3$ was added to the solution. The layers were separated and the aqueous layer was extracted twice with 75 ml of ethyl acetate. The organic phases were combined and washed with brine (1×100 ml) and dried over $Na_2SO_4$. The product solution was decanted and the solvent was removed under reduced pressure. The crude product, 5-amino-2-chloro-4-[4-(2,5-dimethyl-phenyl)-piperazin-1-yl]-N-[3-(2-oxo-pyrrolidin-1-yl)-propyl]-benzamide 12d (158.70 mg, 0.33 mmol), was isolated as a brown solid and was carried on without further purification. LCMS (m/e)=485 (M+H).

Step 4: In a 40 ml scintillation vial equipped with a magnetic stir bar and fitted with a nitrogen inlet, the 5-amino-2-chloro-4-[4-(2,5-dimethyl-phenyl)-piperazin-1-yl]-N-[3-(2-oxo-pyrrolidin-1-yl)-propyl]-benzamide 12d (158.70 mg, 0.33 mmol) was taken up in clean, dry N,N-dimethylformamide (3.00 ml, 38.74 mmol) and the mixture was stirred at room temperature under an inert nitrogen atmosphere until all solids were taken up in solution. To this mixture was then added the HATU (188.20 mg, 0.49 mmol) followed by the N,N-diisopropylethylamine (0.17 ml, 0.98 mmol) and the mixture was again stirred until all solids were in solution. The 2-cyclopropyl-oxazole-4-carboxylic acid 1h (65.70 mg, 0.43 mmol) was then added to the reaction mixture and the reaction was allowed to stir under nitrogen at room temperature overnight. The reaction mixture was diluted with 15 ml of water and 15 ml of ethyl acetate. The layers were separated and the product was extracted from the aqueous solution using ethyl acetate (3×20 ml) and the organic phases were combined, washed with brine (1×25 ml) and saturated aqueous lithium chloride solution (2×25 ml). The solution was dried over $Na_2SO_4$; the product solution was decanted and the solvent was removed under reduced pressure. The resultant brown semi-solid was purified using silica gel column chromatography, eluting a gradient of 100% dichloromethane to 10% MeOH in dichloromethane. The product, 2-cyclopropyl-oxazole-4-carboxylic acid {4-chloro-2-[4-(2,5-dimethyl-phenyl)-piperazin-1-yl]-5-[3-(2-oxo-pyrrolidin-1-yl)-propylcarbamoyl]-phenyl}-amide 12e (81.80 mg, 0.13 mmol), was isolated as an off-white solid and was submitted for testing.

LCMS=618 (M+H);

$^1$H NMR (CHLOROFORM-d) δ: 9.84 (s, 1H), 8.68 (s, 1H), 8.11 (s, 1H), 7.23 (t, J=5.9 Hz, 1H), 7.19 (s, 1H), 7.10 (d, J=7.6 Hz, 1H), 6.98 (s, 1H), 6.85 (d, J=7.5 Hz, 1H), 3.32-3.51 (m, 6H), 3.14 (d, J=3.7 Hz, 4H), 3.05 (d, J=4.0 Hz, 4H), 2.34-2.41 (m, 2H), 2.33 (s, 3H), 2.30 (s, 3H), 1.98-2.14 (m, 3H), 1.76-1.89 (m, 2H), 1.17-1.27 (m, 2H), 1.07-1.16 (m, 2H).

EXAMPLE 13

Synthetic route towards 2-cyclopropyl-oxazole-4-carboxylic acid {4-chloro-5-(3-dimethylaminomethyl-benzylcarbamoyl)-2-[4-(2,5-dimethyl-phenyl)-piperazin-1-yl]-phenyl}-amide 13c

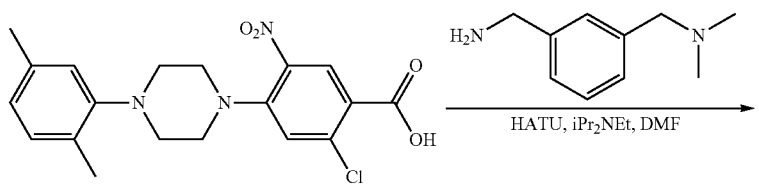

12b

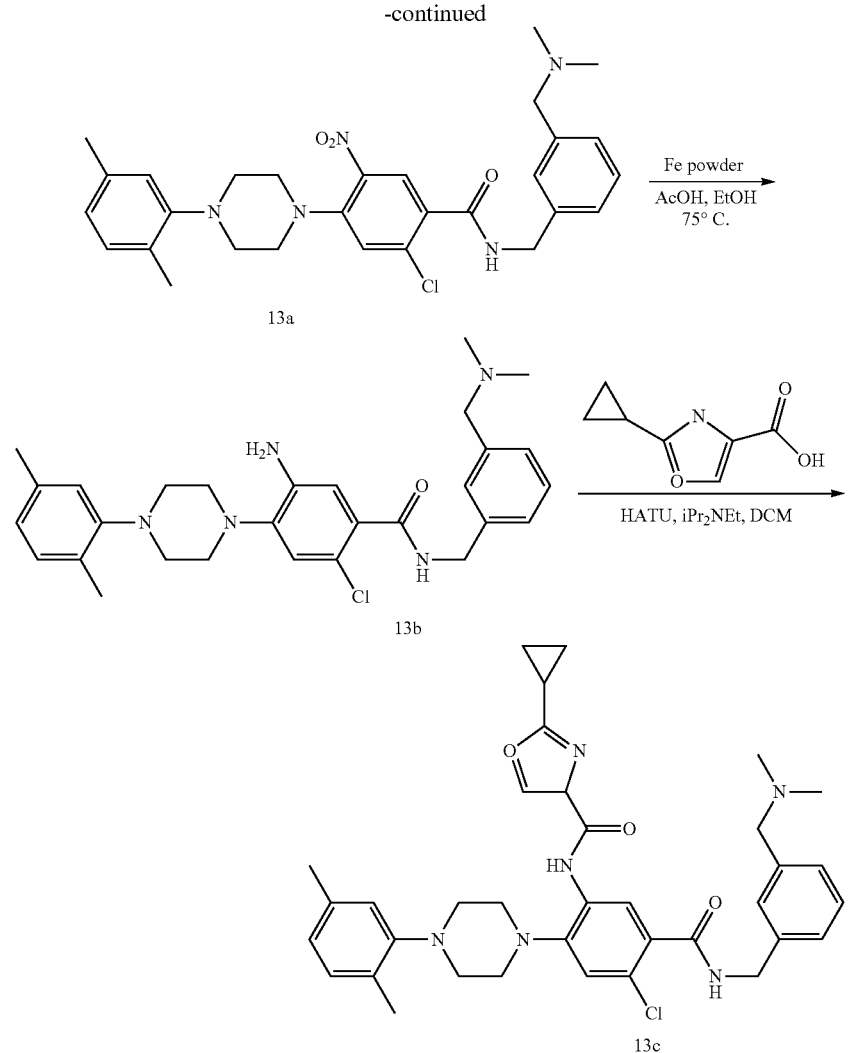

Step 1: In a 40 ml scintillation vial equipped with a magnetic stir bar and a nitrogen inlet, the 2-chloro-4-[4-(2,5-dimethyl-phenyl)-piperazin-1-yl]-5-nitro-benzoic acid 12b (157.90 mg, 0.41 mmol) was taken up in clean, dry N,N-dimethylformamide (5.00 ml, 64.57 mmol) and the reaction mixture was stirred under nitrogen at room temperature until all solids had gone into solution. To the reaction was then added the HATU (184.80 mg, 0.49 mmol) followed by the N,N-diisopropylethylamine (0.14 ml, 0.80 mmol) and the mixture was stirred until all solids had gone into solution. The 3-dimethylaminomethyl-benzylamine (86.50 mg, 0.53 mmol) was then added to the reaction solution and the reaction was allowed to stir at room temperature overnight. The reaction was diluted with 15 ml of water and 15 ml of ethyl acetate. The layers were then separated and the product was extracted from the aqueous using ethyl acetate (3×20 ml). The organic phases were combined, washed with brine (1×25 ml) and with saturated aqueous lithium chloride solution (2×25 ml). The product solution was then dried over Na₂SO₄; the solution was then decanted and the solvent was removed under reduced pressure. The crude product, 2-chloro-N-(3-dimethylaminomethyl-benzyl)-4-[4-(2,5-dimethyl-phenyl)-piperazin-1-yl]-5-nitro-benzamide 13a (214.40 mg, 0.40 mmol), was isolated as an amber oil and was carried on without further purification. LCMS (m/e)=537 (M+H).

Step 2: In a 250 ml round bottom flask equipped with a magnetic stir bar and a septum with a nitrogen inlet, the iron powder (557.40 mg, 9.98 mmol) was suspended in clean, dry, reagent-grade ethanol (50.00 ml, 856.34 mmol) and the mixture was stirred together vigorously under nitrogen at room temperature as the acetic acid (5.00 ml, 87.34 mmol) was added. The reaction continued to stir at room temperature as the 2-chloro-N-(3-dimethylaminomethyl-benzyl)-4-[4-(2,5-dimethyl-phenyl)-piperazin-1-yl]-5-nitro-benzamide 13a (214.40 mg, 0.40 mmol) was added in one portion. The reaction mixture was then warmed to 75° C. and the reaction stirred for 4 h. After 4 h, the reaction was cooled to room temperature and filtered through Celite, washing with methanol. The solvent was then removed from the filtrate under reduced pressure. The ruby red oil was then taken back up in 100 ml of ethyl acetate; an equivalent amount of saturated aqueous NaHCO₃ solution was added to the organic solution. The layers were then separated and the aqueous layer was extracted with ethyl acetate (2×75 ml). The organic phases were combined and dried over Na₂SO₄. The product solution was then decanted and the solvent was removed under reduced pressure. The crude product, 5-amino-2-chloro-N-(3-dimethylaminomethyl-benzyl)-4-[4-(2,5-dimethyl-phenyl)-piperazin-1-yl]-benzamide 13b (142.50 mg, 0.28 mmol), was isolated as a brown solid and was carried on without further purification. LCMS (m/e)=507 (M+H).

Step 3: In a 40 ml scintillation vial equipped with a magnetic stir bar and fitted with a nitrogen inlet, the 5-amino-2-chloro-N-(3-dimethylaminomethyl-benzyl)-4-[4-(2,5-dimethyl-phenyl)-piperazin-1-yl]-benzamide 13b (142.50 mg, 0.28 mmol) was taken up in clean, dry N,N-dimethylformamide (3.00 ml, 38.74 mmol) and the mixture was stirred at room temperature under nitrogen until all solids were in solution. To this stirred solution was added the HATU (159.70 mg, 0.42 mmol) followed by the N,N-diisopropylethylamine (0.15 ml, 0.86 mmol) and the mixture was again stirred at room temperature until all solids were in solution. The 2-cyclopropyl-oxazole-4-carboxylic acid 1h (55.70 mg, 0.36 mmol) was added to the mixture and the reaction was allowed to stir over night at room temperature. The reaction was diluted with 15 ml of water and 15 ml of ethyl acetate. The layers were separated and the product was extracted from the aqueous using ethyl acetate (3×20 ml). The organic phases were combined and the solution was washed with brine (1×25 ml) and with saturated aqueous lithium chloride solution (2×25 ml). The solution was then dried over Na₂SO₄; the solution was decanted and the solvent was removed under reduced pressure. The resultant brown oil was then purified using silica gel column chromatography, eluting a gradient of 100% dichloromethane to 90% dichloromethane/9% MeOH/1% NH₄OH. The desired product, 2-cyclopropyl-oxazole-4-carboxylic acid {4-chloro-5-(3-dimethylaminomethyl-benzylcarbamoyl)-2-[4-(2,5-dimethyl-phenyl)-piperazin-1-yl]-phenyl}-amide 13c (33.60 mg, 0.05 mmol), was isolated as a white solid.

LCMS (m/e)=642 (M+H);

¹H NMR (CHLOROFORM-d) δ: 9.84 (s, 1H), 8.76 (s, 1H), 8.13 (s, 1H), 7.30-7.38 (m, 3H), 7.23 (s, 2H), 7.12 (d, J=7.6 Hz, 1H), 6.99 (s, 1H), 6.87 (d, J=7.5 Hz, 1H), 6.41 (br s, 1H), 4.68 (s, 2H), 3.49 (s, 2H), 3.17 (br s, 4H), 3.08 (d, J=4.3 Hz, 4H), 2.35 (s, 3H), 2.32 (s, 3H), 2.29 (s, 6H), 2.12 (br s, 1H), 1.22 (br s, 2H), 1.16 (dd, J=8.0, 3.4 Hz, 2H).

In a similar chemistry as mentioned above, the following compounds were prepared:

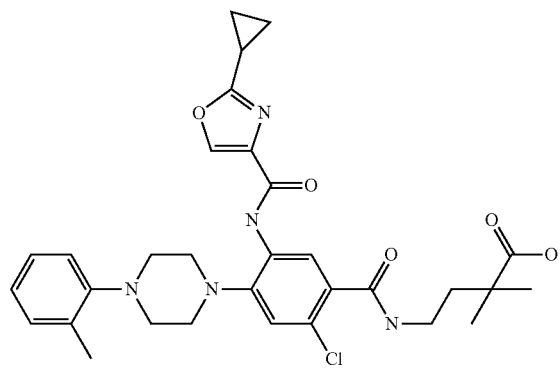 [SMILES: Cc1ccccc1N1CCN(c2cc(Cl)c(C(=O)NCCC(C)(C)C(=O)O)cc2NC(=O)c2coc(C3CC3)n2)CC1]

4-[2-Chloro-5-[(2-cyclopropyl-oxazole-4-carbonyl)-amino]-4-(4-o-tolyl-piperazin-1-yl)-benzoylamino]-2,2-dimethyl-butyric acid.

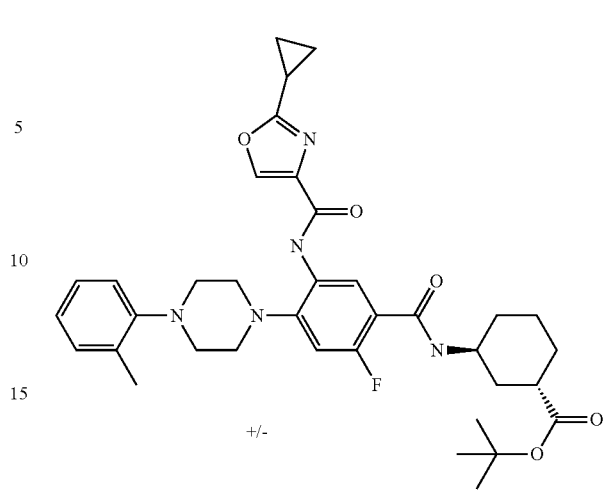

+/-

(1SR,3SR)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid tert-butyl ester.

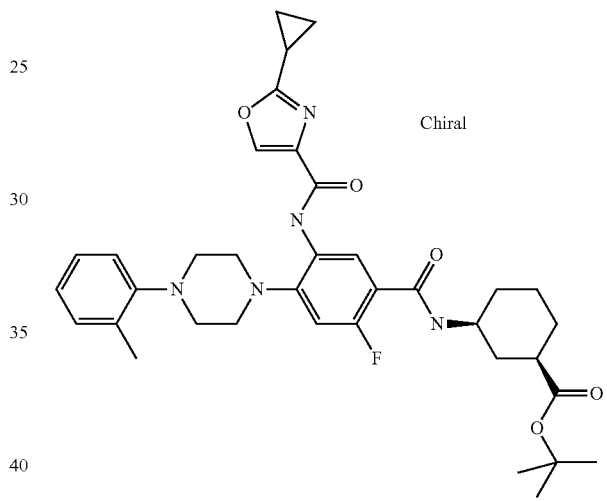

Chiral (1R,3S)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid tert-butyl ester.

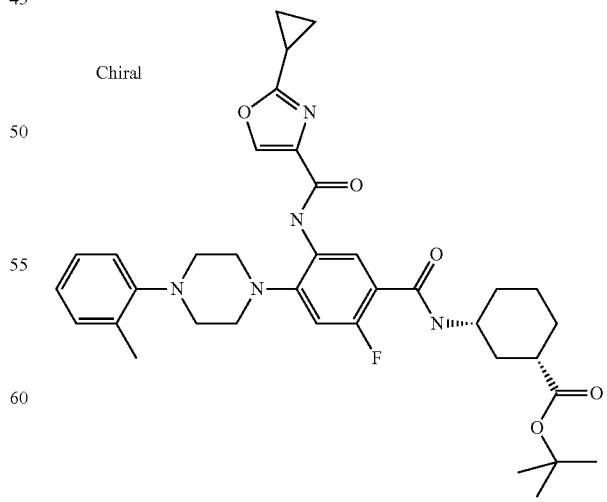

Chiral (1S,3R)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid tert-butyl ester.

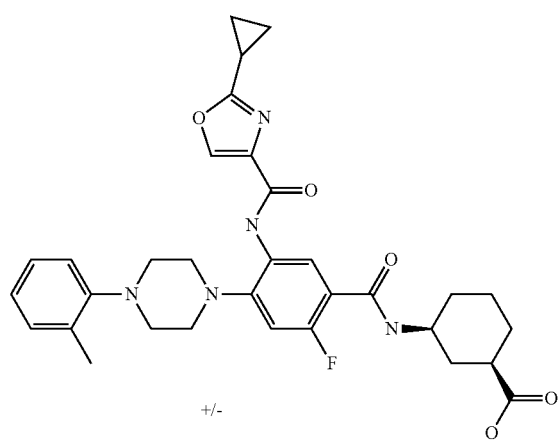 [SMILES: Cc1ccccc1N1CCN(c2cc(F)c(C(=O)N[C@H]3CCC[C@@H](C(=O)O)C3)cc2NC(=O)c2coc(C3CC3)n2)CC1]

(1RS,3SR)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid.

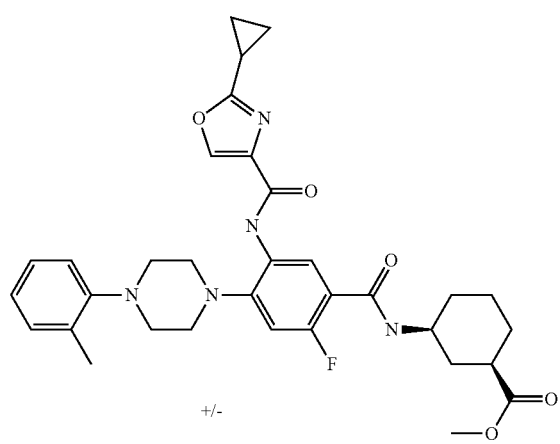 [SMILES: COC(=O)[C@@H]1CCC[C@H](NC(=O)c2cc(NC(=O)c3coc(C4CC4)n3)c(N3CCN(c4ccccc4C)CC3)cc2F)C1]

(1RS,3SR)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid methyl ester.

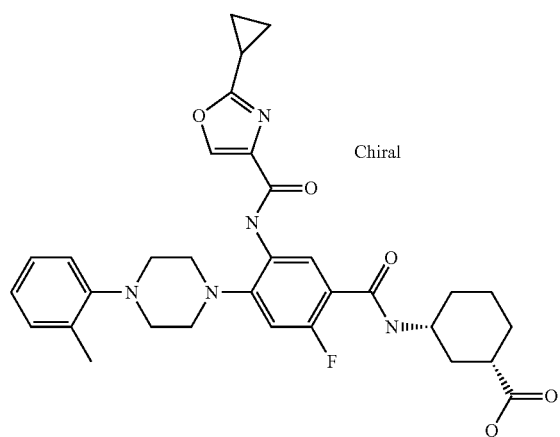 [SMILES: Cc1ccccc1N1CCN(c2cc(F)c(C(=O)N[C@@H]3CCC[C@H](C(=O)O)C3)cc2NC(=O)c2coc(C3CC3)n2)CC1]

(1S,3R)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid.

EXAMPLE 14

Synthetic route towards furan-2-carboxylic acid [4-chloro-5-(3-dimethylaminomethyl-benzylcarbamoyl)-2-(4-o-tolyl-piperazin-1-yl)-phenyl]-amide 14c

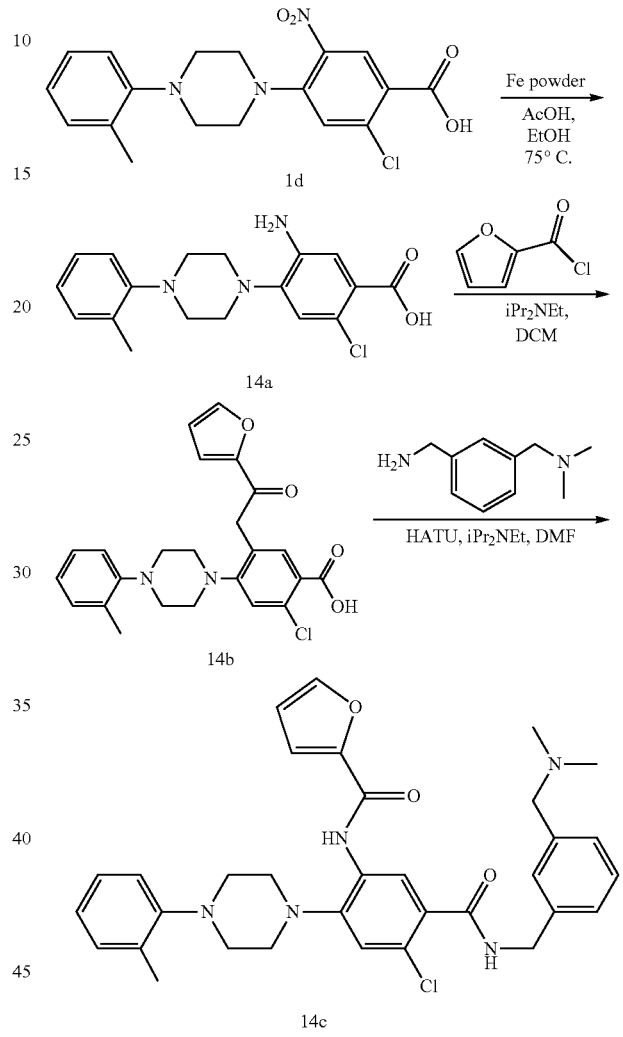

Step 1: In a 500 ml round bottom flask equipped with a magnetic stir bar, the iron powder (5.59 g, 100.15 mmol) was suspended in clean, dry, reagent-grade ethanol (300.00 ml, 5138.06 mmol) and the mixture was stirred vigorously under nitrogen at room temperature. To this was added the acetic acid (30.00 ml, 524.05 mmol) and the reaction was allowed to stir for 5 min before the 2-chloro-5-nitro-4-(4-o-tolyl-piperazin-1-yl)-benzoic acid 1d (1.51 g, 4.01 mmol) was added in one portion. The reaction was then warmed to 75° C. and allowed to stir overnight. The reaction was cooled to room temperature and was then filtered through Celite, washing heavily with methanol. The deep red product solution was then concentrated under reduced pressure and the resultant ruby red oil was taken up in 200 ml of ethyl acetate. To this solution was added 200 ml of saturated NaHCO$_3$ $_{(aq)}$ solution and the layers were then separated and the product was extracted out of the aqueous using ethyl acetate (3×100 ml). The organic phases were then combined and washed with brine (1×200 ml) and dried over $Na_2SO_4$. The solution was then decanted and the solvent was removed under reduced pressure. The crude product, 5-amino-2-chloro-4-(4-o-tolyl-piperazin-1-yl)-benzoic acid 14a (1.22 g, 3.53 mmol), was isolated as a brown solid and was carried on without further purification. LCMS=346 (M+H).

Step 2: In a 40 ml scintillation vial equipped with a magnetic stir bar and fitted with a nitrogen inlet, the 5-amino-2-chloro-4-(4-o-tolyl-piperazin-1-yl)-benzoic acid 14a (107.50 mg, 0.31 mmol) was taken up in clean, dry, reagent grade dichloromethane (5.00 ml, 77.53 mmol) and the mixture was stirred until all solids were in solution. To this stirred solution was added the N,N-diisopropylethylamine (0.16 ml, 0.92 mmol) followed by the furan-2-carbonyl chloride (0.04 ml, 0.41 mmol) and the reaction was allowed to stir at room temperature overnight. The reaction was analyzed by LCMS, which showed that mixed anhydride had formed along with the desired compound. The reaction was then concentrated under reduced pressure and taken back up in methanol and the solution was then treated with saturated $NaHCO_3$ solution and the mixture was stirred for 2 h. The mixture was then diluted with 20 ml of water and 20 ml of dichloromethane. The layers were separated and the product was extracted from the aqueous using dichloromethane (3×10 ml). The organic phases were combined, washed with brine (1×25 ml) and dried over $MgSO_4$. The solution was filtered under vacuum and the collected solution was then concentrated under reduced pressure. The product, 2-chloro-5-[(furan-2-carbonyl)-amino]-4-(4-o-tolyl-piperazin-1-yl)-benzoic acid 14b (135.70 mg, 0.31 mmol), was isolated as a yellowish solid and was carried on without further purification. LCMS (m/e)=439 (M+H).

Step 3: In a 40 ml scintillation vial equipped with a magnetic stir bar and fitted with a nitrogen inlet, the 2-chloro-5-[(furan-2-carbonyl)-amino]-4-(4-o-tolyl-piperazin-1-yl)-benzoic acid 14b (135.70 mg, 0.31 mmol) was taken up in clean, dry N,N-dimethylformamide (4.00 ml, 51.66 mmol) and the mixture was stirred at room temperature under nitrogen until all solids were in solution. To this was added first the HATU (140.80 mg, 0.37 mmol) followed by the N,N-diisopropylethylamine (0.16 ml, 0.92 mmol) and the mixture was once again stirred until all solids were in solution. The 3-dimethylaminomethyl-benzylamine (76.00 mg, 0.46 mmol) was added and the reaction stirred at room temperature overnight. The reaction was diluted with 10 ml of water and 10 ml of ethyl acetate. The layers were separated and the product was extracted from the aqueous using ethyl acetate (3×15 ml). The organic phases were combined, washed with brine (1×25 ml) and saturated aqueous lithium chloride solution (2×25 ml). The product solution was dried over $Na_2SO_4$; the solution was then decanted and the solvent was removed under reduced pressure. The product was isolated using silica gel column chromatography, eluting a gradient of 100% dichloromethane to 10% MeOH in dichloromethane. A secondary purification was required, using reverse-phase prep HPLC, eluting a gradient of 30% MeOH in water to 100% MeOH over a 5 min period. The product, furan-2-carboxylic acid [4-chloro-5-(3-dimethylaminomethyl-benzylcarbamoyl)-2-(4-o-tolyl-piperazin-1-yl)-phenyl]-amide 14c (37.30 mg, 0.06 mmol), was isolated as an off-white solid.

LCMS=587 (M+H);

$^1$H NMR (CHLOROFORM-d) δ: 9.25 (br s, 1H), 8.73 (s, 1H), 7.53-7.54 (m, 1H), 7.53 (s, 1H), 7.30 (d, J=10.8 Hz, 4H), 7.09 (d, J=8.1 Hz, 1H), 6.98-7.06 (m, 1H), 6.56 (br s, 1H), 6.30 (br s, 1H), 4.64 (d, J=5.6 Hz, 2H), 3.41 (s, 2H), 3.13 (d, J=3.6 Hz, 4H), 3.07 (br s, 4H), 2.33 (s, 3H), 2.23 (s, 6H).

EXAMPLE 15

Synthetic route towards 2-cyclopropyl-oxazole-4-carboxylic acid [4-chloro-5-[3-(2-oxo-oxazolidin-3-yl)-propylcarbamoyl]-2-(4-o-tolyl-piperazin-1-yl)-phenyl]-amide 15d

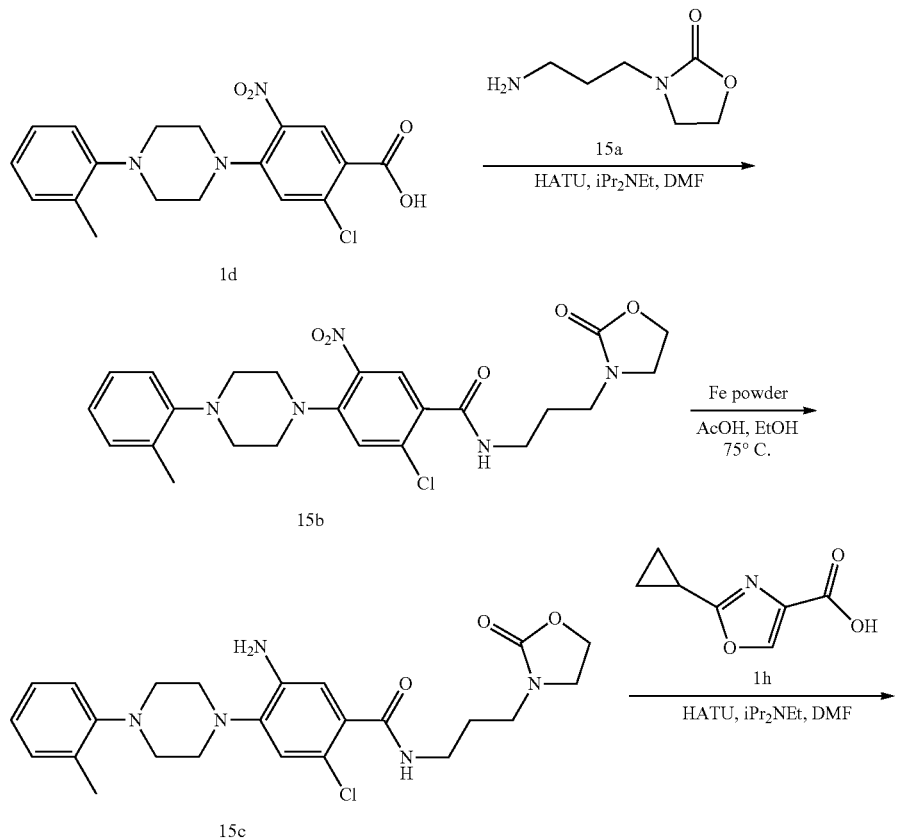

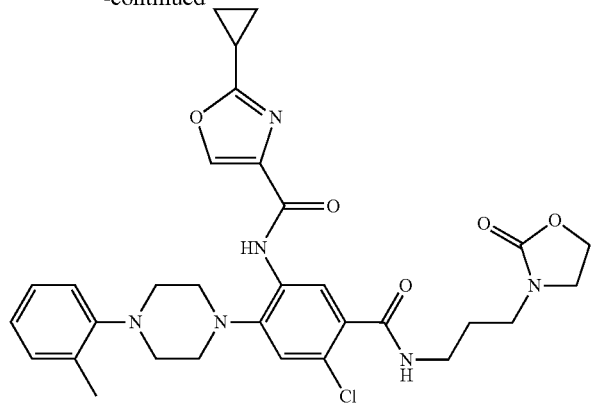

15d

Step 1: In a 40 ml scintillation vial equipped with a magnetic stir bar and fitted with a nitrogen inlet, the 2-chloro-5-nitro-4-(4-o-tolyl-piperazin-1-yl)-benzoic acid 1d (141.40 mg, 0.38 mmol) was taken up in clean, dry N,N-dimethylformamide (3.00 ml, 38.74 mmol) and the mixture was stirred together at room temperature under nitrogen atmosphere until all solids were taken up into solution. To this was added the HATU (171.70 mg, 0.45 mmol) followed by the N,N-diisopropylethylamine (0.20 ml, 1.15 mmol) and the mixture was once again stirred until all solids were in solution. Finally, the 3-(3-amino-propyl)-oxazolidin-2-one 15a (71.22 mg, 0.49 mmol) was added in one portion and the reaction was allowed to stir at room temperature overnight. The reaction was diluted with 10 ml of water and 10 ml of ethyl acetate. The layers were then separated and the product was extracted from the solution using ethyl acetate (3×15 ml). The organic phases were combined, washed with brine (1×25 ml) and saturated aqueous lithium chloride solution (2×25 ml). The solution was dried over $Na_2SO_4$; the solution was decanted and the solvent was removed under reduced pressure. The product was then purified using silica gel column chromatography, eluting a gradient of 100% dichloromethane to 10% MeOH in dichloromethane. The product, 2-chloro-5-nitro-N-[3-(2-oxo-oxazolidin-3-yl)-propyl]-4-(4-o-tolyl-piperazin-1-yl)-benzamide 15b (170.60 mg, 0.34 mmol), was isolated as an off-white solid and was carried on without further purification. LCMS=501 (M+H).

Step 2: In a 100 ml round bottom flask equipped with a magnetic stir bar and fitted with a septum with a nitrogen inlet, the iron powder (491.20 mg, 8.80 mmol) was suspended in clean, dry, reagent-grade ethanol (20.00 ml, 342.54 mmol). The suspension was stirred at room temperature and acetic acid (2.00 ml, 34.94 mmol) was added in one portion. The reaction mixture was allowed to stir to allow for homogeneity and then the 2-chloro-5-nitro-N-[3-(2-oxo-oxazolidin-3-yl)-propyl]-4-(4-o-tolyl-piperazin-1-yl)-benzamide 15b (170.60 mg, 0.34 mmol) was added to the reaction mixture. The reaction was then warmed to 75° C. and the reaction stirred at elevated temperatures under an inert nitrogen atmosphere for 4 h. After 4 h, the reaction was cooled to room temperature and the reaction mixture was filtered through Celite, washing heavily with methanol. The collected product solution was then concentrated under reduced pressure and the resultant ruby red oil was taken up in 50 ml of ethyl acetate. To the product solution was added 50 ml of saturated $NaHCO_{3\ (aq)}$ and the layers were separated. The product was extracted from the aqueous using ethyl acetate (3×25 ml). The organic phases were combined, washed with brine (1×100 ml) and dried over $Na_2SO_4$; the solution was decanted and the solvent was removed under reduced pressure. The product was then purified using silica gel column chromatography, eluting a gradient of 100% dichloromethane to 10% MeOH in dichloromethane. The desired product, 5-amino-2-chloro-N-[3-(2-oxo-oxazolidin-3-yl)-propyl]-4-(4-o-tolyl-piperazin-1-yl)-benzamide 15c (148.20 mg, 0.31 mmol), was isolated as an off-white, tannish solid. LCMS=472 (M+H).

Step 3: In a 40 ml scintillation vial equipped with a magnetic stir bar, the 5-amino-2-chloro-N-[3-(2-oxo-oxazolidin-3-yl)-propyl]-4-(4-o-tolyl-piperazin-1-yl)-benzamide 15c (73.40 mg, 0.16 mmol) was taken up in clean, dry, reagent-grade N,N-dimethylformamide (3.00 ml, 38.74 mmol) and the reaction mixture was stirred under a nitrogen feed at room temperature until all solids were in solution. To this was then added the HATU (70.90 mg, 0.19 mmol) in one portion followed by the N,N-diisopropylethylamine (0.08 ml, 0.46 mmol) and the reaction mixture was stirred until all solids were in solution. The 2-cyclopropyl-oxazole-4-carboxylic acid 1h (35.70 mg, 0.23 mmol) was added the reaction was allowed to stir at room temperature overnight. The reaction was diluted with 10 ml of water and 10 ml of ethyl acetate. The layers were separated and the product was extracted from the aqueous using ethyl acetate (3×20 ml). The organic phases were combined, washed with brine (1×25 ml) and with saturated aqueous lithium chloride solution (2×25 ml). The organic solution was then dried over $Na_2SO_4$; the solution was decanted and the solvent was removed under reduced pressure. The product was purified using silica gel column chromatography, eluting a gradient of 100% dichloromethane to 7.5% MeOH in dichloromethane. The product required further purification and was thusly subjected to reverse-phase prep-HPLC, eluting a gradient of 30% MeOH in water to 100% MeOH over a 5 min period. The product, 2-cyclopropyl-oxazole-4-carboxylic acid [4-chloro-5-[3-(2-oxo-oxazolidin-3-yl)-propylcarbamoyl]-2-(4-o-tolyl-piperazin-1-yl)-phenyl]-amide 15d (26.60 mg, 0.04 mmol), was isolated as a white solid.

LCMS=608 (M+H);

$^1$H NMR (CHLOROFORM-d) δ: 9.76 (s, 1H), 8.63 (s, 1H), 8.03 (s, 1H), 7.11-7.17 (m, 3H), 7.04-7.10 (m, 1H), 6.93-7.00 (m, 1H), 4.29 (t, J=8.0 Hz, 2H), 3.52-3.64 (m, 2H), 3.41 (q, J=6.3 Hz, 2H), 3.35 (t, J=6.4 Hz, 2H), 3.09 (d, J=4.7 Hz, 4H), 3.00 (d, J=4.7 Hz, 4H), 2.29 (s, 3H), 1.96-2.06 (m, 1H), 1.82 (t, J=6.3 Hz, 2H), 1.01-1.11 (m, 4H).

In a similar chemistry as mentioned above, the following compound was prepared:

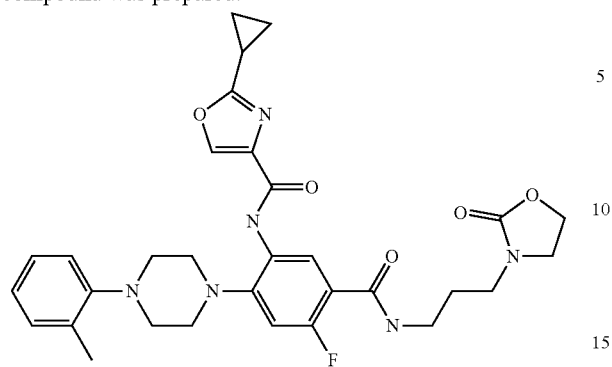

(1SR,3SR)-3-[5-[(2-Cyclopropyl-oxazole-4-carbonyl)-amino]-2-fluoro-4-(4-o-tolyl-piperazin-1-yl)-benzoylamino]-cyclohexanecarboxylic acid tert-butyl ester.

EXAMPLE 16

Synthetic route towards 2-cyclopropyl-oxazole-4-carboxylic acid {4-chloro-2-[4-(5-fluoro-2-methyl-phenyl)-piperazin-1-yl]-5-[3-(2-oxo-pyrrolidin-1-yl)-propylcarbamoyl]-phenyl}-amide 16h

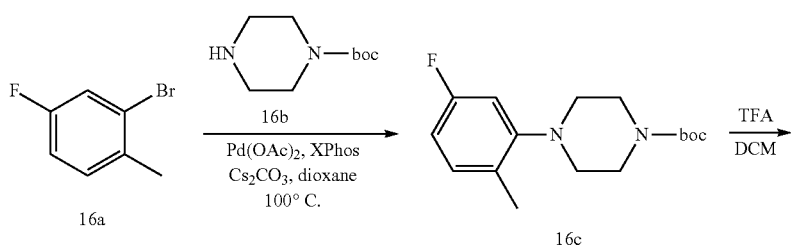

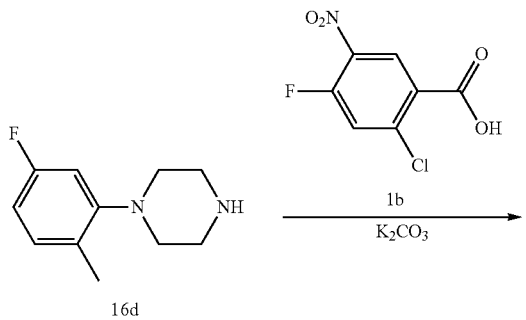

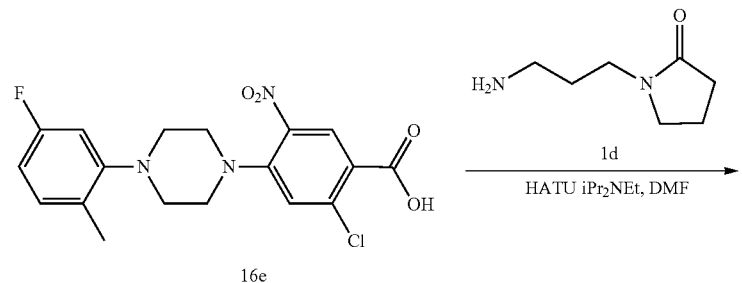

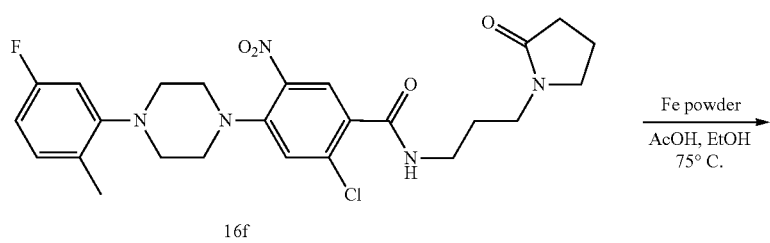

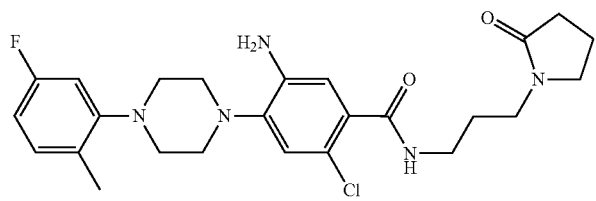
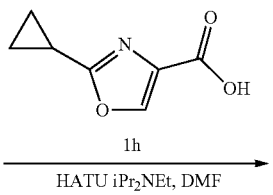

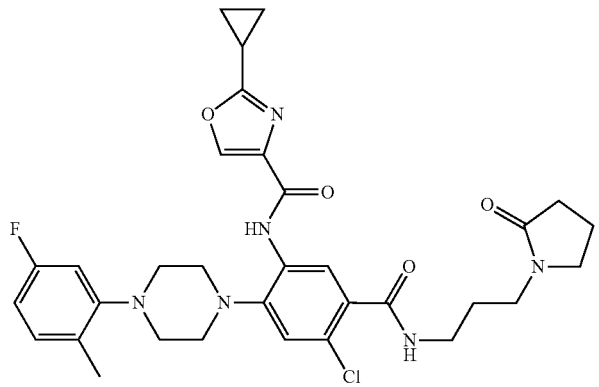

Step 1: In a 50 ml round bottom flask equipped with a magnetic stir bar and fitted with a nitrogen inlet, the XPhos (210.80 mg, 0.44 mmol) and the cesium carbonate (1.80 g, 5.52 mmol) were combined dry. This mixture was taken up in 1,4-dioxane (10.00 ml, 116.91 mmol) and the 2-bromo-4-fluoro-1-methyl-benzene 16a (1.04 g, 5.53 mmol) was added followed by the piperazine-1-carboxylic acid tert-butyl ester 16b (514.80 mg, 2.76 mmol). The mixture was stirred together under vacuum at room temperature for 10 min and then the system was flushed with nitrogen. The palladium(II) acetate (62.10 mg, 0.28 mmol) was added to the reaction in one portion and the reaction was warmed to 100° C. and was allowed to stir under nitrogen overnight. The reaction was cooled to room temperature and filtered through Celite, washing with ethyl acetate. The collected product solution was then concentrated under reduced pressure and the product was purified from the resultant dark brown oil using silica gel column chromatography, eluting a gradient of 100% heptanes to 50% ethyl acetate in heptanes. 4-(5-fluoro-2-methyl-phenyl)-piperazine-1-carboxylic acid tert-butyl ester 16c (451.00 mg, 1.53 mmol) was isolated as an off-white solid. LCMS (m/e)=295 (M+H).

Step 2: In a 20 ml scintillation vial equipped with a magnetic stir bar and fitted with a nitrogen inlet, the 4-(5-fluoro-2-methyl-phenyl)-piperazine-1-carboxylic acid tert-butyl ester 16c (203.70 mg, 0.69 mmol) was taken up in clean, dry, reagent grade dichloromethane (5.00 ml, 77.53 mmol). The mixture was stirred until all solids were in solution and the trifluoroacetic acid (0.50 ml, 6.73 mmol) was added in one portion. The reaction stirred at room temperature for 1 h. After 1 h, the volatiles were removed under reduced pressure. The yellow oil was then taken back up in 5 ml of dichloromethane and the volatiles were removed once more under reduced pressure. The resultant yellow oil was further dried under high vacuum. The product, 1-(5-fluoro-2-methyl-phenyl)-piperazine 16d (160.10 mg, 0.82 mmol), was isolated as a yellow oil and was carried on without further purification.

Step 3: In a 20 ml scintillation vial equipped with a magnetic stir bar and fitted with a nitrogen inlet, the potassium carbonate (201.60 mg, 1.46 mmol) was suspended in clean, dry N,N-dimethylformamide (2.00 ml, 25.83 mmol) and the 2-chloro-4-fluoro-5-nitro-benzoic acid 1b (160.10 mg, 0.73 mmol) was added to the reaction mixture and stirred until it appeared all the organic solid was taken up into solution. The 1-(5-fluoro-2-methyl-phenyl)-piperazine 16d (170.00 mg, 0.88 mmol) was added to the reaction and the reaction mixture was allowed to stir at room temperature under a nitrogen atmosphere overnight. The reaction mixture was diluted with 10 ml of water and treated with 10 ml of 2N HCl. The product mixture was stirred until no further gas evolved and was then filtered under vacuum. The orange solid that was collected was washed with water and dried under high vacuum. The product, 2-chloro-4-[4-(5-fluoro-2-methyl-phenyl)-piperazin-1-yl]-5-nitro-benzoic acid 16e (222.30 mg, 0.56 mmol), was isolated as a yellow solid and was carried on without further purification. LCMS (m/e)=394 (M+H).

Step 4: In a 40 ml scintillation vial equipped with a magnetic stir bar and fitted with a nitrogen inlet, the 2-chloro-4-[4-(5-fluoro-2-methyl-phenyl)-piperazin-1-yl]-5-nitro-benzoic acid 16e (110.60 mg, 0.28 mmol) was taken up in clean, dry dichloromethane (3.00 ml, 46.52 mmol) and was allowed to stir at room temperature under nitrogen until all solids were in solution. To this was then added the HATU (128.10 mg, 0.34 mmol) followed by the N,N-diisopropylethylamine (0.15 ml, 0.86 mmol) and again the mixture was stirred until all solids were dissolved. The 1-(3-amino-propyl)-pyrrolidin-2-one 1e (59.90 mg, 0.42 mmol) was added to the reaction and the mixture stirred at room temperature overnight. The reaction was diluted with 10 ml of water and 10 ml of dichloromethane. The layers were separated and the product was extracted from the aqueous using dichloromethane (3×15 ml). The organic phases were washed with brine (1×25 ml) and dried over MgSO$_4$. The solution was then filtered under vacuum and the collected solution was concentrated under reduced pressure. The resultant orange oil was purified using silica gel column chromatography, eluting a gradient of 100% dichloromethane to 10% MeOH in dichloromethane. The product, 2-chloro-4-[4-(5-fluoro-2-methyl-phenyl)-piperazin-1-yl]-5-nitro-N-[3-(2-oxo-pyrrolidin-1-yl)-propyl]-benzamide 16f (140.10 mg, 0.27 mmol), was isolated as a yellow solid and was carried forward without further purification. LCMS (m/e)=518 (M+H).

Step 5: In a 50 ml round bottom flask equipped with a magnetic stir bar and fitted with a septum and a nitrogen inlet, the iron powder (377 mg, 6.75 mmol) was suspended in clean, dry, reagent-grade ethanol (12 ml, 205.52 mmol) and allowed to stir at room temperature under nitrogen. To this was added the acetic acid (1.20 ml, 20.96 mmol) and the reaction was allowed to stir to ensure homogeneity. The 2-chloro-4-[4-(5-fluoro-2-methyl-phenyl)-piperazin-1-yl]-5-nitro-N-[3-(2-oxo-pyrrolidin-1-yl)-propyl]-benzamide 16f (140.10 mg, 0.27 mmol) was added in one portion and the reaction was warmed to 75° C. and allowed to stir for 3 h. After 3 h, the reaction was cooled to room temperature and filtered through Celite, washing heavily with methanol. The collected organic solution was then concentrated under reduced pressure and the resultant red oil was taken up in 50 ml of ethyl acetate and was washed with 50 ml of saturated NaHCO$_3$ $_{(aq)}$ solution. The product was then extracted from the aqueous using ethyl acetate (3×20 ml) and the organic phases were combined, washed with brine (1×50 ml) and dried over Na$_2$SO$_4$. The solution was then decanted, and the solvent was removed under reduced pressure. The product, 5-amino-2-chloro-4-[4-(5-fluoro-2-methyl-phenyl)-piperazin-1-yl]-N-[3-(2-oxo-pyrrolidin-1-yl)-propyl]-benzamide 16g (130 mg, 0.27 mmol), was isolated as a brown solid and carried forward without further purification. LCMS (m/e)=488 (M+H).

Step 6: In a 40 ml scintillation vial equipped with a magnetic stir bar and a fitted with a nitrogen inlet, the 5-amino-2-chloro-4-[4-(5-fluoro-2-methyl-phenyl)-piperazin-1-yl]-N-[3-(2-oxo-pyrrolidin-1-yl)-propyl]-benzamide 16g (130 mg, 0.27 mmol) was taken up in clean, dry N,N-dimethylformamide (3.00 ml, 38.74 mmol) and the mixture was allowed to stir under nitrogen at room temperature until all solids were in solution. To this mixture was added the HATU (121.60 mg, 0.32 mmol) followed by the N,N-diisopropylethylamine (0.14 ml, 0.80 mmol) and the mixture was allowed to stir until all solids were taken into solution. The 2-cyclopropyl-oxazole-4-carboxylic acid 1h (56.80 mg, 0.37 mmol) was added to the reaction mixture and the reaction stirred at room temperature overnight. The reaction was diluted with 10 ml of water and 10 ml of ethyl acetate. The layers were separated and the product was extracted from the aqueous using ethyl acetate (3×15 ml). The organic phases were combined, washed with brine (1×25 ml) and with saturated aqueous lithium chloride solution (2×25 ml). The solution was then dried over Na$_2$SO$_4$; the solution was then decanted and the solvent was removed under reduced pressure. The product was purified from the resultant brown semi-solid using silica gel column chromatography, eluting a gradient of 100% dichloromethane to 10% MeOH in dichloromethane. A secondary purification was required and the compound was purified using reverse-phase prep HPLC, eluting a gradient of 30% MeOH in water to 100% MeOH over a 5 min period. The product, 2-cyclopropyl-oxazole-4-carboxylic acid {4-chloro-2-[4-(5-fluoro-2-methyl-phenyl)-piperazin-1-yl]-5-[3-(2-oxo-pyrrolidin-1-yl)-propylcarbamoyl]-phenyl}-amide 16h (11.20 mg, 0.02 mmol), was isolated as a white solid.

LCMS (m/e)=623 (M);
$^1$H NMR (CHLOROFORM-d) δ: 9.86 (s, 1H), 8.72 (s, 1H), 8.07-8.16 (m, 1H), 7.21 (s, 1H), 7.16 (t, J=7.5 Hz, 1H), 7.09 (s, 1H), 6.88 (dd, J=10.9, 2.4 Hz, 1H), 6.71-6.79 (m, 1H), 3.38-3.50 (m, 6H), 3.16 (d, J=4.7 Hz, 4H), 3.09 (d, J=4.7 Hz, 4H), 2.40 (t, J=8.1 Hz, 2H), 2.32 (s, 3H), 2.01-2.15 (m, 3H), 1.78-1.89 (m, 2H), 1.10-1.20 (m, 4H).

EXAMPLE 17

EC$_{50}$ of Cyclic AMP Production in CHO FSHR Cells+EC$_{20}$ FSH (Assay A)

Cho-FSHR-LUC-1-1-43 cells were plated per well in 5 μl of phenol red free DMEM/F12+1% FBS. Cells were plated in 384 well, solid white low volume plates (Greiner 784075) by Multidrop. Cells were assayed by adding 100 μl of 2×EC$_{20}$ FSH/IBMX in DMEM/F12+0.1% BSA) by Multidrop to 2 μl of test compound stamped in 384 well plates (compounds are diluted 1:50). The final FSH concentration was 0.265 μM, and the final IBMX concentration was 200 μM. The compound plate map was as follows: Column 1: 2 μl of DMSO; Column 2: 2 μl of DMSO; Columns 3-12 and 13-24: 2 μl of test compound, diluted 1:4 in 100% DMSO, or 2 μl of FSH, diluted 1:4 in DMEM/F12+0.1% BSA. The starting concentration for FSH was 50 nM (final concentration was 0.5 nM). Furthermore, Column 23 contained 2 μl of EC$_{100}$ FSH reference (100×) (diluted in DMEM/F12+0.1% BSA) at a final concentration of 0.5 nM, and Column 24 contained 2 μl of 1 mM AS707664/2 reference compound 2.5 μl of compound+EC$_{20}$ FSH mixture were transferred to cell plates (1:2 dilution into 5 μl of cell media) The plates were incubated at 37° C. for 1 h. 10 μl of mixed HTRF (CisBio #62AM4PEC) reagents were added per well and incubated at room temperature for 1 h. The plates were read on Envision using the cAMP HTRF—low volume 384 well protocol. The readout was the calculated fluorescence ratio (665 nm/620 nm). Values given in percent (%) indicate the percental effect (response) at a certain concentration of agonist relative to the maximum response of the FSH standard. Results are given in Table 1.

EXAMPLE 18

Rat Granulosa EC$_{50}$ FSH (Assay B)

The assay was performed pursuant to the teaching of Yanofsky et al. (2006) Allosteric activation of the follicle-stimulating hormone (FSH) receptor by selective, nonpeptide agonists. JBC 281(19): 13226-13233, which is incorporated by reference in the disclosure of the invention. Results are given in Table 1.

EXAMPLE 19

Pharmaceutical Preparations (A) Injection vials: A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4.2H_2O$, 28.48 g of $Na_2HPO_4 \cdot 12H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to Example E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:
1. A compound of formula (I)

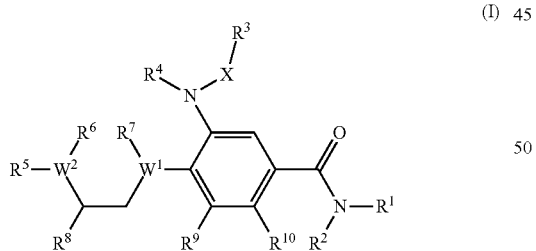

(I)

wherein
$W^1$, $W^2$ each denote independently from one another N or CH,
  with the proviso that at least one of $W^1$ or $W^2$ denotes N;
$R^1$ denotes $-(CY_2)_n$-E-Het$^3$, $-(CY_2)_n$-Cyc-Het$^3$, $-(CY_2)_n$-Het$^1$, $-(CY_2)_n$—CONH-Het$^1$, $-(CY_2)_n$—NHCO-Het$^1$, $-(CY_2)_n$—Ar, $-(CY_2)_n$-Cyc, $-(CY_2)_n$—CONH-Cyc, $-(CY_2)_n$—NHCO-Cyc, A, $-(CYR^8)_n$—OY, $-(CY_2)_n$—COOY, $-(CY_2)_n$—SO$_2$Y, $-(CYR^8)_n$—CONY$_2$, $-(CYR^8)_n$—NY$_2$, $-(CYR^8)_n$—NYCOY, $-(CY_2)_n$—NYCOOY, $-(CY_2)_n$—NY-CONY$_2$ or $-(CY_2)_n$—NHCO—CH=CH$_2$; or $R^1$, $R^2$ together denote $-(CY_2)_p$—NH—$(CY_2)_p$—, $-(CY_2)_p$—NHCO—$(CY_2)_p$—, $-(CY_2)_p$—CONH—$(CY_2)_p$—, $-(CY_2)_p$—N(COA)-$(CY_2)_p$—, $-(CY_2)_p$—N(COOA)-$(CY_2)_p$—,

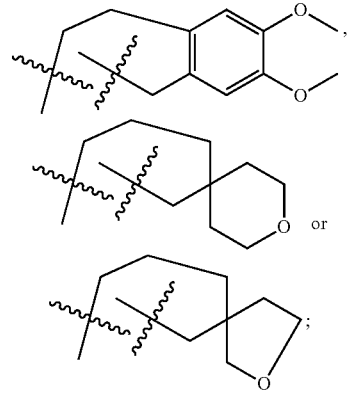

$R^3$ denotes $-(CY_2)_n$-Het$^1$, $-(CY_2)_n$-Het$^3$, $-(CY_2)_n$—Ar, H, A or $-(CY_2)_n$-Cyc;
$R^4$, $R^9$ each denote independently from one another Y;
$R^5$ denotes E-Ar, H, A, COOY, SO$_2$Y, Het$^1$ or Het$^3$;
$R^2$, $R^6$, $R^7$ each denote independently from one another H; or
$R^6$, $R^7$ together denote $-(CY_2)_p$—;
$R^8$ denotes Y or Ar;
$R^{10}$ denotes Hal, Y, OY, —O(CY$_2$)$_n$—OY, NY$_2$, Cyc, COOY, CONH$_2$, NHCOY or CN;
  with the proviso that both $R^9$ and $R^{10}$ are not H; or
$R^2$, $R^{10}$ together denote $-(CY_2)_p$— or $-(CY)_2$—;
X denotes O, CO, —COO— or SO$_2$;
each E denote independently from one another $-(CY_2)_m$—, O, CO, —COO— or SO$_2$;
each Y is independently H or A;
each A is independently unbranched or branched alkyl having 1-10 C atoms, in which 1-7 H atoms can be replaced independently from one another by Hal and/or =O;
each Cyc is independently cycloalkyl having 3-7 C atoms, in which 1-4 H atoms can be replaced independently from one another by Hal, OH or COOY;
each Ar is independently an unsaturated or aromatic mono- or bicyclic carbocycle having 3-10 C atoms,
  which can be substituted by at least one substituent selected from the group of A, Hal, OY, COOY, CONH$_2$, NHCOY, —(CY$_2$)$_n$—NY$_2$, NO$_2$, SO$_2$Y, CN and Het$^2$, or which can be fused to Cyc;
each Het$^1$ is independently an unsaturated or aromatic mono- or bicyclic heterocycle having 1-10 C atoms and 1-4 N, O and/or S atoms,
  which can be substituted by at least one substituent selected from the group of Hal, A, Cyc, OY, COOY, CONH$_2$, NHCOY, NY$_2$, SO$_2$Y, SO$_2$NY$_2$, NHSO$_2$Y, CN and Ar;
each Het$^2$ is independently an unsaturated monocyclic 5-membered heterocycle having
  1-3 C atoms and 2-4 N and/or S atoms,
  which can be substituted by A;
each Het$^3$ is independently a saturated mono- or bicyclic heterocycle having 3-7 C atoms and 1-4 N, O and/or S atoms, which can be substituted by at least one substituent selected from the group of =O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar;

each Hal is independently F, Cl, Br or I;

m, n denote independently from one another 0, 1, 2, 3, 4, 5 or 6; and p denotes 1, 2 or 3;

and/or physiologically acceptable salts thereof.

2. The compound according to claim 1, wherein

W$^1$, W$^2$ each denote N;

R$^6$, R$^7$ together denote —(CY$_2$)$_p$—; and p denotes 2.

3. The compound according to claim 1, wherein X denotes CO.

4. The compound according to claim 1, wherein

R$^9$ denotes H; and

R$^{10}$ denotes Hal, A, OY, —O(CY$_2$)$_n$—OY, NY$_2$ or Cyc.

5. The compound according to claim 1, of sub-formula (I-B)

(I-B)

wherein

R$^1$ denotes Het$^3$, Het$^1$, Ar or Cyc;

R$^2$ denotes H;

R$^5$ denotes Ar or Het$^1$;

R$^{10}$ denotes Hal, Y, OY, —O(CY$_2$)$_n$—OY, NY$_2$ or Cyc; with the proviso that both R$^9$, and R$^{10}$ are not H; or R$^2$, R$^{10}$ together denote —(CY$_2$)$_2$— or —(CY)$_2$—;

Y denotes H or A;

A denotes unbranched or branched alkyl having 1-6 C atoms, in which 1-4 H atoms can be replaced independently from one another by Hal and/or =O;

Cyc denotes cycloalkyl having 3-6 C atoms, in which 1-3 H atoms can be replaced independently from one another by OH or COOY;

Ar denotes an aromatic monocyclic carbocycle having 6-8 C atoms, which can be mono- or disubstituted by at least one substituent selected from the group of A, Hal, OA, CONH$_2$, —(CY$_2$)$_n$—NY$_2$, NO$_2$ and CN;

Het$^1$ denotes an unsaturated or aromatic monocyclic heterocycle having 1-6 C atoms and 1-4 N, O and/or S atoms, which can be mono- or disubstituted by at least one substituent selected from the group of Hal, A, Cyc, OA, CONH$_2$, NHCOA, NHA, SO$_2$NH$_2$ and CN, or an aromatic bicyclic heterocycle having 6-9 C atoms and 1-3 N and/or S atoms, which can be monosubstituted by A;

Het$^3$ denotes a saturated monocyclic heterocycle having 3-6 C atoms and 1-3 N, O and/or S atoms, which can be mono- or disubstituted by at least one substituent selected from the group of =O, A, Cyc, OY, COA, COOA, CONHA and SO$_2$A;

Hal denotes F, Cl, Br or I; and n denotes 0, 1, 2 or 3;

and/or physiologically acceptable salts thereof.

6. The compound according to claim 1, of sub-formula (I-C)

(I-C)

wherein

R$^1$ denotes Het$^3$ or Cyc;

R$^2$ denotes H;

R$^{10}$ denotes Hal, A, OA, —O(CY$_2$)$_n$-OA, NA$_2$ or Cyc; or

R$^2$, R$^{10}$ together denote —(CH$_2$)$_2$— or —(CH)$_2$—;

Y denotes H or A;

A denotes unbranched or branched alkyl having 1-6 C atoms, in which 1-4 H atoms can be replaced independently from one another by Hal;

Cyc denotes cycloalkyl having 3-6 C atoms, in which 1-3 H atoms can be replaced independently from one another by OH or COOH;

Ar denotes an aromatic monocyclic carbocycle having 6-8 C atoms, which can be mono- or disubstituted by A or Hal;

Het$^1$ denotes an unsaturated or aromatic monocyclic heterocycle having 1-6 C atoms and 1-3 N, O and/or S atoms, which can be mono- or disubstituted by at least one substituent selected from the group of Cyc, A or Hal;

Het$^3$ denotes a saturated monocyclic heterocycle having 3-6 C atoms and 1-3 N, O and/or S atoms, which can be mono- or disubstituted by at least one substituent selected from the group of =O, A or Hal;

Hal denotes F, Cl or Br; and n denotes 0, 1, 2 or 3;

and/or physiologically acceptable salts thereof.

7. The compound according to claim 1, selected from the group of:

123
-continued
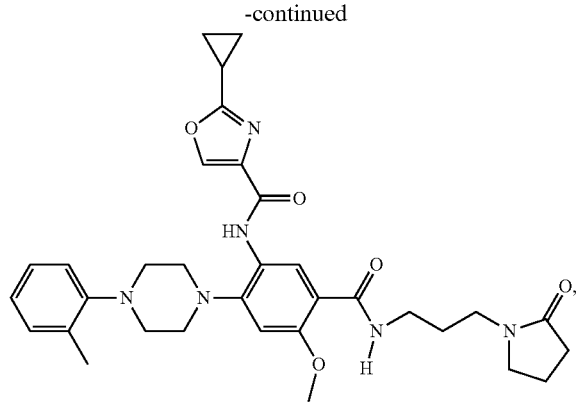
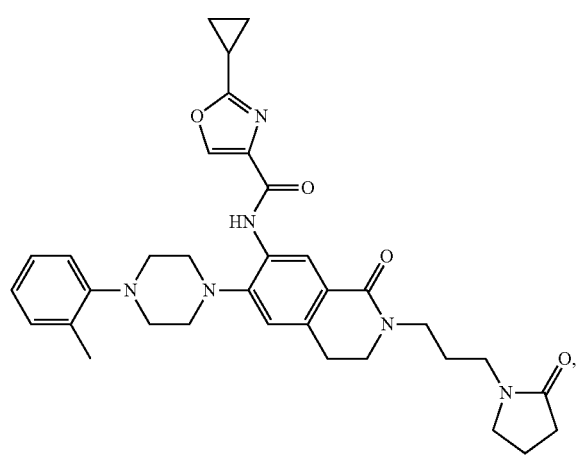
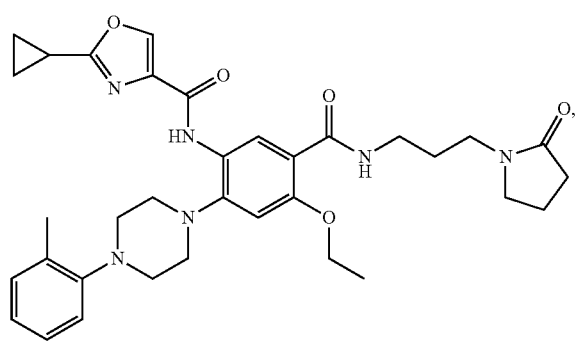
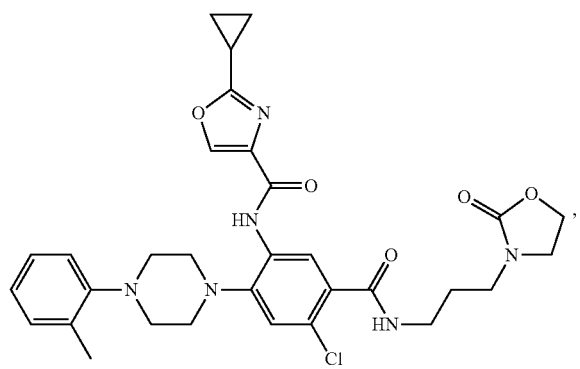
124
-continued
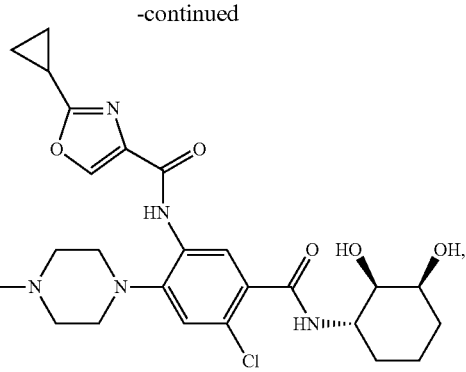
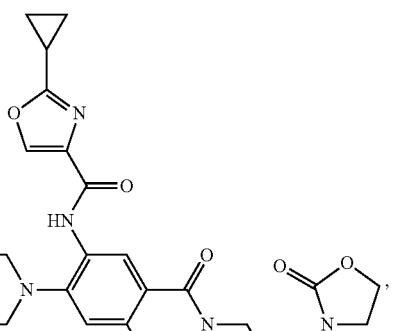
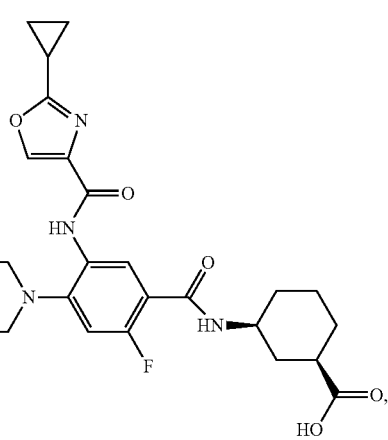
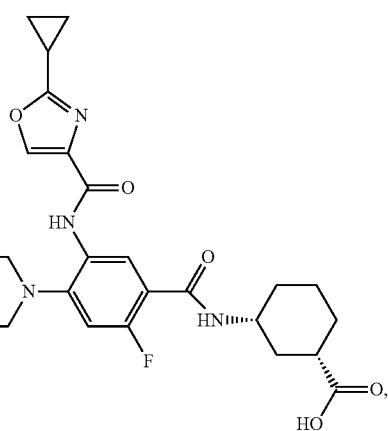

-continued

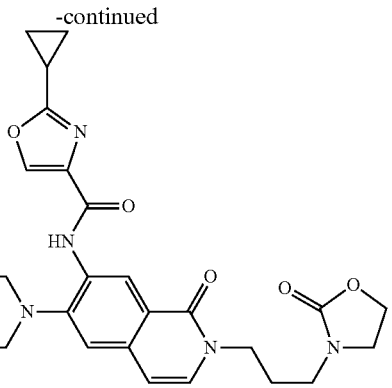

and/or physiologically acceptable salts thereof.

8. A process for manufacturing a compound of formula (I) comprising the steps of:
(a) reacting a compound of formula (II)

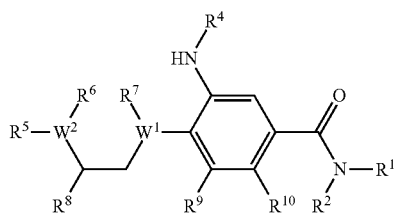

wherein $W^1$, $W^2$, $R^1$, $R^2$ and $R^4$ to $R^{10}$ are as defined in claim 1,
with a compound of formula (III)

wherein $R^3$ and X are as defined in claim 1,
to yield a compound of formula (I)

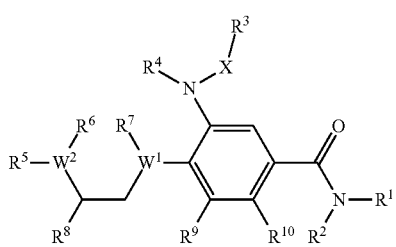

wherein $W^1$, $W^2$, $R^1$ to $R^{10}$ and X are as defined in claim 1,
and optionally (b) converting a base or an acid of the compound of formula (I) into a salt thereof.

9. A compound of formula (II-A)

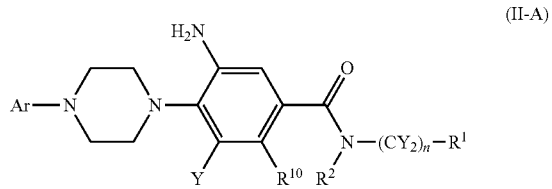

wherein
$R^1$ denotes $Het^3$ or Ar;
$R^2$ denotes H;
$R^{10}$ denotes Hal, A, OA, —O(CY$_2$)$_n$-OA, NA$_2$ or Cyc; or
$R^2$, $R^{10}$ together denote —(CH$_2$)$_2$— or —(CH)$_2$—;
Y denotes H or A;
each A independently denotes unbranched or branched alkyl having 1-6 C atoms, in which 1-4 H atoms can be replaced independently from one another by Hal;
Cyc denotes cycloalkyl having 3-6 C atoms, in which 1-3 H atoms can be replaced independently from one another by OH;
Ar denotes an aromatic monocyclic carbocycle having 6-8 C atoms, which can be mono- or disubstituted by A, Hal or —(CY$_2$)$_n$—NY$_2$;
$Het^3$ denotes a saturated monocyclic heterocycle having 3-6 C atoms and 1-3 N, O and/or S atoms, which can be mono- or disubstituted by at least one substituent selected from the group of =O, A or Hal;
Hal denotes F, Cl or Br; and
n denotes 0, 1, 2 or 3.

10. A pharmaceutical composition comprising as active ingredient at least one compound according to claim 1 and/or physiologically acceptable salts thereof together with pharmaceutically tolerable adjuvants for oral administration.

11. A method for treating fertility disorders, wherein at least one compound according to claim 1 and/or physiologically acceptable salts thereof, is administered to a mammal in need of such treatment of fertility disorders.

12. A method for in-vitro fertilization comprising the steps of:
(a) treating a mammal according to the method of claim 11,
(b) collecting ova from said mammal,
(c) fertilizing said ova, and
(d) implanting said fertilized ova into a host mammal.

13. A method for modulating an FSH receptor, wherein a system expressing the FSH receptor is contacted in the presence of FSH with at least one compound according to claim 1 and/or physiologically acceptable salts thereof under conditions such that the FSH receptor is modulated.

14. The pharmaceutical composition of claim 10, further comprising at least another active pharmaceutical ingredient.

15. The compound according to claim 1, wherein $R^3$ denotes —(CY$_2$)$_n$-Het$^1$.

16. The compound according to claim 1, wherein $R^5$ denotes E-Ar.

17. The compound according to claim 1, wherein $R^2$, $R^{10}$ together denote —(CY$_2$)$_2$— or —(CY)$_2$—.

* * * * *